US012606620B2

(12) United States Patent
Choi et al.

(10) Patent No.: US 12,606,620 B2
(45) Date of Patent: Apr. 21, 2026

(54) ANTI-LILRB1 ANTIBODY AND USES THEREOF

(71) Applicant: LG CHEM, LTD., Seoul (KR)

(72) Inventors: Yoon Aa Choi, Daejeon (KR); Han Byul Kim, Daejeon (KR); Shinyoung Kang, Daejeon (KR); Jung A Kim, Daejeon (KR); Heehang Kim, Daejeon (KR); Minsoon Kim, Daejeon (KR); Junhaeng Cho, Daejeon (KR)

(73) Assignee: LG CHEM, LTD., Seoul (KR)

( * ) Notice: Subject to any disclaimer, the term of this patent is extended or adjusted under 35 U.S.C. 154(b) by 497 days.

(21) Appl. No.: 18/003,582

(22) PCT Filed: Jul. 27, 2021

(86) PCT No.: PCT/KR2021/009696
§ 371 (c)(1),
(2) Date: Dec. 28, 2022

(87) PCT Pub. No.: WO2022/025585
PCT Pub. Date: Feb. 3, 2022

(65) Prior Publication Data
US 2023/0374127 A1      Nov. 23, 2023

(30) Foreign Application Priority Data
Jul. 28, 2020      (KR) ........................ 10-2020-0094053

(51) Int. Cl.
*C07K 16/28*        (2006.01)
*A61K 39/00*        (2006.01)
*A61P 35/00*        (2006.01)

(52) U.S. Cl.
CPC .......... *C07K 16/2803* (2013.01); *A61K 39/00* (2013.01); *A61P 35/00* (2018.01); *A61K 2039/505* (2013.01); *C07K 2317/21* (2013.01); *C07K 2317/92* (2013.01)

(58) Field of Classification Search
CPC ............ C07K 16/2803; C07K 2317/21; C07K 2317/92; C07K 2317/55; C07K 2317/73; C07K 16/28; C07K 2317/565; A61K 39/00; A61K 2039/505; A61P 35/00
See application file for complete search history.

(56) References Cited

U.S. PATENT DOCUMENTS

| | | | |
|---|---|---|---|
| 10,669,343 | B2 | 6/2020 | Fransson et al. |
| 2013/0324593 | A1 | 12/2013 | Kim et al. |
| 2015/0174203 | A1 | 6/2015 | Chen et al. |
| 2018/0355043 | A1 | 12/2018 | Martinez et al. |
| 2019/0241664 | A1 | 8/2019 | Maute |
| 2019/0330593 | A1 | 10/2019 | Bernstein et al. |
| 2020/0079851 | A1 | 3/2020 | Zhang et al. |
| 2022/0153836 | A1 | 5/2022 | Mandel et al. |
| 2023/0374127 | A1 | 11/2023 | Choi et al. |

FOREIGN PATENT DOCUMENTS

| | | |
|---|---|---|
| CN | 108713027 A | 10/2018 |
| EP | 3491017 A2 | 6/2019 |
| JP | 2017-517259 A | 6/2017 |
| KR | 10-1038126 B1 | 5/2011 |
| TW | 202340258 A | 10/2023 |
| WO | 2013-181438 A2 | 12/2013 |
| WO | 2016-065329 A1 | 4/2016 |
| WO | 2016-144728 A2 | 9/2016 |
| WO | 2018-022881 A2 | 2/2018 |
| WO | 2019-144052 A1 | 7/2019 |
| WO | 2020-023268 A1 | 1/2020 |
| WO | 2020-136145 A2 | 7/2020 |
| WO | 2020-136147 A1 | 7/2020 |
| WO | 2021028921 A1 | 2/2021 |
| WO | 2021133036 A1 | 7/2021 |

OTHER PUBLICATIONS

Kovalenko and Streltsova, Adaptive Features of Natural Killer Cells—Lymphocytes of Innate Immunity, Shemyakin and Ovchinnikov Institute of Bioorganic Chemistry of the Russian Academy of Sciences, 2016, No. 6, 649-667 and its English Abstract.
Extended European Search Report issued for the corresponding European Patent Application No. 21851407.3, on Feb. 15, 2024, 11 pages.
International Search Report issued for International Application No. PCT/KR2021/009696 on Nov. 4, 2021, 7 pages.
Kim et al., LILRB1 Blockade Enhances Bispecific T Cell Engager Antibody-Induced Tumor Cell Killing by Effector CD8 + T Cells, The Journal of Immunology, Jun. 28, 2019, 203, pp. 1076-1087.
Barkal et al., Engagement of MHC class I by the inhibitory receptor LILRB1 suppresses macrophages and is a target of cancer immunotherapy, Nature Immunology (2018) 19(1), 76-84.
Genbank: AMT74511.1, "immunoglobulin heavy chain VRC01c-HuGL, partial [*Homo sapiens*]" Apr. 7, 2016, retrieved from <https://www.ncbi.nlm.nih.gov/protein/1013062027> on Jul. 23, 2025, 2 pages.
"The Role of Human Leukocyte Antigen G5 in Modulating Trophoblast Invasion and Endometrial Receptivity", Aug. 15, 2013, with English abstract, 127 pages.

*Primary Examiner* — Misook Yu
*Assistant Examiner* — Grace H Lunde
(74) *Attorney, Agent, or Firm* — ROTHWELL, FIGG, ERNST & MANBECK, P.C.

(57)      ABSTRACT

The present invention relates to an anti-LILRB1 antibody having increased specificity for LILRB1, and to uses thereof. Specifically, an anti-LILRB1 antibody or an antigen-binding fragment thereof, and uses thereof in treating cancer are provided.

17 Claims, 5 Drawing Sheets
Specification includes a Sequence Listing.

【Figure 1】
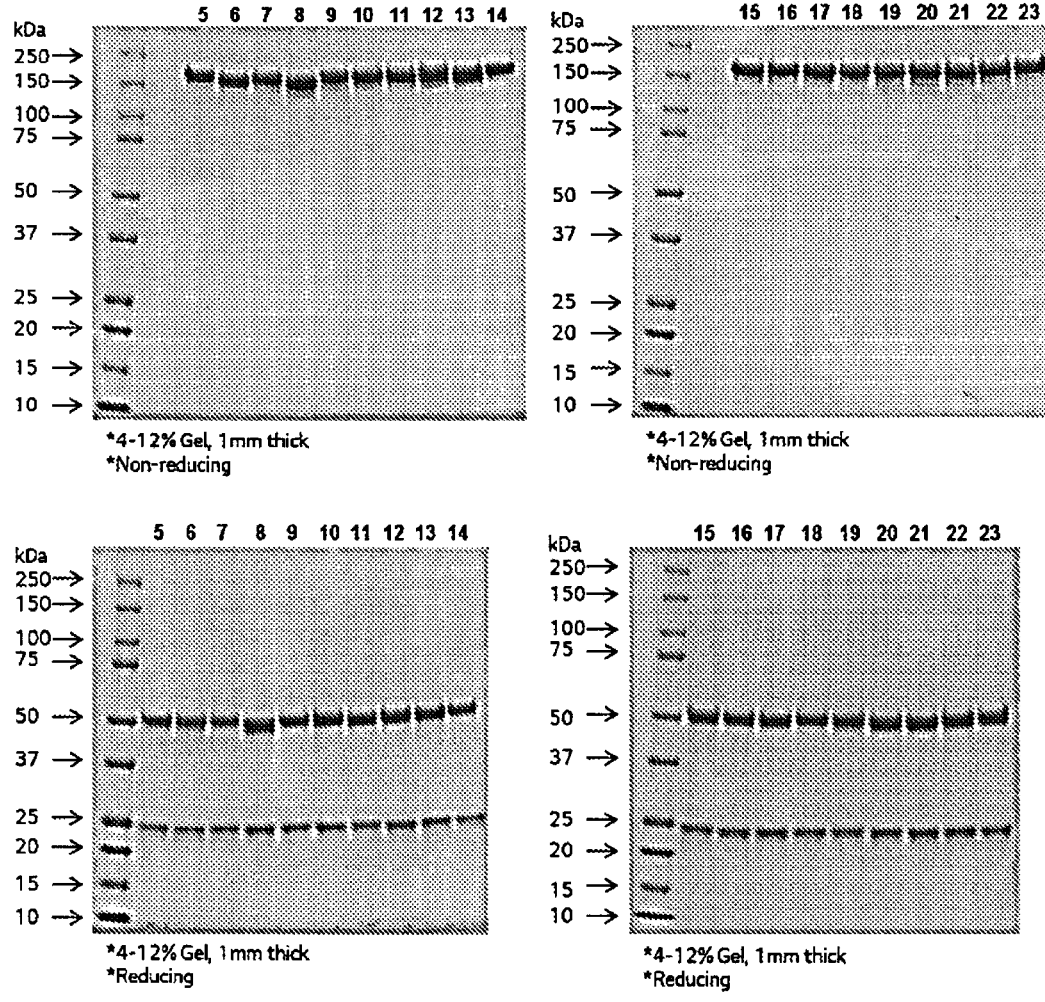

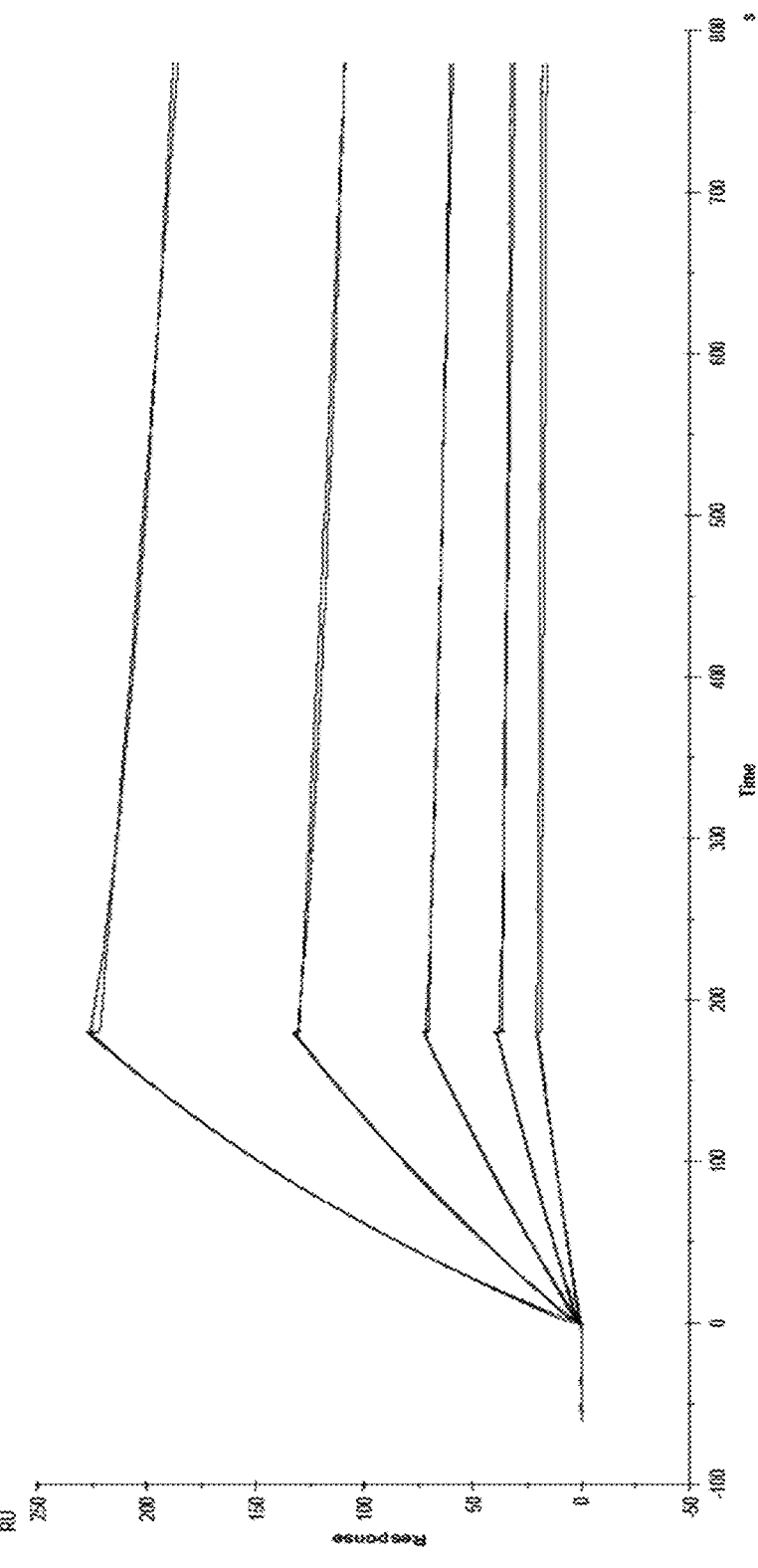
[Figure 2]

【Figure 3】
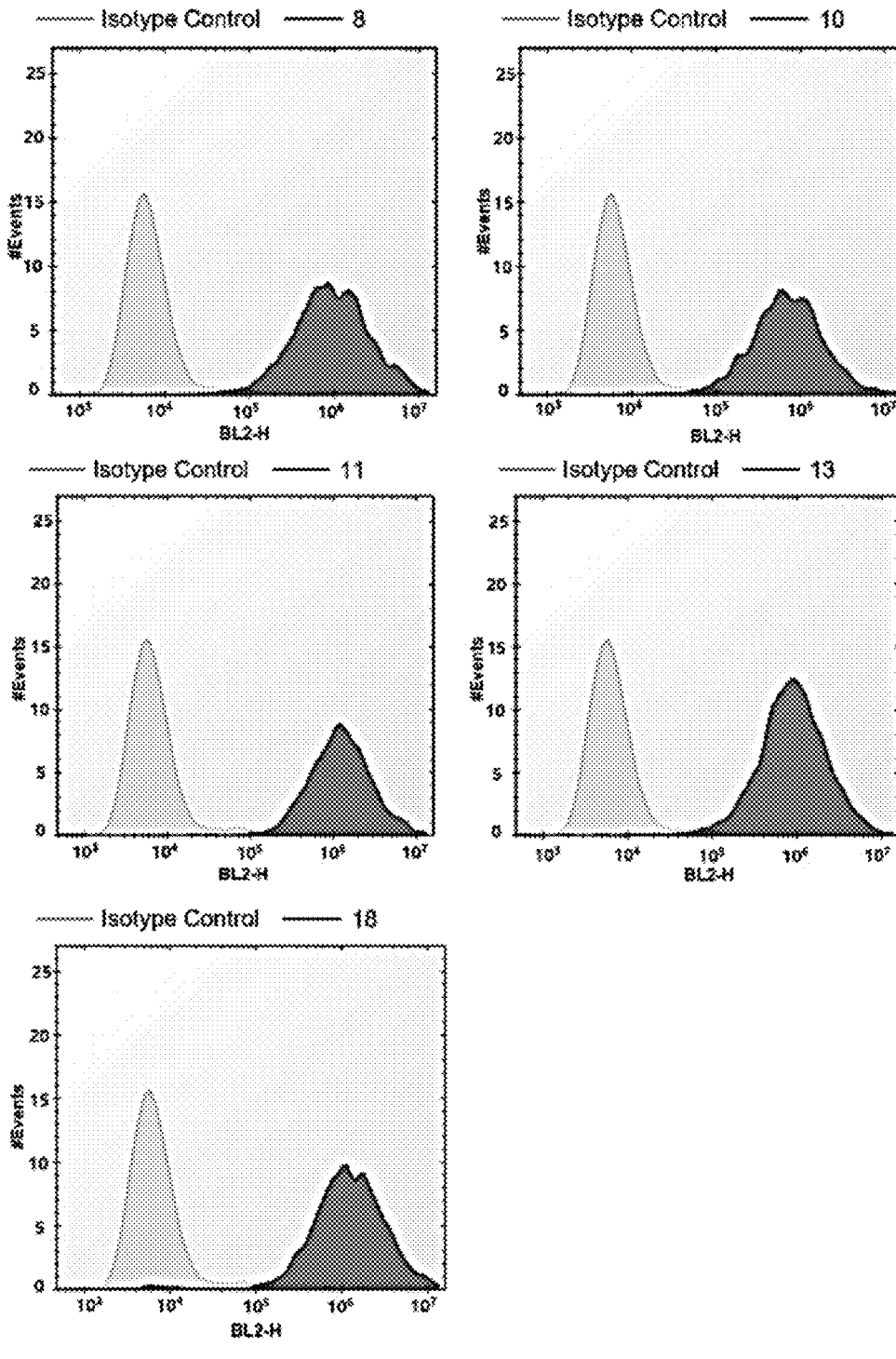

【Figure 4】
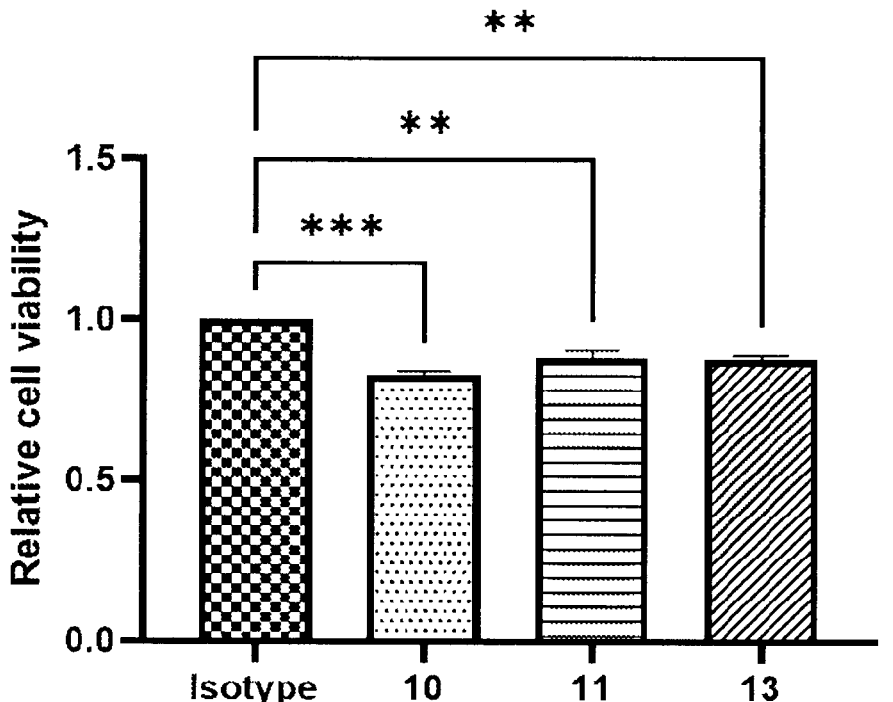
* Data are presented as mean and error SEM (n=3), *P<0.05

【Figure 5】
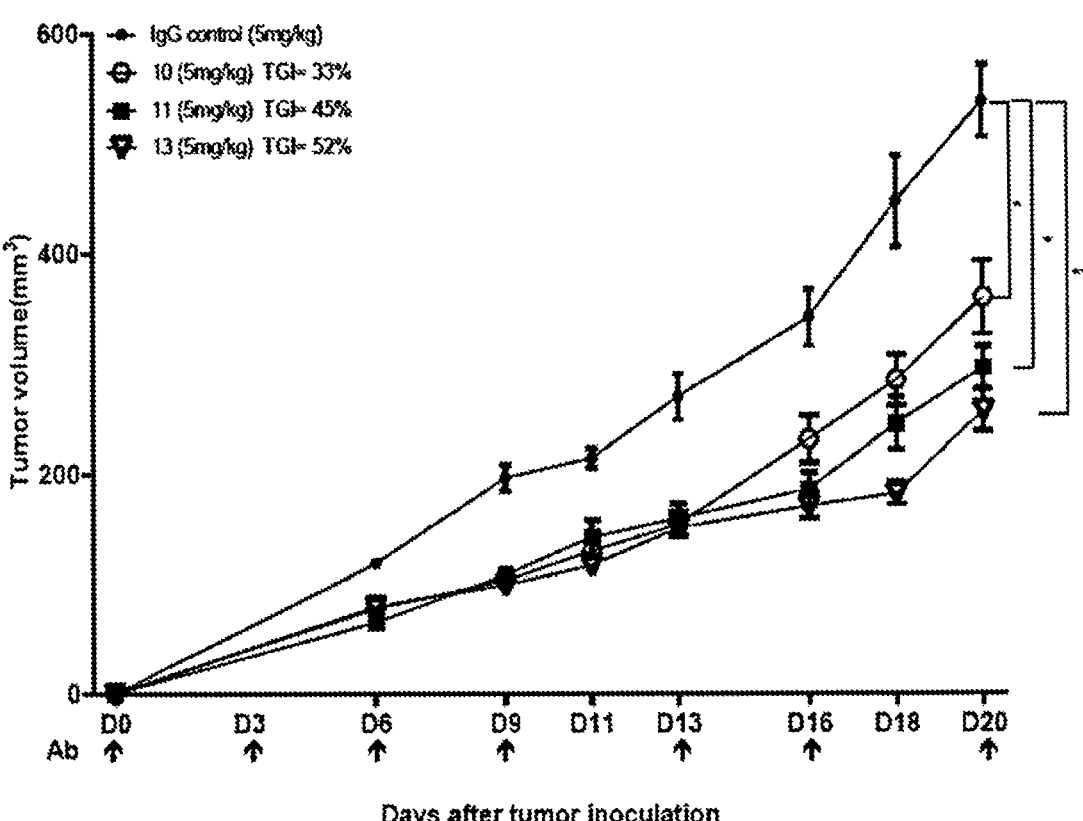
HCT-116 cell / THP 1 cell derived macrophage / NOG Mouse / anti-LILRB-1 / Intraperitoneal administration for 3 weeks / C033
Days after tumor inoculation
Data are presented as mean and error SEM of 6 mice per group.*P < 0.05, **P < 0.01

ANTI-LILRB1 ANTIBODY AND USES THEREOF

CROSS-REFERENCE TO RELATED APPLICATIONS

This application is a 35 U.S.C. 371 National Phase Entry Application from PCT/KR2021/009696 filed on Jul. 27, 2021, which claims the benefits of KR 10-2020-0094053 filed on Jul. 28, 2020 with the Korean Intellectual Property Office, the entire disclosure of which is herein incorporated by reference.

TECHNICAL FIELD

The instant application contains a Sequence Listing which has been submitted via EFS-Web and is hereby incorporated by reference in its entirety. Said Sequence Listing, created on Jul. 24, 2023, is named 3570-846_ST25.txt and is 205,619 bytes in size.

The disclosure relates to an anti-LILRB1 antibody and uses thereof. More specifically, an anti-LILRB1 antibody or antigen-binding fragment thereof, and a use thereof for cancer therapy are provided.

BACKGROUND OF THE INVENTION

Leukocyte immunoglobulin-like receptor subfamily B member 1 (LILRB1; also known as ILT2, CD85j, or LIR-1) is an inhibitory receptor, which is expressed in cells such as B cells, T cells, NK cells, dendritic cells, macrophages, and other immune cells. LILRB1 participates in a signal transduction mechanism of inhibiting activities of immune cells by binding classical and non-classical MHC class I.

Therefore, it is required to develop a substance targeting LILRB1.

DISCLOSURE

Brief Summary of the Invention

An embodiment provides an anti-LILRB1 antibody, which binds to LILRB1, or antigen-binding fragment thereof. The anti-LILRB1 antibody or antigen-binding fragment thereof may have an activity to inhibit immune evasion of cancer cells. Furthermore, the anti-LILRB1 antibody or antigen-binding fragment thereof may have an anti-cancer effect. The anti-cancer effect may be against a cancer cell expressing or overexpressing MHC Class I on the surface.

Another embodiment provides a pharmaceutical composition for treatment and/or prevention of a cancer, the composition comprising the anti-LILRB1 antibody or antigen-binding fragment thereof as an active ingredient. Another embodiment provides a method for treating and/or preventing cancer, comprising administering to a subject in need thereof a pharmaceutically effective amount of the anti-LILRB1 antibody or antigen-binding fragment thereof. Another embodiment provides a use of the anti-LILRB1 antibody or antigen-binding fragment thereof for the treatment and/or prevention of cancer or for the manufacture of a pharmaceutical composition for the treatment and/or prevention of cancer.

Another embodiment provides a pharmaceutical composition for inhibiting immune evasion of cancer cells comprising the anti-LILRB1 antibody or antigen-binding fragment thereof. Another embodiment provides a method for inhibiting immune evasion of cancer cells, comprising administering a pharmaceutically effective amount of the anti-LILRB1 antibody or antigen-binding fragment thereof to a subject in need of inhibiting immune evasion of cancer cells. Another example provides a use of the anti-LILRB1 antibody or antigen-binding fragment thereof for inhibiting immune evasion of cancer cells, or for the manufacture of a pharmaceutical composition for inhibiting immune evasion of cancer cells.

DETAILED DESCRIPTION OF THE INVENTION

An embodiment provides an anti-LILRB1 antibody, which binds to LILRB1, or antigen-binding fragment thereof. The anti-LILRB1 antibody or antigen-binding fragment thereof may have an activity to inhibit immune evasion of cancer cells. In addition, the anti-LILRB1 antibody or antigen-binding fragment thereof may have an anti-cancer effect.

The anti-LILRB1 antibody or antigen-binding fragment thereof may comprise the following complementarity determining regions (CDRs):

Based on the CDR definition according to Kabat numbering (Kabat, E. A., Wu, T. T., Perry, H., Gottesman, K. and Foeller, C. (1991) Sequences of Proteins of Immunological Interest, Fifth Edition. NIH Publication No. 91-3242; http://www.abysis.org/), a CDR-L1 comprising an amino acid sequence of SEQ ID NO: 1, 13, 25, 37, 49, 61, 73, 85, 97, 109, 121, 133, 145, 157, 169, 181, 193, 205, or 217, a CDR-L2 comprising an amino acid sequence of SEQ ID NO: 2, 14, 26, 38, 50, 62, 74, 86, 98, 110, 122, 134, 146, 158, 170, 182, 194, 206, or 218, a CDR-L3 comprising an amino acid sequence of SEQ ID NO: 3, 15, 27, 39, 51, 63, 75, 87, 99, 111, 123, 135, 147, 159, 171, 183, 195, 207, or 219, a CDR-H1 comprising an amino acid sequence of SEQ ID NO: 4, 16, 28, 40, 52, 64, 76, 88, 100, 112, 124, 136, 148, 160, 172, 184, 196, 208 or 220, a CDR-H2 comprising an amino acid sequence of SEQ ID NO: 5, 17, 29, 41, 53, 65, 77, 89, 101, 113, 125, 137, 149, 161, 173, 185, 197, 209 or 221, and a CDR-H3 comprising an amino acid sequence of SEQ ID NO: 6, 18, 30, 42, 54, 66, 78, 90, 102, 114, 126, 138, 150, 162, 174, 186, 198, 210 or 222.

In a specific embodiment, combinations of 6 CDRs (CDR-L1, CDR-L2, CDR-L3, CDR-H1, CDR-H2, and CDR-H3) that can be comprised in the anti-LILRB1 antibody or antigen-binding fragment thereof provided in this disclosure are illustrated in Table 1:

TABLE 1

| Clone | CDR | Amino Acid Sequence (N→C) (Kabat) | SEQ ID NO |
|---|---|---|---|
| 5 | CDR-L1 | RASQSIANYLN | 1 |
| | CDR-L2 | ATSTLQS | 2 |
| | CDR-L3 | QQSYSFPWT | 3 |
| | CDR-H1 | AYGIH | 4 |
| | CDR-H2 | WIIPLSGGAHYAQKFQG | 5 |
| | CDR-H3 | LYGWAEYFDV | 6 |

TABLE 1-continued

| Clone | CDR | Amino Acid Sequence (N→C) (Kabat) | SEQ ID NO |
|---|---|---|---|
| 6 | CDR-L1 | RASQSISNYLN | 13 |
|  | CDR-L2 | AASTLQS | 14 |
|  | CDR-L3 | QQSYSFPWT | 15 |
|  | CDR-H1 | SYTIS | 16 |
|  | CDR-H2 | WISPELGTSNYAQKFQG | 17 |
|  | CDR-H3 | LRYGQTLYGFDI | 18 |
| 7 | CDR-L1 | RASQSISNWLN | 25 |
|  | CDR-L2 | GTSSLQS | 26 |
|  | CDR-L3 | QQSYSFPFT | 27 |
|  | CDR-H1 | SYGMH | 28 |
|  | CDR-H2 | WIIPVSGGATYAQKFQG | 29 |
|  | CDR-H3 | GSWAYYAEFDY | 30 |
| 8 | CDR-L1 | RASQSISSYLN | 37 |
|  | CDR-L2 | AASTLQS | 38 |
|  | CDR-L3 | QQSYSFPYT | 39 |
|  | CDR-H1 | SYGIH | 40 |
|  | CDR-H2 | WIIPISGTTNYAQKFQG | 41 |
|  | CDR-H3 | VGGVGLYVFDV | 42 |
| 9 | CDR-L1 | RASQSISNYLN | 49 |
|  | CDR-L2 | AASSLQS | 50 |
|  | CDR-L3 | QQSYSFPWT | 51 |
|  | CDR-H1 | SYAIH | 52 |
|  | CDR-H2 | WIVPGLGVTNYAQKFQG | 53 |
|  | CDR-H3 | QATLYQTEYMDV | 54 |
| 10 | CDR-L1 | RASQSISNYLN | 61 |
|  | CDR-L2 | AASNLQS | 62 |
|  | CDR-L3 | QQSYSFPFT | 63 |
|  | CDR-H1 | SHYMH | 64 |
|  | CDR-H2 | WISPYLGSTNYAQKFQG | 65 |
|  | CDR-H3 | DETGSTYGAFDY | 66 |
| 11 | CDR-L1 | RASQSISNYLN | 73 |
|  | CDR-L2 | DASTLQS | 74 |
|  | CDR-L3 | QQSYSFPWT | 75 |
|  | CDR-H1 | SYYVH | 76 |
|  | CDR-H2 | WISPYSGGTNYAQKFQG | 77 |
|  | CDR-H3 | DYYVSAYGAFDY | 78 |
| 12 | CDR-L1 | RASQDISNYLN | 85 |
|  | CDR-L2 | ATSSLQS | 86 |
|  | CDR-L3 | QQSYSFPWT | 87 |

TABLE 1-continued

| Clone | CDR | Amino Acid Sequence (N→C) (Kabat) | SEQ ID NO |
|---|---|---|---|
|  | CDR-H1 | SYDIH | 88 |
|  | CDR-H2 | RIVPYLGVTNYAQKFQG | 89 |
|  | CDR-H3 | RQSQSSVYAFDI | 90 |
| 13 | CDR-L1 | RASQSISNYLN | 97 |
|  | CDR-L2 | AASRLQS | 98 |
|  | CDR-L3 | QQSYSFPFT | 99 |
|  | CDR-H1 | GYYIH | 100 |
|  | CDR-H2 | WISPSSGGTIYAQKFQG | 101 |
|  | CDR-H3 | DISVRVVQAFDY | 102 |
| 14 | CDR-L1 | RASQSISNYLN | 109 |
|  | CDR-L2 | ATSNLQS | 110 |
|  | CDR-L3 | QQSYSFPWT | 111 |
|  | CDR-H1 | SYYMH | 112 |
|  | CDR-H2 | WISPYLGITNYAQKFQG | 113 |
|  | CDR-H3 | AGYQQAQYWFDY | 114 |
| 15 | CDR-L1 | RASQSISNYLN | 121 |
|  | CDR-L2 | ATSSLQS | 122 |
|  | CDR-L3 | QQSYSFPYT | 123 |
|  | CDR-H1 | SYAMS | 124 |
|  | CDR-H2 | WIIPISGTTNYAQKFQG | 125 |
|  | CDR-H3 | QHSVGSVFDY | 126 |
| 16 | CDR-L1 | RASQDISSWLN | 133 |
|  | CDR-L2 | AASSLQS | 134 |
|  | CDR-L3 | QQSYSFPWT | 135 |
|  | CDR-H1 | SYYMT | 136 |
|  | CDR-H2 | GISPILGVTNYAQKFQG | 137 |
|  | CDR-H3 | LLVGVSETYFDY | 138 |
| 17 | CDR-L1 | RASQSISNYLN | 145 |
|  | CDR-L2 | AASNMHS | 146 |
|  | CDR-L3 | QQSHSFPWT | 147 |
|  | CDR-H1 | TYAMS | 148 |
|  | CDR-H2 | GISPTLGIANYAQKFQG | 149 |
|  | CDR-H3 | VRYAGWTGYFDL | 150 |
| 18 | CDR-L1 | RASQSISRWLN | 157 |
|  | CDR-L2 | AASRLQS | 158 |
|  | CDR-L3 | QQSESFPWT | 159 |
|  | CDR-H1 | SYDIN | 160 |

TABLE 1-continued

| Clone | CDR | Amino Acid Sequence (N→C) (Kabat) | SEQ ID NO |
|---|---|---|---|
|  | CDR-H2 | WIIPTSGSTNYAQKFQG | 161 |
|  | CDR-H3 | DSQSSYIGYFDV | 162 |
| 19 | CDR-L1 | RASQSISNYLN | 169 |
|  | CDR-L2 | DTSSLQS | 170 |
|  | CDR-L3 | QQSYSTPYT | 171 |
|  | CDR-H1 | AYGIS | 172 |
|  | CDR-H2 | RIIPYLGTANYAQKFQG | 173 |
|  | CDR-H3 | LSYGIGYESFDV | 174 |
| 20 | CDR-L1 | RASQSISSYLN | 181 |
|  | CDR-L2 | DTSTLQS | 182 |
|  | CDR-L3 | QQSYSFPWT | 183 |
|  | CDR-H1 | SYAMS | 184 |
|  | CDR-H2 | SISSSGGSTYYADSVKG | 185 |
|  | CDR-H3 | ELGGYGFSYFDY | 186 |
| 21 | CDR-L1 | RASQSIRNYLN | 193 |
|  | CDR-L2 | ATSSLQS | 194 |
|  | CDR-L3 | QQSYSFPWT | 195 |
|  | CDR-H1 | DYAMS | 196 |
|  | CDR-H2 | GISGSDIYYADSVKG | 197 |
|  | CDR-H3 | AVSYWSYTFDY | 198 |
| 22 | CDR-L1 | RASQSIGSYLN | 205 |
|  | CDR-L2 | DASTLQS | 206 |

TABLE 1-continued

| Clone | CDR | Amino Acid Sequence (N→C) (Kabat) | SEQ ID NO |
|---|---|---|---|
|  | CDR-L3 | QQSYSFPWT | 207 |
|  | CDR-H1 | SYAMH | 208 |
|  | CDR-H2 | GISSSGGTTYYADSVKG | 209 |
|  | CDR-H3 | ALGVVGGTWFDY | 210 |
| 23 | CDR-L1 | RASQSISNYLN | 217 |
|  | CDR-L2 | DTSTLQS | 218 |
|  | CDR-L3 | QQSYSFPWT | 219 |
|  | CDR-H1 | DYAMH | 220 |
|  | CDR-H2 | AISGSGGYTHYADSVKG | 221 |
|  | CDR-H3 | SATFGVWETFDV | 222 |

In an embodiment, the anti-LILRB1 antibody or antigen-binding fragment thereof may comprise:

a light chain variable region comprising a CDR-L1, a CDR-L2, and CDR-L3, and a heavy chain variable region comprising a CDR-H1, a CDR-H2, and a CDR-H3, wherein the CDRs are as described above.

In an embodiment, the anti-LILRB1 antibody or antigen-binding fragment thereof may comprise:

a light chain variable region comprising an amino acid sequence of SEQ ID NO: 7, 19, 31, 43, 55, 67, 79, 91, 103, 115, 127, 139, 151, 163, 175, 187, 199, 211, or 223, and a heavy chain variable region comprising an amino acid sequence of SEQ ID NO: 9, 21, 33, 45, 57, 69, 81, 93, 105, 117, 129, 141, 153, 165, 177, 189, 201, 213, or 225.

In a specific embodiment, combinations of a light chain variable region and a heavy chain variable region that can be comprised in the anti-LILRB1 antibody or antigen-binding fragment thereof provided in this disclosure are illustrated in Table 2:

TABLE 2

| Clone | variable region | Amino acid sequence (N→C) | SEQ ID NO |
|---|---|---|---|
| 5 | light chain variable region | DIQMTQSPSSLSASVGDRVTITCRASQSIANYLNWYQQK PGKAPKLLIYATSTLQSGVPSRFSGSGSGTDFTLTISSLQ PEDFATYYCQQSYSFPWTFGQGTKVEIK | 7 |
|  | heavy chain variable region | QVQLVQSGAEVKKPGSSVKVSCKASGGTFSAYGIHWVR QAPGQGLEWMGWIIPLSGGAHYAQKFQGRVTITADESTS TAYMELSSLRSEDTAVYYCARLYGWAEYFDVWGQGTLVT VSS | 9 |
| 6 | light chain variable region | DIQMTQSPSSLSASVGDRVTITCRASQSISNYLNWYQQK PGKAPKLLIYAASTLQSGVPSRFSGSGSGTDFTLTISSLQ PEDFATYYCQQSYSFPWTFGQGTKVEIK | 19 |
|  | heavy chain variable region | QVQLVQSGAEVKKPGSSVKVSCKASGGTFSSYTISWVR QAPGQGLEWMGWISPELGTSNYAQKFQGRVTITADEST STAYMELSSLRSEDTAVYYCARLRYGQTLYGFDIWGQGT LVTVSS | 21 |
| 7 | light chain variable region | DIQMTQSPSSLSASVGDRVTITCRASQSISNWLNWYQQK PGKAPKLLIYGTSSLQSGVPSRFSGSGSGTDFTLTISSLQ PEDFATYYCQQSYSFPFTFGQGTKVEIK | 31 |

TABLE 2-continued

| Clone | variable region | Amino acid sequence (N→C) | SEQ ID NO |
|-------|-----------------|---------------------------|-----------|
|  | heavy chain variable region | QVQLVQSGAEVKKPGSSVKVSCKASGGTFSSYGMHWV RQAPGQGLEWMGWIIPVSGGATYAQKFQGRVTITADEST STAYMELSSLRSEDTAVYYCARGSWAYYAEFDYWGQGT LVTVSS | 33 |
| 8 | light chain variable region | DIQMTQSPSSLSASVGDRVTITCRASQSISSYLNWYQQK PGKAPKLLIYAASTLQSGVPSRFSGSGSGTDFTLTISSLQ PEDFATYYCQQSYSFPYTFGQGTKVEIK | 43 |
|  | heavy chain variable region | QVQLVQSGAEVKKPGSSVKVSCKASGGTFSSYGIHWVR QAPGQGLEWMGWIIPISGTTNYAQKFQGRVTITADESTS TAYMELSSLRSEDTAVYYCARVGGVGLYVFDVWGQGTLV TVSS | 45 |
| 9 | light chain variable region | DIQMTQSPSSLSASVGDRVTITCRASQSISNYLNWYQQK PGKAPKLLIYAASSLQSGVPSRFSGSGSGTDFTLTISSLQ PEDFATYYCQQSYSFPWTFGQGTKVEIK | 55 |
|  | heavy chain variable region | QVQLVQSGAEVKKPGSSVKVSCKASGGTFSSYAIHWVR QAPGQGLEWMGWIVPGLGVTNYAQKFQGRVTITADEST STAYMELSSLRSEDTAVYYCARQATLYQTEYMDVWGQG TLVTVSS | 57 |
| 10 | light chain variable region | DIQMTQSPSSLSASVGDRVTITCRASQSISNYLNWYQQK PGKAPKLLIYAASNLQSGVPSRFSGSGSGTDFTLTISSLQ PEDFATYYCQQSYSFPFTFGQGTKVEIK | 67 |
|  | heavy chain variable region | QVQLVQSGAEVKKPGSSVKVSCKASGGTFSSHYMHWV RQAPGQGLEWMGWISPYLGSTNYAQKFQGRVTITADES TSTAYMELSSLRSEDTAVYYCARDETGSTYGAFDYWGQ GTLVTVSS | 69 |
| 11 | light chain variable region | DIQMTQSPSSLSASVGDRVTITCRASQSISNYLNWYQQK PGKAPKLLIYDASTLQSGVPSRFSGSGSGTDFTLTISSLQ PEDFATYYCQQSYSFPWTFGQGTKVEIK | 79 |
|  | heavy chain variable region | QVQLVQSGAEVKKPGSSVKVSCKASGGTFSSYYVHWVR QAPGQGLEWMGWISPYSGGTNYAQKFQGRVTITADEST STAYMELSSLRSEDTAVYYCARDYYVSAYGAFDYWGQG TLVTVSS | 81 |
| 12 | light chain variable region | DIQMTQSPSSLSASVGDRVTITCRASQDISNYLNWYQQK PGKAPKLLIYATSSLQSGVPSRFSGSGSGTDFTLTISSLQ PEDFATYYCQQSYSFPWTFGQGTKVEIK | 91 |
|  | heavy chain variable region | QVQLVQSGAEVKKPGSSVKVSCKASGGTFSSYDIHWVR QAPGQGLEWMGRIVPYLGVTNYAQKFQGRVTITADESTS TAYMELSSLRSEDTAVYYCARRQSQSSVYAFDIWGQGTL VTVSS | 93 |
| 13 | light chain variable region | DIQMTQSPSSLSASVGDRVTITCRASQSISNYLNWYQQK PGKAPKLLIYAASRLQSGVPSRFSGSGSGTDFTLTISSLQ PEDFATYYCQQSYSFPFTFGQGTKVEIK | 103 |
|  | heavy chain variable region | QVQLVQSGAEVKKPGSSVKVSCKASGGTFSGYYIHWVR QAPGQGLEWMGWISPSSGGTIYAQKFQGRVTITADESTS TAYMELSSLRSEDTAVYYCARDISVRVVQAFDYWGQGTL VTVSS | 105 |
| 14 | light chain variable region | DIQMTQSPSSLSASVGDRVTITCRASQSISNYLNWYQQK PGKAPKLLIYATSNLQSGVPSRFSGSGSGTDFTLTISSLQ PEDFATYYCQQSYSFPWTFGQGTKVEIK | 115 |
|  | heavy chain variable region | QVQLVQSGAEVKKPGSSVKVSCKASGGTFSSYYMHWV RQAPGQGLEWMGWISPYLGITNYAQKFQGRVTITADEST STAYMELSSLRSEDTAVYYCARAGYQQAQYWFDYWGQ GTLVTVSS | 117 |
| 15 | light chain variable region | DIQMTQSPSSLSASVGDRVTITCRASQSISNYLNWYQQK PGKAPKLLIYATSSLQSGVPSRFSGSGSGTDFTLTISSLQ PEDFATYYCQQSYSFPYTFGQGTKVEIK | 127 |
|  | heavy chain variable region | QVQLVQSGAEVKKPGSSVKVSCKASGGTFSSYAMSWV RQAPGQGLEWMGWIIPISGTTNYAQKFQGRVTITADEST STAYMELSSLRSEDTAVYYCARQHSVGSVFDYWGQGTL VTVSS | 129 |

TABLE 2-continued

| Clone | variable region | Amino acid sequence(N→C) | SEQ ID NO |
|-------|-----------------|--------------------------|-----------|
| 16 | light chain variable region | DIQMTQSPSSLSASVGDRVTITCRASQDISSWLNWYQQK PGKAPKLLIYAASSLQSGVPSRFSGSGSGTDFTLTISSLQ PEDFATYYCQQSYSFPWTFGQGTKVEIK | 139 |
| | heavy chain variable region | QVQLVQSGAEVKKPGSSVKVSCKASGGTFSSYYMTWV RQAPGQGLEWMGGISPILGVTNYAQKFQGRVTITADEST STAYMELSSLRSEDTAVYYCARLLVGVSETYFDYWGQGT LVTVSS | 141 |
| 17 | light chain variable region | DIQMTQSPSSLSASVGDRVTITCRASQSISNYLNWYQQK PGKAPKLLIYAASNMHSGVPSRFSGSGSGTDFTLTISSLQ PEDFATYYCQQSHSFPWTFGQGTKVEIK | 151 |
| | heavy chain variable region | QVQLVQSGAEVKKPGSSVKVSCKASGGTFSTYAMSWVR QAPGQGLEWMGGISPTLGIANYAQKFQGRVTITADESTS TAYMELSSLRSEDTAVYYCARVRYAGWTGYFDLWGQGT LVTVSS | 153 |
| 18 | light chain variable region | DIQMTQSPSSLSASVGDRVTITCRASQSISRWLNWYQQK PGKAPKLLIYAASRLQSGVPSRFSGSGSGTDFTLTISSLQ PEDFATYYCQQSESFPWTFGQGTKVEIK | 163 |
| | heavy chain variable region | QVQLVQSGAEVKKPGSSVKVSCKASGGTFSSYDINWVR QAPGQGLEWMGWIIPTSGSTNYAQKFQGRVTITADESTS TAYMELSSLRSEDTAVYYCARDSQSSYIGYFDVWGQGTL VTVSS | 165 |
| 19 | light chain variable region | DIQMTQSPSSLSASVGDRVTITCRASQSISNYLNWYQQK PGKAPKLLIYDTSSLQSGVPSRFSGSGSGTDFTLTISSLQ PEDFATYYCQQSYSTPYTFGQGTKVEIK | 175 |
| | heavy chain variable region | QVQLVQSGAEVKKPGSSVKVSCKASGGTFSAYGISWVR QAPGQGLEWMGRIIPYLGTANYAQKFQGRVTITADESTS TAYMELSSLRSEDTAVYYCARLSYGIGYESFDVWGQGTL VTVSS | 177 |
| 20 | light chain variable region | DIQMTQSPSSLSASVGDRVTITCRASQSISSYLNWYQQK PGKAPKLLIYDTSTLQSGVPSRFSGSGSGTDFTLTISSLQ PEDFATYYCQQSYSFPWTFGQGTKVEIK | 187 |
| | heavy chain variable region | QVQLVQSGAEVKKPGSSVKVSCKASGGTFSSYAMSWV RQAPGQGLEWMGSISSSGGSTYYADSVKGRVTITADES TSTAYMELSSLRSEDTAVYYCARELGGYGFSYFDYWGQ GTLVTVSS | 189 |
| 21 | light chain variable region | DIQMTQSPSSLSASVGDRVTITCRASQSIRNYLNWYQQK PGKAPKLLIYATSSLQSGVPSRFSGSGSGTDFTLTISSLQ PEDFATYYCQQSYSFPWTFGQGTKVEIK | 199 |
| | heavy chain variable region | QVQLVQSGAEVKKPGSSVKVSCKASGGTFSDYAMSWV RQAPGQGLEWMGGISGSDIYYADSVKGRVTITADESTST AYMELSSLRSEDTAVYYCARAVSYWSYTFDYWGQGTLV TVSS | 201 |
| 22 | light chain variable region | DIQMTQSPSSLSASVGDRVTITCRASQSIGSYLNWYQQK PGKAPKLLIYDASTLQSGVPSRFSGSGSGTDFTLTISSLQ PEDFATYYCQQSYSFPWTFGQGTKVEIK | 21 |
| | heavy chain variable region | QVQLVQSGAEVKKPGSSVKVSCKASGGTFSSYAMHWV RQAPGQGLEWMGGISSSGGTTYYADSVKGRVTITADES TSTAYMELSSLRSEDTAVYYCARALGVVGGTWFDYWGQ GTLVTVSS | 213 |
| 23 | light chain variable region | DIQMTQSPSSLSASVGDRVTITCRASQSISNYLNWYQQK PGKAPKLLIYDTSTLQSGVPSRFSGSGSGTDFTLTISSLQ PEDFATYYCQQSYSFPWTFGQGTKVEIK | 223 |
| | heavy chain variable region | QVQLVQSGAEVKKPGSSVKVSCKASGGTFSDYAMHWV RQAPGQGLEWMGAISGSGGYTHYADSVKGRVTITADES TSTAYMELSSLRSEDTAVYYCARSATFGVWETFDVWGQ GTLVTVSS | 225 |

In this disclosure, an antibody (for example, CDR, variable region, or heavy chain/light chain) "comprising a specific amino acid sequence or consisting of a specific amino acid sequence" refers to all cases which the amino acid sequence is essentially included, and/or an insignificant mutation (for example, substitution, deletion, and/or addition of amino acid residue(s)) that does not affect antibody activity is introduced into the amino acid sequence.

The anti-LILRB1 antibody or antigen-binding fragment thereof provided in this disclosure may have a binding affinity ($K_D$) to LILRB1 (for example, human LILRB1) of 10 mM or less, 5 mM or less, 1 mM or less, 0.5 mM or less, 0.2 mM or less, 0.15 mM or less, for example, 0.001 nM to 10 mM, 0.005 nM to 10 mM, 0.01 nM to 10 mM, 0.05 nM to 10 mM, 0.1 nM to 10 mM, 0.5 nM to 10 mM, 1 nM to 10 mM, 0.001 nM to 5 mM, 0.005 nM to 5 mM, 0.01 nM to 5 mM, 0.05 nM to 5 mM, 0.1 nM to 5 mM, 0.5 nM to 5 mM, 1 nM to 5 mM, 0.001 nM to 1 mM, 0.005 nM to 1 mM, 0.01 nM to 1 mM, 0.05 nM to 1 mM, 0.1 nM to 1 mM, 0.5 nM to 1 mM, 1 nM to 1 mM, 0.001 nM to 0.5 mM, 0.005 nM to 0.5 mM, 0.01 nM to 0.5 mM, 0.05 nM to 0.5 mM, 0.1 nM to 0.5 mM, 0.5 nM to 0.5 mM, 1 nM to 0.5 mM, 0.001 nM to 0.2 mM, 0.005 nM to 0.2 mM, 0.01 nM to 0.2 mM, 0.05 nM to 0.2 mM, 0.1 nM to 0.2 mM, 0.5 nM to 0.2 mM, 1 nM to 0.2 mM, 0.001 nM to 0.15 mM, 0.005 nM to 0.15 mM, 0.01 nM to 0.15 mM, 0.05 nM to 0.15 mM, 0.1 nM to 0.15 mM, 0.5 nM to 0.15 mM, or 1 nM to 0.15 mM, when measured by surface plasmon resonance (SPR).

Another embodiment provides a pharmaceutical composition comprising the anti-LILRB1 antibody or antigen-binding fragment thereof as an active ingredient. For example, the pharmaceutical composition may be a pharmaceutical composition for treating and/or preventing a cancer. In an embodiment, the pharmaceutical composition may have an activity to inhibit immune evasion of a cancer cell. The cancer cell may be a cell expressing or overexpressing MHC Class I on cell surface.

Another embodiment provides a method of treating and/or preventing a cancer, comprising administering (orally or parenterally) a pharmaceutically effective amount of the anti-LILRB1 antibody or antigen-binding fragment thereof to a subject (e.g., a mammal including human) in need of treating and/or preventing the cancer.

The methods provided in this disclosure may further comprise a step of identifying the subject in need of treating and/or preventing the cancer, and/or inhibiting immune evasion of the cancer cell, prior to the step of administering.

Another embodiment provides the use of the anti-LILRB1 antibody or antigen-binding fragment thereof for the treatment and/or prevention of cancer or for use in the manufacture of a pharmaceutical composition for the treatment and/or prevention of cancer. Another example provides the use of the anti-LILRB1 antibody or antigen-binding fragment thereof for inhibiting immune evasion of cancer cells or the use in the preparation of a pharmaceutical composition for inhibiting immune evasion of cancer cells.

Another embodiment provides a nucleic acid molecule encoding at least one polypeptide selected from the group consisting of CDR (CDR-L1, CDR-L2, CDR-L3, CDR-H1, CDR-H2, CDR-H3, a combination of CDR-L1, CDR-L2, and CDR-L3, or a combination of CDR-H1, CDR-H2, and CDR-H3), a light chain variable region comprising CDR-L1, CDR-L2, and CDR-L3, a heavy chain variable region comprising CDR-H1, CDR-H2, and CDR-H3; a light chain comprising the light chain variable region, and a heavy chain comprising the heavy chain variable region, of the anti-LILRB1 antibody described above.

Another embodiment provides a recombinant vector comprising the nucleic acid molecule. In an embodiment, the recombinant vector may include the light chain variable region or light chain, and the heavy chain variable region or heavy chain (e.g., in two separate vectors), respectively, or (e.g., in one vector) together. The recombinant vector may be an expression vector for expressing the light chain variable region or light chain and the heavy chain variable region or heavy chain in an appropriate cell.

Another embodiment provides a recombinant cell comprising the nucleic acid molecule or the recombinant vector.

Another embodiment provides a method for producing an anti-LILRB1 antibody or antigen-binding fragment thereof, comprising expressing the antibody in the recombinant cell.

As described herein, the antigen-binding fragment of an anti-LILRB1 antibody may refer to a fragment which is derived from an anti-LILRB1 antibody and retain antigen (LILRB1) binding affinity of the antibody. In an embodiment, the antigen-binding fragment may be a polypeptide comprising the 6 CDRs of an anti-LILRB1 antibody as described above, and, for example, may be scFv, scFv-Fc, scFv-Ck (kappa constant region), scFv-CA (lambda constant region), (scFv)$_2$, Fab, Fab', or a F(ab')$_2$, but not be limited thereto.

The anti-LILRB1 antibody or antigen-binding fragment thereof may have a regulatory activity, for example, an antagonistic or agonistic activity, on LILRB1 protein. In addition, the anti-LILRB1 antibody or antigen-binding fragment thereof may have an activity of inhibiting immune evasion of a cancer cell. Furthermore, the anti-LILRB1 antibody or antigen-binding fragment thereof may have an anti-cancer effect.

A protein LILRB1, which is an antigen of an anti-LILRB1 antibody or antigen-binding fragment thereof provided in this disclosure, may be derived from mammal. For example, LILRB1 as an antigen may be a human LILRB1 (e.g., GenBank accession numbers NP_001265328.2, NP_001265327.2, NP_001075108.2, NP_001075107.2, NP_001075106.2, NP_006660.4, NM_001081637.2, NM_001081638.3, NM_001081639.3, NM_001278398.2, NM_001278399.2, etc.), but not be limited thereto.

MHC Class I may be one of classes of major histocompatibility complex (MHC) molecules. In an embodiment, the MHC Class I may be a human MHC Class I and may be at least one selected from the group consisting of HLA (human leukocyte antigen)-A, HLA-B, HLA-C, HLA-E, HLA-F, and HLA-G, but not be limited thereto.

As described herein, the term "antibody" may refer to a protein that specifically binds to a specific antigen, and may be a protein produced by stimulation of an antigen in the immune system, or a protein produced by chemical synthesis or recombinant production, with no specific limitation. The antibody may be non-naturally occurring, for example, produced by recombinant or synthetic production. The antibody may be an animal antibody (e.g., a mouse antibody, etc.), a chimeric antibody, a humanized antibody, or a human antibody. The antibody may be a monoclonal or polyclonal antibody.

In the anti-LILRB1 antibody or antigen-binding fragment thereof provided herein, the portion, except for the heavy-chain CDR and light-chain CDR portions or the heavy-chain variable and light-chain variable regions as defined above, may be derived from any subtype of immunoglobulin (e.g., IgA, IgD, IgE, IgG (IgG1, IgG2, IgG3, IgG4), IgM, and the like), and, for example, derived from the framework portions, and/or light-chain constant region and/or heavy-chain constant region. In an embodiment, the anti-LILRB1 antibody provided in this disclosure may be an antibody in a form of human IgG, for example, IgG1, IgG2, IgG3, or IgG4, but not be limited thereto.

An intact antibody (e.g., IgG type) has a structure with two full-length light chains and two full-length heavy chains, in which each light chain is linked to a corresponding heavy chain via a disulfide bond. The constant region of an antibody is divided into a heavy-chain constant region and a light-chain constant region. The heavy-chain constant region is of a gamma (γ), mu (μ), alpha (α), delta (δ), or epsilon (ε) type, and has gamma1 (γ1), gamma2 (γ2), gamma3 (γ3), gamma4 (γ4), alpha1 (α1) or alpha2 (α2) as its subclass. The light chain constant region is of either a kappa (κ) or lambda (λ) type.

As used herein, the term "heavy chain" may be intended to encompass a full-length heavy chains and fragments thereof, wherein the full-length heavy chain may comprise a variable region VH including amino acid sequences sufficient to provide specificity to antigens, three constant regions CH1, CH2, and CH3, and a hinge. The term "light chain" may be intended to encompass full-length light chains and fragments thereof, wherein the full-length light chain may comprise a variable region VL including amino acid sequences sufficient to provide specificity to antigens, and a constant region CL.

The term "complementarity determining region (CDR)" may refer to a portion that confers antigen-binding specificity in a variable region of an antibody, and may refer to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contacting residues that play an important role in the binding of an antibody to its antigen or an epitope of the antigen. As used herein, the terms "specifically binding" and "specifically recognizing" may have the same general meaning as known to one of ordinary skill in the art, and indicate that an antibody and an antigen specifically interact with each other to lead to an immunological reaction.

In this disclosure, unless differently stated, the term "antibody" may encompass may be understood to include an antigen-binding fragment of an antibody having antigen-binding ability.

The term "antigen-binding fragment" used herein may refer to a polypeptide in any type, which comprises a portion (e.g., 6 CDRs as described herein) capable of binding to an antigen, and, for example, may be scFv, (scFv)$_2$, scFv-Fc, Fab, Fab', or F(ab')$_2$, but is not limited thereto. In addition, as described above, the antigen-binding fragment may be scFv, a fusion polypeptide wherein scFv is fused with a Fc region of an immunoglobulin (e.g., IgA, IgD, IgE, IgG (IgG1, IgG2, IgG3, IgG4), IgM, etc.) or a constant region (e.g., kappa or lambda).

Among the antigen-binding fragments, Fab has a structure having variable regions of light and heavy chains, a constant region of a light chain and a first constant region (CH1) of a heavy chain, and has one antigen-binding site.

Fab' is different from Fab in that Fab' comprises a hinge region having at least one cysteine residue at the C-terminal of CH1.

F(ab')$_2$ antibody is formed through disulfide bridging of the cysteine residues in the hinge region of Fab'.

Fv is a minimal antibody fragment composed of only a heavy chain variable region and a light chain variable region. Recombination techniques of generating an Fv fragment are widely known in the art.

Two-chain Fv comprises a heavy chain variable region and a light chain variable region which are linked to each other by a non-covalent bond. Single-chain Fv generally comprises a heavy-chain variable region and a light-chain variable region which are linked to each other by a covalent bond via a peptide linker or directly linked at the C-terminals to have a dimer structure like two-chain Fv.

The antigen-binding fragments may be obtained using protease (for example, Fab may be obtained by restrictively cleaving a whole antibody with papain, and an F(ab')$_2$ fragment may be obtained by cleaving with pepsin), or may be prepared by using a genetic recombination technique.

The term "hinge region" may refer to a region between CH1 and CH2 domains within heavy chain of an antibody, which functions to provide flexibility for the antigen-binding site in the antibody.

The anti-LILRB1 antibody may be a monoclonal or polyclonal antibody and, for example, a monoclonal antibody. A monoclonal antibody can be prepared using a method widely known in the art, for example, using a phage display technique. Alternatively, the anti-LILRB1 antibody may be constructed in the form of a mouse-derived monoclonal antibody by a conventional method.

Meanwhile, individual monoclonal antibodies can be screened using a typical ELISA (Enzyme-Linked Immu-noSorbent Assay) format, based on the binding potential against LILRB1. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to LILRB1 may be each verified.

The finally selected antibodies can be prepared and used as humanized antibodies as well as human immunoglobulin antibodies in which the remaining parts except for the antigen-binding portion are humanized. Methods for producing humanized antibodies are well known in the art.

The pharmaceutical composition may further comprise a pharmaceutically acceptable carrier, in addition to the active ingredient (the anti-LILRB1 antibody or antigen-binding fragment thereof). The pharmaceutically acceptable carrier may be anyone selected from those commonly used for the formulation of antibodies. For example, the pharmaceutically acceptable carrier may be one or more selected from the group consisting of lactose, dextrose, sucrose, sorbitol, mannitol, starch, gum acacia, calcium phosphate, alginates, gelatin, calcium silicate, micro-crystalline cellulose, poly-vinylpyrrolidone, cellulose, water, syrup, methyl cellulose, methylhydroxy benzoate, propylhydroxy benzoate, talc, magnesium stearate, mineral oil, and the like, but are not limited thereto. The pharmaceutical composition may further comprise one or more selected from the group consisting of a diluent, an excipient, a lubricant, a wetting agent, a sweetener, a flavor enhancer, an emulsifying agent, a suspension agent, preservative, and the like, which can be commonly used for manufacturing pharmaceutical composition.

The pharmaceutical composition, or the antibody or antigen-binding fragment thereof may be administered orally or parenterally in a pharmaceutically effective amount. The parenteral administration may be intravenous injection, subcutaneous injection, muscular injection, intraperitoneal injection, endothelial administration, intranasal administration, intrapulmonary administration, rectal administration or intralesional local administration. Since proteins or peptides are digested when administered orally, the active ingredient in the compositions for oral administration may be coated or formulated to prevent digestion in stomach. In addition, the antibody or the compositions may be administered using an optional device that enables the active ingredient to be delivered to target cells (e.g., cancer cells).

The content of the anti-LILRB1 antibody or antigen-binding fragment thereof or the dosage of the anti-LILRB1 antibody or antigen-binding fragment thereof in the pharmaceutical composition may be prescribed in a variety of ways, depending on various factors, such as the formulation method, administration method, age, weight, sex, pathology, food, administration time of the patient., administration interval, administration route, excretion rate, response sensitivity, etc. For example, anti-LILRB1 antibody or antigen-binding fragment thereof may be administered at the amount of 0.005 ug/kg to 1000 mg/kg, 0.005 ug/kg to 500 mg/kg, 0.005 ug/kg to 250 mg/kg, 0.005 ug/kg to 100 mg/kg, 0.005 ug/kg to 75 mg/kg, 0.005 ug/kg to 50 mg/kg, 0.01 ug/kg to 1000 mg/kg, 0.01 ug/kg to 500 mg/kg, 0.01 ug/kg to 250 mg/kg, 0.01 ug/kg to 100 mg/kg, 0.01 ug/kg to 75 mg/kg, 0.01 ug/kg to 50 mg/kg, 0.05 ug/kg to 1000 mg/kg, 0.05 ug/kg to 500 mg/kg, 0.05 ug/kg to 250 mg/kg, 0.05 ug/kg to 100 mg/kg, 0.05 ug/kg to 75 mg/kg, or 0.05 ug/kg to 50 mg/kg per day, but not be limited thereto. The daily dosage may be formulated into a single formulation in a unit dosage form or formulated in suitably divided dosage forms, or it may be manufactured to be contained in a multiple dosage container.

The pharmaceutical compositions may be formulated into a form of a solution in oil or an aqueous medium, a suspension, syrup, an emulsifying solution, an extract, powder, granules, a tablet, or a capsule, and may further comprise a dispersing or a stabilizing agent for the formulation.

The subject, to whom the antibody, pharmaceutical composition, or method provided in this disclosure is applied, may be selected from mammals including a mammal including primates such as humans and monkeys, rodents such as rats and mice, and the like.

The cancer may be a solid cancer or blood cancer. The cancer may be, but not limited to, one or more selected from the group consisting of lung cancer (e.g., squamous cell carcinoma of the lung, small-cell lung cancer, non-small-cell lung cancer, adenocarcinoma of the lung), peritoneal carcinoma, skin cancer, squamous cell carcinoma, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, leukemia (e.g., chronic or acute leukemia), lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, renal cell carcinoma, kidney cancer, prostate cancer, vulvar cancer, thyroid cancer, head and neck cancer, brain cancer, biliary tract cancer, gallbladder cancer, bone osteosarcoma, and the like. The cancer may be a primary cancer or a metastatic cancer. The cancer may be a cancer characterized by expression or overexpression of MHC Class I on a surface of cancer cell, and, for example, may be colon adenocarcinoma, small cell lung carcinoma, breast cancer, pancreatic cancer, malignant melanoma, bone osteosarcoma, renal cell carcinoma, or gastric cancer. The overexpression of MHC Class I may refer to an overexpression in cancer cells to which the antibody is applied as compared to normal cells. In one embodiment, the cancer may be a cancer that does not show anticancer effect (resistant) to T-cell mediated immunotherapy.

As used herein, the term "treatment of cancer" may refer to all anti-cancer actions that prevent, alleviate or ameliorate the symptoms of cancer, or partially or completely remove a cancer, such as, cancer cell death, inhibition of cancer cell proliferation, inhibition of cancer metastasis, and the like.

The anti-LILRB1 antibody or antigen-binding fragment thereof provided in this disclosure may be co-administered with another drug, for example, at least one selected from the group consisting of conventionally used agents for immunotherapy, anti-cancer agents, cytotoxic agents, and the like. Accordingly, an embodiment provides a pharmaceutical composition of combined administration for treating and/or preventing a cancer, comprising (1) an anti-LILRB1 antibody or antigen-binding fragment thereof, and (2) at least one selected from the group consisting of agents for immunotherapy, anti-cancer agents, cytotoxic agents, and the like. Another embodiment provides a method of treating and/or preventing a cancer, comprising administering (1) an anti-LILRB1 antibody or antigen-binding fragment thereof, and (2) at least one selected from the group consisting of agents for immunotherapy, anti-cancer agents, cytotoxic agents, and the like, to a subject in need of treating and/or preventing the cancer. The agents for immunotherapy, anti-cancer agents, and cytotoxic agents may include any drugs which are conventionally used for cancer therapy, and/or have cytotoxic activity, and for example, they may be at least one selected from the group consisting of proteins such as cell therapeutics, antibodies, nucleic acid molecules such as siRNA, and/or small molecular chemicals such as paclitaxel, docetaxel, and the like, but not limited thereto.

Another embodiment provides a polypeptide molecule comprising a heavy chain complementarity determining region (CDR-H1, CDR-H2, CDR-H3, or a combination thereof), a light chain complementarity determining region (CDR-L1, CDR-L2, CDR-L3, or a combination thereof), a combination thereof; or heavy chain variable region, light chain variable region, or a combination thereof, of the anti-LILRB1 antibody as described above. The polypeptide molecule may be used in preparing an antibody as a precursor of antibody, or comprised in a protein scaffold having an antibody-like structure (e.g., peptibody), a bispecific antibody, or a multispecific antibody, as a component thereof. In another embodiment, the polypeptide molecule comprising a heavy chain complementarity determining region (CDR-H1, CDR-H2, CDR-H3, or a combination thereof), a light chain complementarity determining region (CDR-L1, CDR-L2, CDR-L3, or a combination thereof), a combination thereof; or heavy chain variable region, light chain variable region, or a combination thereof, of the anti-LILRB1 antibody as described above may be used as a target (antigen) recognition domain or a secreted antibody, in cell therapeutics for target therapy, such as CAR-T. In another embodiment, the polypeptide molecule may be used for constructing anti-LILRB1 antibody-secreting cells as cell therapeutics.

Another embodiment provides a nucleic acid molecule encoding a heavy chain complementarity determining region (CDR-H1, CDR-H2, CDR-H3, or a combination thereof), a heavy chain variable region, or a heavy chain, of the anti-LILRB1 antibody.

Another embodiment provides a nucleic acid molecule encoding a light chain complementarity determining region (CDR-L1, CDR-L2, CDR-L3, or a combination thereof), a light chain variable region, or a light chain, of the anti-LILRB1 antibody.

Another embodiment provides a recombinant vector comprising a nucleic acid molecule encoding a heavy chain variable region or a heavy chain of the anti-LILRB1 antibody, and a light chain variable region or a light chain of the anti-LILRB1 antibody, respectively in two separate vectors or all together in one vector.

Another embodiment provides a recombinant cell comprising the recombinant vector.

The term "vector" refers to a means for expressing a target gene in a host cell, as exemplified by a plasmid vector, a cosmid vector, and a viral vector such as a bacteriophage vector, a lentivirus vector, an adenovirus vector, a retrovirus vector, and an adeno-associated virus vector. The recombinant vector may be constructed from or by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), a phage (for example, λgt4λB, λ-Charon, λΔz1, M13, etc.), or a virus vector (for example, SV40, etc.), which is commonly used in the art.

In the recombinant vector, the nucleic acid molecule may be operatively linked to a promoter. The term "operatively linked" is intended to pertain to a functional linkage between a nucleotide sequence of interest and an expression regulatory sequence (for example, a promoter sequence). When being "operatively linked", the regulatory element can control the transcription and/or translation of a polynucleotide of interest.

The recombinant vector may be constructed typically as a cloning vector or an expression vector. For recombinant expression vectors, a vector generally available in the relevant art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a $pL^\lambda$ promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host includes an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, tk promoter of HSV, etc.), and a polyadenylation sequence as a transcription termination sequence.

Another embodiment provides a recombinant cell comprising the recombinant vector.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure may be selected from E. coli such as E. coli JM109, E. coli BL21, E. coli RR1, E. coli LE392, E. coli B, E. coli X 1776, E. coli W3110, Bacillus spp. such as Bacillus subtilis and Bacillus thuringiensis, and enterobacteriaceae strains such as Salmonella typhimurium, Serratia marcescens and various Pseudomonas species. Eukaryotic host cells that may be used for transformation may selected from, but are not limited to, Saccharomyces cerevisiae, insect cells, and animal cells, such as Sp2/0, CHO (Chinese hamster ovary) K1, CHO DG44, CHO S, CHO DXB11, CHO GS-KO, PER.C6, W138, BHK, COS-7, 293, HepG2, Huh7, 3T3, RIN, MDCK, etc.

The nucleic acid molecule or a recombinant vector carrying the same may be introduced (transfected) into a host cell using a method well known in the relevant art. For example, this transfection may be carried out using a CaCl$_2$) or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of a phenotype associated with a selection marker according to methods well known in the art. For example, when the selection marker is a gene conferring resistance to a certain antibiotic, the host cells may be grown in the presence of the antibiotic in a medium to select a transformant of interest.

Another embodiment provides a method of preparing the anti-LILRB1 antibody or antigen-binding fragment thereof, comprising expressing the nucleic acid molecule or a recombinant vector in a host cell. The step of expressing may be conducted by culturing the recombinant cell comprising the nucleic acid molecule (for example, in a recombinant vector) under a condition allowing the expression of the nucleic acid molecule. The method may further comprise isolating and/or purifying the antibody or its fragment from the cell culture, after the step of expressing or culturing.

Advantageous Effects

The anti-LILRB1 antibody or antigen-binding fragment thereof provided in this disclosure can have high anti-cancer effect by inhibiting the immune evasion mechanism of cancer cells, allowing that the immune cells can exhibit their anti-cancer effect.

BRIEF DESCRIPTION OF DRAWINGS

FIG. 1 shows electrophoresis images showing the results of SDS-PAGE gel analysis for anti-LILRB1 antibodies purified in an example.

FIG. 2 is a sensorgram showing the results of SPR (surface plasmon resonance) assay for anti-LILRB1 antibody No. 13 according to an example.

FIG. 3 shows graphs showing the binding ability of anti-LILRB1 antibodies No. 8, No. 10, No. 11, No. 13, and No. 18 to LILRB1 overexpressing CHO cells according to an example.

FIG. 4 is a graph showing the IncuCyte S3-analyzed results of cell killing activity using HLA-G overexpressing HEK293 cells and natural killer cells KHYG-1, where those cells were treated with anti-LILRB1 antibodies (antibodies No. 10, No. 11 and No. 13) or human IgG4 isotype control antibody (negative control) according to an example.

FIG. 5 is a graph showing in vivo anti-tumor effects of anti-LILRB1 antibodies No. 10, No. 11, and No. 13 according to an example.

Hereinafter, the present invention will be described in detail by examples.

The following examples are intended merely to illustrate the invention and are not construed to restrict the invention.

EXAMPLE 1: PREPARATION OF HUMAN ANTIBODIES AGAINST LILRB1

1.1. Selection of Human Antibodies Against LILRB1 Using Phage Display

In order to select antibodies that specifically recognize human LILRB1, a phage display screening was performed using a library composed of human Fab antibodies. Phage panning was performed up to 4 rounds using human LILRB1-Fc (Cat. No. 2017-T2) (RnD systems) as an antigen. Additionally, since the antigen is in the form of Fc fusion, Fc control panning to remove the Fc binder in the panning step was also performed. The selected products were confirmed for their binding to the antigen through polyclonal phage ELISA.

1.2. Monoclonal Phage ELISA

Monoclonal phage ELISA was performed to select a clone that specifically binds to an antigen among the phage obtained through panning in Example 1.1. For the antigen of Example 1.1, an absorbance ($A_{450\ nm}$) cut-off of 0.4 or more was determined to confirm a positive clone, and the sequence of the corresponding gene was analyzed. In order to confirm the specificity of the antigen, the purified phage ELISA of the unique Fab clone for the antigen was performed to obtain the $EC_{50}$ (pfu) value.

1.3. Monoclonal Soluble Fab Analysis

Among the 47 unique clones that bind to the antigen obtained through panning in Example 1.2, genes encoding the Fab of the top 19 clones based on $EC_{50}$ in the phage specificity ELISA were amplified by PCR to produce expression vectors. After the antibody was expressed using TB media, soluble protein was obtained through periplasmic extraction. After purification through affinity chromatography, ELISA was performed to confirm binding to antigen.

EXAMPLE 2: CONVERSION OF SELECTED ANTIBODIES TO IGG

For the genes selected from the Fab-type phage display library in Example 1.3, genes corresponding to each heavy chain variable region (VH) and light chain variable region (VL) were amplified by PCR. In the case of some clones with low expression level, the genes of the light chain variable region (VL) were amplified in the same manner by PCR, and the gene sequences corresponding to the heavy chain variable region (VH) were generated by grafting CDRs into the sequence corresponding to the framework region (FR) of the clone with high expression level. The constructed heavy chain variable region (VH) and light chain variable region (VL) gene sequences were inserted into an expression vector (pCB-LIR-mAB, other than that, vectors including CMV promoter, or CMV/CHO beta-actin fusion promoter (KR10-1038126B1) and genes encoding human IgG4 heavy chain constant region and kappa light chain constant region can be used) designed to encode a human antibody in the form of IgG4 (IgG4 Fc: SEQ ID NO: 229, Kappa constant region: SEQ ID NO: 230). The DNA sequence of the prepared expression vector was confirmed through sequencing.

The amino acid sequences of CDR-L1, CDR-L2, CDR-L3, CDR-H1, CDR-H2, CDR-H3, light chain variable region, heavy chain variable region, light chain, and heavy chain of the 19 selected antibodies, and the nucleic acid sequences of the light chain variable region gene and the heavy chain variable region genes are shown in Tables 3 to 21 below. A clone number was assigned to each clone. Hereinafter, only simple clone numbers are indicated.

TABLE 3

| clone | region | Amino acid sequence (N→C) or Nucleic acid sequence (5'→3') | SEQ ID NO |
|---|---|---|---|
| 5 | CDR-L1 | RASQSIANYLN | 1 |
| | CDR-L2 | ATSTLQS | 2 |
| | CDR-L3 | QQSYSFPWT | 3 |
| | CDR-H1 | AYGIH | 4 |
| | CDR-H2 | WIIPLSGGAHYAQKFQG | 5 |
| | CDR-H3 | LYGWAEYFDV | 6 |
| | light chain variable region | DIQMTQSPSSLSASVGDRVTITCRASQSIANYLNWYQQKP GKAPKLLIYATSTLQSGVPSRFSGSGSGTDFTLTISSLQPE DFATYYCQQSYSFPWTFGQGTKVEIK | 7 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCGCAAATTACCTGAACTGGTATCAGCAGA AACCGGGCAAGGCGCCAAAATTGCTGATTTACGCAACT TCCACTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTGGACGTTCGGGCAGGGAACTAA AGTGGAAATTAAA | 8 |
| | heavy chain variable region | QVQLVQSGAEVKKPGSSVKVSCKASGGTFSAYGIHWVRQ APGQGLEWMGWIIPLSGGAHYAQKFQGRVTITADESTSTA YMELSSLRSEDTAVYYCARLYGWAEYFDVWGQGTLVTVS S | 9 |

TABLE 3-continued

| clone | region | Amino acid sequence (N→C) or Nucleic acid sequence (5'→3') | SEQ ID NO |
|---|---|---|---|
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTGCATACGGTATCCATTGGGTGCG GCAGGCGCCCGGCCAGGGTCTCGAATGGATGGGGTGG ATTATCCCACTGTCTGGTGGTGCACATTATGCACAAAAAT TCCAAGGCCGCGTAACTATTACCGCCGACGAATCAACCT CCACCGCCTACATGGAACTCAGCTCTCTGAGGTCAGAA GACACGGCCGTCTATTATTGCGCCAGACTGTACGGTTG GGCAGAATACTTCGATGTTTGGGGTCAGGGTACTCTGG TTACCGTCTCATCG | 10 |
| | light chain (Kappa) | DIQMTQSPSSLSASVGDRVTITCRASQSIANYLNWYQQKP GKAPKLLIYATSTLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 11 |
| | heavy chain | QVQLVQSGAEVKKPGSSVKVSCKASGGTFSAYGIHWVRQ APGQGLEWMGWIIPLSGGAHYAQKFQGRVTITADESTSTA YMELSSLRSEDTAVYYCARLYGWAEYFDVWGQGTLVTVS SASTKGPSVFPLAPCSRSTSESTAALGCLVKDYFPEPVTV SWNSGALTSGVHTFPAVLQSSGLYSLSSVVTVPSSSLGTK TYTCNVDHKPSNTKVDKRVESKYGPPCPPCPAPEAAGGP SVFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHY TQKSLSLSLG | 12 |

TABLE 4

| clone | region | Amino acid sequence (N→C) or Nucleic acid sequence (5'→3') | SEQ ID NO |
|---|---|---|---|
| 6 | CDR-L1 | RASQSISNYLN | 13 |
| | CDR-L2 | AASTLQS | 14 |
| | CDR-L3 | QQSYSFPWT | 15 |
| | CDR-H1 | SYTIS | 16 |
| | CDR-H2 | WISPELGTSNYAQKFQG | 17 |
| | CDR-H3 | LRYGQTLYGFDI | 18 |
| | light chain variable region | DIQMTQSPSSLSASVGDRVTITCRASQSISNYLNWYQQKP GKAPKLLIYAASTLQSGVPSRFSGSGSGTDFTLTISSLQPE DFATYYCQQSYSFPWTFGQGTKVEIK | 19 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCGGGCAAGGCGCCAAAATTGCTGATTTACGCAGCA TCCACTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTGGACGTTCGGGCAGGGAACTAA AGTGGAAATTAAA | 20 |
| | heavy chain variable region | QVQLVQSGAEVKKPGSSVKVSCKASGGTFSSYTISWVRQ APGQGLEWMGWISPELGTSNYAQKFQGRVTITADESTST AYMELSSLRSEDTAVYYCARLRYGQTLYGFDIWGQGTLVT VSS | 21 |
| | heavy chain variable region coding | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACACCATTTCTTGGGTGCGG CAGGCGCCCGGCCAGGGTCTCGAATGGATGGGGTGGA TTTCTCCAGAACTGGGTACCTCTAACTATGCACAAAAATT | 22 |

TABLE 4-continued

| clone | region | Amino acid sequence (N→C) or Nucleic acid sequence (5'→3') | SEQ ID NO |
|---|---|---|---|
| | gene | CCAAGGCCGCGTAACTATTACCGCCGACGAATCAACCT CCACCGCCTACATGGAACTCAGCTCTCTGAGGTCAGAA GACACGGCCGTCTATTATTGCGCCAGACTGCGTTACGG TCAGACTCTGTACGGTTTCGATATCTGGGGTCAGGGTAC TCTGGTTACCGTCTCATCG | |
| | light chain (Kappa) | DIQMTQSPSSLSASVGDRVTITCRASQSISNYLNWYQQKP GKAPKLLIYAASTLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 23 |
| | heavy chain | QVQLVQSGAEVKKPGSSVKVSCKASGGTFSSYTISWVRQ APGQGLEWMGWISPELGTSNYAQKFQGRVTITADESTST AYMELSSLRSEDTAVYYCARLRYGQTLYGFDIWGQGTLVT VSSASTKGPSVFPLAPCSRSTSESTAALGCLVKDYFPEPV TVSWNSGALTSGVHTFPAVLQSSGLYSLSSVVTVPSSSLG TKTYTCNVDHKPSNTKVDKRVESKYGPPCPPCPAPEAAG GPSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLG | 24 |

TABLE 5

| clone | region | Amino acid sequence (N→C) or Nucleic acid sequence (5'→3') | SEQ ID NO |
|---|---|---|---|
| 7 | CDR-L1 | RASQSISNWLN | 25 |
| | CDR-L2 | GTSSLQS | 26 |
| | CDR-L3 | QQSYSFPFT | 27 |
| | CDR-H1 | SYGMH | 28 |
| | CDR-H2 | WIIPVSGGATYAQKFQG | 29 |
| | CDR-H3 | GSWAYYAEFDY | 30 |
| | light chain variable region | DIQMTQSPSSLSASVGDRVTITCRASQSISNWLNWYQQK PGKAPKLLIYGTSSLQSGVPSRFSGSGSGTDFTLTISSLQP EDFATYYCQQSYSFPFTFGQGTKVEIK | 31 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTGGCTGAACTGGTATCAGCAGA AACCGGGCAAGGCGCCAAAATTGCTGATTTACGGTACTT CCTCTCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTTTTCCGTTTACGTTCGGGCAGGGAACTAAAG TGGAAATTAAA | 32 |
| | heavy chain variable region | QVQLVQSGAEVKKPGSSVKVSCKASGGTFSSYGMHWVR QAPGQGLEWMGWIIPVSGGATYAQKFQGRVTITADESTST AYMELSSLRSEDTAVYYCARGSWAYYAEFDYWGQGTLVT VSS | 33 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACGGTATGCATTGGGTGCG GCAGGCGCCCGGCCAGGGTCTCGAATGGATGGGGTGG ATTATCCCAGTTTCTGGTGGTGCAACCTATGCACAAAAAT TCCAAGGCCGCGTAACTATTACCGCCGACGAATCAACCT CCACCGCCTACATGGAACTCAGCTCTCTGAGGTCAGAA GACACGGCCGTCTATTATTGCGCCAGAGGTTCTTGGGC ATACTACGCTGAATTCGATTACTGGGGTCAGGGCACTTT AGTGACCGTCTCATCG | 34 |

TABLE 5-continued

| clone | region | Amino acid sequence (N→C) or Nucleic acid sequence (5'→3') | SEQ ID NO |
|---|---|---|---|
| | light chain (Kappa) | DIQMTQSPSSLSASVGDRVTITCRASQSISNWLNWYQQK PGKAPKLLIYGTSSLQSGVPSRFSGSGSGTDFTLTISSLQP EDFATYYCQQSYSFPFTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 35 |
| | heavy chain | QVQLVQSGAEVKKPGSSVKVSCKASGGTFSSYGMHWVR QAPGQGLEWMGWIIPVSGGATYAQKFQGRVTITADESTST AYMELSSLRSEDTAVYYCARGSWAYYAEFDYWGQGTLVT VSSASTKGPSVFPLAPCSRSTSESTAALGCLVKDYFPEPV TVSWNSGALTSGVHTFPAVLQSSGLYSLSSVVTVPSSSLG TKTYTCNVDHKPSNTKVDKRVESKYGPPCPPCPAPEAAG GPSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLG | 36 |

TABLE 6

| clone | region | Amino acid sequence (N→C) or Nucleic acid sequence (5'→3') | SEQ ID NO |
|---|---|---|---|
| 8 | CDR-L1 | RASQSISSYLN | 37 |
| | CDR-L2 | AASTLQS | 38 |
| | CDR-L3 | QQSYSFPYT | 39 |
| | CDR-H1 | SYGIH | 40 |
| | CDR-H2 | WIIPISGTTNYAQKFQG | 41 |
| | CDR-H3 | VGGVGLYVFDV | 42 |
| | light chain variable region | DIQMTQSPSSLSASVGDRVTITCRASQSISSYLNWYQQKP GKAPKLLIYAASTLQSGVPSRFSGSGSGTDFTLTISSLQPE DFATYYCQQSYSFPYTFGQGTKVEIK | 43 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTTCTTACCTGAACTGGTATCAGCAGA AACCGGGCAAGGCGCCAAAATTGCTGATTTACGCAGCA TCCACTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTACACGTTCGGGCAGGGAACTAA AGTGGAAATTAAA | 44 |
| | heavy chain variable region | QVQLVQSGAEVKKPGSSVKVSCKASGGTFSSYGIHWVRQ APGQGLEWMGWIIPISGTTNYAQKFQGRVTITADESTSTAY MELSSLRSEDTAVYYCARVGGVGLYVFDVWGQGTLVTVS S | 45 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACGGTATCCATTGGGTGCGG CAGGCGCCCGGCCAGGGTCTCGAATGGATGGGGTGGA TTATCCCAATCTCTGGTACCACCAACTATGCACAAAAATT CCAAGGCCGCGTAACTATTACCGCCGACGAATCAACCT CCACCGCCTACATGGAACTCAGCTCTCTGAGGTCAGAA GACACGGCCGTCTATTATTGCGCCAGAGTTGGTGGTGT TGGTCTGTACGTTTTCGATGTTTGGGGTCAGGGTACTCT GGTTACCGTCTCATCG | 46 |
| | light chain (Kappa) | DIQMTQSPSSLSASVGDRVTITCRASQSISSYLNWYQQKP GKAPKLLIYAASTLQSGVPSRFSGSGSGTDFTLTISSLQPE DFATYYCQQSYSFPYTFGQGTKVEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQGL SSPVTKSFNRGEC | 47 |

TABLE 6-continued

| clone region | Amino acid sequence (N→C) or Nucleic acid sequence (5'→3') | SEQ ID NO |
|---|---|---|
| heavy chain | QVQLVQSGAEVKKPGSSVKVSCKASGGTFSSYGIHWVRQ<br>APGQGLEWMGWIIPISGTTNYAQKFQGRVTITADESTSTAY<br>MELSSLRSEDTAVYYCARVGGVGLYVFDVWGQGTLVTVS<br>SASTKGPSVFPLAPCSRSTSESTAALGQLVKDYFPEPVTV<br>SWNSGALTSGVHTFPAVLQSSGLYSLSSVVTVPSSSLGTK<br>TYTCNVDHKPSNTKVDKRVESKYGPPCPPCPAPEAAGGP<br>SVFLFPPKPKDTLMISRTPEVTCVVVDVSQEDPEVQFNWY<br>VDGVEVHNAKTKPREEQFNSTYRVVSVLTVLHQDWLNGK<br>EYKCKVSNKGLPSSIEKTISKAKGQPREPQVYTLPPSQEE<br>MTKNQVSLTCLVKGFYPSDIAVEWESNGQPENNYKTTPPV<br>LDSDGSFFLYSRLTVDKSRWQEGNVFSCSVMHEALHNHY<br>TQKSLSLSLG | 48 |

TABLE 7

| cloneregion | | Amino acid sequence (N→C) or Nucleic acid sequence (5'→3') | SEQ ID NO |
|---|---|---|---|
| 9 | CDR-L1 | RASQSISNYLN | 49 |
| | CDR-L2 | AASSLQS | 50 |
| | CDR-L3 | QQSYSFPWT | 51 |
| | CDR-H1 | SYAIH | 52 |
| | CDR-H2 | WIVPGLGVTNYAQKFQG | 53 |
| | CDR-H3 | QATLYQTEYMDV | 54 |
| | light chain variable region | DIQMTQSPSSLSASVGDRVTITCRASQSISNYLNWYQQKP<br>GKAPKLLI-<br>YAASSLQSGVPSRFSGSGSGTDFTLTISSLQPE<br>DFATYYCQQSYSFPWTFGQGTKVEIK | 55 |
| | light chain variable region coding gene | GACATTCAAATGACGCAGAGTCCCTCCTCACTGAGTGC<br>TAGCGTGGGCGATCGTGTGACAATTACTTGTCGCGCTA<br>GCCAGTCTATCTCTAATTACCTGAACTGGTATCAGCAGA<br>AACCGGGCAAGGCGCCAAAATTGCTGATTTACGCCAGCA<br>TCCTCTCTGCAGTCTGGTGTACCGTCCCGTTTCTCTGG<br>CAGCGGTTCTGGTACGGATTTTACCCTGACCATCTCAAG<br>CCTCCAGCCTGAAGATTTTGCCACCTATTATTGTCAGCA<br>ATCTTACTCTTTTCCGTGGACGTTCGGGCAGGGAACTAA<br>AGTGGAAATTAAA | 56 |
| | heavy chain variable region | QVQLVQSGAEVKKPGSSVKVSCKASGGTFSSYAIHWVRQ<br>APGQGLEWMGWIVPGLGVTNYAQKFQGRVTITADESTST<br>AYMELSSLRSEDTAVYYCARQATLYQTEYMDVWGQGTLV<br>TVSS | 57 |
| | heavy chain variable region coding gene | CAAGTTCAGCTGGTCCAGAGCGGCGCAGAGGTGAAGA<br>AGCCCGGCAGTTCTGTTAAGGTTTCCTGCAAAGCCTCA<br>GGCGGGACTTTTAGTTCTTACGCAATCCATTGGGTGCG<br>GCAGGCGCCCGGCCAGGGTCTCGAATGGATGGGGTGG<br>ATTGTTCCAGGTCTGGGTGTTACCAACTATGCACAAAAA<br>TTCCAAGGCCGCGTAACTATTACCGCCGACGAATCAACC<br>TCCACCGCCTACATGGAACTCAGCTCTCTGAGGTCAGA<br>AGACACGGCCGTCTATTATTGCGCCAGACAGGCAACTC<br>TGTACCAGACTGAATACATGGATGTTTGGGGTCAGGGTA<br>CTCTGGTTACCGTCTCATCG | 58 |
| | light chain (Kappa) | DIQMTQSPSSLSASVGDRVTITCRASQSISNYLNWYQQKP<br>GKAPKLLI-<br>YAASSLQSGVPSRFSGSGSGTDFTLTISSLQPE<br>DFATYYCQQSYSFPWTFGQGTKVEIKRTVAAPSVFIFPPS<br>DEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC | 59 |
| | heavy chain | QVQLVQSGAEVKKPGSSVKVSCKASGGTFSSYAIHWVRQ<br>APGQGLEWMGWIVPGLGVTNYAQKFQGRVTITADESTST<br>AYMELSSLRSEDTAVYYCARQATLYQTEYMDVWGQGTLV | 60 |

TABLE 7-continued

| clone | region | Amino acid sequence (N→C) or Nucleic acid sequence (5'→3') | SEQ ID NO |
|---|---|---|---|
| | | TVSSASTKGPSVFPLAPCSRSTSESTAALGQLVKDYFPEP VTVSWNSGALTSGVHTFPAVLQSSGLYSLSSVVTVPSSSL GTKTYTCNVDHKPSNTKVDKRVESKYGPPCPPCPAPEAA GGPSVFLFPPKPKDTLMISRTPEVTCVVVDVSQEDPEVQF NWYVDGVEVHNAKTKPREEQFNSTYRVVSVLTVLHQDWL NGKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLG | |

TABLE 8

| clone | region | Amino acid sequence (N→C) or Nucleic acid sequence (5'→3') | SEQ ID NO |
|---|---|---|---|
| 10 | CDR-L1 | RASQSISNYLN | 61 |
| | CDR-L2 | AASNLQS | 62 |
| | CDR-L3 | QQSYSFPFT | 63 |
| | CDR-H1 | SHYMH | 64 |
| | CDR-H2 | WISPYLGSTNYAQKFQG | 65 |
| | CDR-H3 | DETGSTYGAFDY | 66 |
| | light chain variable region | DIQMTQSPSSLSASVGDRVTITCRASQSISNYLNWYQQKP GKAPKLLIYAASNLQSGVPSRFSGSGSGTDFTLTISSLQPE DFATYYCQQSYSFPFTFGQGTKVEIK | 67 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCGGGCAAGGCGCCAAAATTGCTGATTTACGCAGCA TCCAATCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTTTTCCGTTTACGTTCGGGCAGGGAACTAAAG TGGAAATTAAA | 68 |
| | heavy chain variable region | QVQLVQSGAEVKKPGSSVKVSCKASGGTFSSHYMHWVR QAPGQGLEWMGWISPYLGSTNYAQKFQGRVTITADESTS TAYMELSSLRSEDTAVYYCARDETGSTYGAFDYWGQGTL VTVSS | 69 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTCATTACATGCATTGGGTGCGG CAGGCGCCCGGCCAGGGTCTCGAATGGATGGGGTGGA TTTCTCCATACCTGGGGTTCTACCAACTATGCACAAAAATT CCAAGGCCGCGTAACTATTACCGCCGACGAATCAACCT CCACCGCCTACATGGAACTCAGCTCTCTGAGGTCAGAA GACACGGCCGTCTATTATTGCGCCAGAGATGAAACTGGT TCTACTTACGGTGCATTCGATTACTGGGGTCAGGGTACT CTGGTTACCGTCTCATCG | 70 |
| | light chain (Kappa) | DIQMTQSPSSLSASVGDRVTITCRASQSISNYLNWYQQKP GKAPKLLIYAASNLQSGVPSRFSGSGSGTDFTLTISSLQPE DFATYYCQQSYSFPFTFGQGTKVEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQGL SSPVTKSFNRGEC | 71 |
| | heavy chain | QVQLVQSGAEVKKPGSSVKVSCKASGGTFSSHYMHWVR QAPGQGLEWMGWISPYLGSTNYAQKFQGRVTITADESTS TAYMELSSLRSEDTAVYYCARDETGSTYGAFDYWGQGTL VTVSSASTKGPSVFPLAPCSRSTSESTAALGCLVKDYFPE PVTVSWNSGALTSGVHTFPAVLQSSGLYSLSSVVTVPSSS LGTKTYTCNVDHKPSNTKVDKRVESKYGPPCPPCPAPEA AGGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLPP | 72 |

TABLE 8-continued

| clone | region | Amino acid sequence (N→C) or Nucleic acid sequence (5'→3') | SEQ ID NO |
|---|---|---|---|
| | | SQEEMTKNQVSLTCLVKGFYPSDIAVEWESNGQPENNYK TTPPVLDSDGSFFLYSRLTVDKSRWQEGNVFSCSVMHEA LHNHYTQKSLSLSLG | |

TABLE 9

| clone | region | Amino acid sequence (N→C) or Nucleic acid sequence (5'→3') | SEQ ID NO |
|---|---|---|---|
| 11 | CDR-L1 | RASQSISNYLN | 73 |
| | CDR-L2 | DASTLQS | 74 |
| | CDR-L3 | QQSYSFPWT | 75 |
| | CDR-H1 | SYYVH | 76 |
| | CDR-H2 | WISPYSGGTNYAQKFQG | 77 |
| | CDR-H3 | DYYVSAYGAFDY | 78 |
| | light chain variable region | DIQMTQSPSSLSASVGDRVTITCRASQSISNYLNWYQQKP GKAPKLLIYDASTLQSGVPSRFSGSGSGTDFTLTISSLQPE DFATYYCQQSYSFPWTFGQGTKVEIK | 79 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCGGGCAAGGCGCCAAAATTGCTGATTTACGATGCAT CCACTCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTTTTCCGTGGACGTTCGGGCAGGGAACTAAA GTGGAAATTAAA | 80 |
| | heavy chain variable region | QVQLVQSGAEVKKPGSSVKVSCKASGGTFSSYYVHWVR QAPGQGLEWMGWISPYSGGTNYAQKFQGRVTITADESTS TAYMELSSLRSEDTAVYYCARDYYVSAYGAFDYWGQGTL VTVSS | 81 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACTACGTTCATTGGGTGCGG CAGGCGCCCGGCCAGGGTCTCGAATGGATGGGGTGGA TTTCTCCATACTCTGGTGGTACCAACTATGCACAAAAATT CCAAGGCCGCGTAACTATTACCGCCGACGAATCAACCT CCACCGCCTACATGGAACTCAGCTCTCTGAGGTCAGAA GACACGGCCGTCTATTATTGCGCCAGAGATTACTACGTT TCTGCATACGGTGCATTCGATTACTGGGGTCAGGGTACT CTGGTTACCGTCTCATCG | 82 |
| | light chain (Kappa) | DIQMTQSPSSLSASVGDRVTITCRASQSISNYLNWYQQKP GKAPKLLIYDASTLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 83 |
| | heavy chain | QVQLVQSGAEVKKPGSSVKVSCKASGGTFSSYYVHWVR QAPGQGLEWMGWISPYSGGTNYAQKFQGRVTITADESTS TAYMELSSLRSEDTAVYYCARDYYVSAYGAFDYWGQGTL VTVSSASTKGPSVFPLAPCSRSTSESTAALGQLVKDYFPE PVTVSWNSGALTSGVHTFPAVLQSSGLYSLSSVVTVPSSS LGTKTYTCNVDHKPSNTKVDKRVESKYGPPCPPCPAPEA AGGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLPP SQEEMTKNQVSLTCLVKGFYPSDIAVEWESNGQPENNYK TTPPVLDSDGSFFLYSRLTVDKSRWQEGNVFSCSVMHEA LHNHYTQKSLSLSLG | 84 |

TABLE 10

| clone | region | Amino acid sequence (N→C) or Nucleic acid sequence (5'→3') | SEQ ID NO |
|---|---|---|---|
| 12 | CDR-L1 | RASQDISNYLN | 85 |
| | CDR-L2 | ATSSLQS | 86 |
| | CDR-L3 | QQSYSFPWT | 87 |
| | CDR-H1 | SYDIH | 88 |
| | CDR-H2 | RIVPYLGVTNYAQKFQG | 89 |
| | CDR-H3 | RQSQSSVYAFDI | 90 |
| | light chain variable region | DIQMTQSPSSLSASVGDRVTITCRASQDISNYLNWYQQKP GKAPKLLIYATSSLQSGVPSRFSGSGSGTDFTLTISSLQPE DFATYYCQQSYSFPWTFGQGTKVEIK | 91 |
| | light chain variable region coding gene | GACATTCAAATGACGCAGAGTCCCTCCTCACTGAGTGC TAGCGTGGGCGATCGTGTGACAATTACTTGTCGCGCTA GCCAGGATATCTCTAATTACCTGAACTGGTATCAGCAGA AACCGGGCAAGGCGCCAAAATTGCTGATTTACGCAACT TCCTCTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTGGACGTTCGGGCAGGGAACTAA AGTGGAAATTAAA | 92 |
| | heavy chain variable region | QVQLVQSGAEVKKPGSSVKVSCKASGGTFSSYDIHWVRQ APGQGLEWMGRIVPYLGVTNYAQKFQGRVTITADESTSTA YMELSSLRSEDTAVYYCARRQSQSSVYAFDIWGQGTLVTV SS | 93 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACGATATCCATTGGGTGCGG CAGGCGCCCGGCCAGGGTCTCGAATGGATGGGGCGTA TTGTTCCATACCTGGGTGTTACCAACTATGCACAAAAATT CCAAGGCCGCGTAACTATTACCGCCGACGAATCAACCT CCACCGCCTACATGGAACTCAGCTCTCTGAGGTCAGAA GACACGGCCGTCTATTATTGCGCCAGACGTCAGTCTCA GTCTTCTGTTTACGCATTCGATATCTGGGGTCAGGGCAC TTTAGTGACCGTCTCATCG | 94 |
| | light chain (Kappa) | DIQMTQSPSSLSASVGDRVTITCRASQDISNYLNWYQQKP GKAPKLLIYATSSLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 95 |
| | heavy chain | QVQLVQSGAEVKKPGSSVKVSCKASGGTFSSYDIHWVRQ APGQGLEWMGRIVPYLGVTNYAQKFQGRVTITADESTSTA YMELSSLRSEDTAVYYCARRQSQSSVYAFDIWGQGTLVTV SSASTKGPSVFPLAPCSRSTSESTAALGCLVKDYFPEPVT VSWNSGALTSGVHTFPAVLQSSGLYSLSSVVTVPSSSLGT KTYTCNVDHKPSNTKVDKRVESKYGPPCPPCPAPEAAGG PSVFLFPPKPKDTLMISRTPEVTCVVVDVSQEDPEVQFNW YVDGVEVHNAKTKPREEQFNSTYRVVSVLTVLHQDWLNG KEYKCKVSNKGLPSSIEKTISKAKGQPREPQVYTLPPSQE EMTKNQVSLTCLVKGFYPSDIAVEWESNGQPENNYKTTPP VLDSDGSFFLYSRLTVDKSRWQEGNVFSCSVMHEALHNH YTQKSLSLSLG | 96 |

TABLE 11

| clone | region | Amino acid sequence (N→C) or Nucleic acid sequence (5'→3') | SEQ ID NO |
|---|---|---|---|
| 13 | CDR-L1 | RASQSISNYLN | 97 |
| | CDR-L2 | AASRLQS | 98 |
| | CDR-L3 | QQSYSFPFT | 99 |

TABLE 11-continued

| clone | region | Amino acid sequence (N→C) or Nucleic acid sequence (5'→3') | SEQ ID NO |
|---|---|---|---|
| | CDR-H1 | GYYIH | 100 |
| | CDR-H2 | WISPSSGGTIYAQKFQG | 101 |
| | CDR-H3 | DISVRVVQAFDY | 102 |
| | light chain variable region | DIQMTQSPSSLSASVGDRVTITCRASQSISNYLNWYQQKP GKAPKLLIYAASRLQSGVPSRFSGSGSGTDFTLTISSLQP EDFATYYCQQSYSFPFTFGQGTKVEIK | 103 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCGGGCAAGGCGCCAAAATTGCTGATTTACGCAGCA TCCCGTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTTTACGTTCGGGCAGGGAACTAA AGTGGAAATTAAA | 104 |
| | heavy chain variable region | QVQLVQSGAEVKKPGSSVKVSCKASGGTFSGYYIHWVRQ APGQGLEWMGWISPSSGGTIYAQKFQGRVTITADESTSTA YMELSSLRSEDTAVYYCARDISVRVVQAFDYWGQGTLVTV SS | 105 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTGGTTACTACATCCATTGGGTGCG GCAGGCGCCCGGCCAGGGTCTCGAATGGATGGGGTGG ATTTCTCCATCTTCTGGTGGTACCATCTATGCACAAAAAT TCCAAGGCCGCGTAACTATTACCGCCGACGAATCAACCT CCACCGCCTACATGGAACTCAGCTCTCTGAGGTCAGAA GACACGGCCGTCTATTATTGCGCCAGAGATATCTCTGTT CGTGTTGTTCAGGCATTCGATTACTGGGGTCAGGGTACT CTGGTTACCGTCTCATCG | 106 |
| | light chain (Kappa) | DIQMTQSPSSLSASVGDRVTITCRASQSISNYLNWYQQKP GKAPKLLIYAASRLQSGVPSRFSGSGSGTDFTLTISSLQPE DFATYYCQQSYSFPFTFGQGTKVEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQGL SSPVTKSFNRGEC | 107 |
| | heavy chain | QVQLVQSGAEVKKPGSSVKVSCKASGGTFSGYYIHWVRQ APGQGLEWMGWISPSSGGTIYAQKFQGRVTITADESTSTA YMELSSLRSEDTAVYYCARDISVRVVQAFDYWGQGTLVTV SSASTKGPSVFPLAPCSRSTSESTAALGCLVKDYFPEPVT VSWNSGALTSGVHTFPAVLQSSGLYSLSSVVTVPSSSLGT KTYTCNVDHKPSNTKVDKRVESKYGPPCPPCPAPEAAGG PSVFLFPPKPKDTLMISRTPEVTCVVVDVSQEDPEVQFNW YVDGVEVHNAKTKPREEQFNSTYRVVSVLTVLHQDWLNG KEYKCKVSNKGLPSSIEKTISKAKGQPREPQVYTLPPSQE EMTKNQVSLTCLVKGFYPSDIAVEWESNGQPENNYKTTPP VLDSDGSFFLYSRLTVDKSRWQEGNVFSCSVMHEALHNH YTQKSLSLSLG | 108 |

TABLE 12

| clone | region | Amino acid sequence (N→C) or Nucleic acid sequence (5'→3') | SEQ ID NO |
|---|---|---|---|
| 14 | CDR-L1 | RASQSISNYLN | 109 |
| | CDR-L2 | ATSNLQS | 110 |
| | CDR-L3 | QQSYSFPWT | 111 |
| | CDR-H1 | SYYMH | 112 |
| | CDR-H2 | WISPYLGITNYAQKFQG | 113 |

TABLE 12-continued

| clone | region | Amino acid sequence (N→C) or Nucleic acid sequence (5'→3') | SEQ ID NO |
|---|---|---|---|
| | CDR-H3 | AGYQQAQYWFDY | 114 |
| | light chain variable region | DIQMTQSPSSLSASVGDRVTITCRASQSISNYLNWYQQKP GKAPKLLIYATSNLQSGVPSRFSGSGSGTDFTLTISSLQPE DFATYYCQQSYSFPWTFGQGTKVEIK | 115 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCGGGCAAGGCGCCAAAATTGCTGATTTACGCAACT TCCAATCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTTTTCCGTGGACGTTCGGGCAGGGAACTAAA GTGGAAATTAAA | 116 |
| | heavy chain variable region | QVQLVQSGAEVKKPGSSVKVSCKASGGTFSSYYMHWVR QAPGQGLEWMGWISPYLGITNYAQKFQGRVTITADESTST AYMELSSLRSEDTAVYYCARAGYQQAQYWFDYWGQGTL VTVSS | 117 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACTACATGCATTGGGTGCGG CAGGCGCCCGGCCAGGGTCTCGAATGGATGGGGTGGA TTTCTCCATACCTGGGTATCACCAACTATGCACAAAAATT CCAAGGCCGCGTAACTATTACCGCCGACGAATCAACCT CCACCGCCTACATGGAACTCAGCTCTCTGAGGTCAGAA GACACGGCCGTCTATTATTGCGCCAGAGCAGGTTACCA GCAGGCACAGTACTGGTTCGATTACTGGGGTCAGGGCA CTTTAGTGACCGTCTCATCG | 118 |
| | light chain (Kappa) | DIQMTQSPSSLSASVGDRVTITCRASQSISNYLNWYQQKP GKAPKLLIYATSNLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 119 |
| | heavy chain | QVQLVQSGAEVKKPGSSVKVSCKASGGTFSSYYMHWVR QAPGQGLEWMGWISPYLGITNYAQKFQGRVTITADESTST AYMELSSLRSEDTAVYYCARAGYQQAQYWFDYWGQGTL VTVSSASTKGPSVFPLAPCSRSTSESTAALGQLVKDYFPE PVTVSWNSGALTSGVHTFPAVLQSSGLYSLSSVVTVPSSS LGTKTYTCNVDHKPSNTKVDKRVESKYGPPCPPCPAPEA AGGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLPP SQEEMTKNQVSLTCLVKGFYPSDIAVEWESNGQPENNYK TTPPVLDSDGSFFLYSRLTVDKSRWQEGNVFSCSVMHEA LHNHYTQKSLSLSLG | 120 |

TABLE 13

| clone | region | Amino acid sequence (N→C) or Nucleic acid sequence (5'→3') | SEQ ID NO |
|---|---|---|---|
| 15 | CDR-L1 | RASQSISNYLN | 121 |
| | CDR-L2 | ATSSLQS | 122 |
| | CDR-L3 | QQSYSFPYT | 123 |
| | CDR-H1 | SYAMS | 124 |
| | CDR-H2 | WIIPISGTTNYAQKFQG | 125 |
| | CDR-H3 | QHSVGSVFDY | 126 |

TABLE 13-continued

| clone | region | Amino acid sequence (N→C) or Nucleic acid sequence (5'→3') | SEQ ID NO |
|---|---|---|---|
| | light chain variable region | DIQMTQSPSSLSASVGDRVTITCRASQSISNYLNWYQQKP GKAPKLLIYATSSLQSGVPSRFSGSGSGTDFTLTISSLQPE DFATYYCQQSYSFPYTFGQGTKVEIK | 127 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCGGGCAAGGCGCCAAAATTGCTGATTTACGCAACT TCCTCTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTACACGTTCGGGCAGGGAACTAA AGTGGAAATTAAA | 128 |
| | heavy chain variable region | QVQLVQSGAEVKKPGSSVKVSCKASGGTFSSYAMSWVR QAPGQGLEWMGWIIPISGTTNYAQKFQGRVTITADESTST AYMELSSLRSEDTAVYYCARQHSVGSVFDYWGQGTLVTV SS | 129 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACGCAATGTCTTGGGTGCG GCAGGCGCCCGGCCAGGGTCTCGAATGGATGGGGTGG ATTATCCCAATCTCTGGTACCACCAACTATGCACAAAAT TCCAAGGCCGCGTAACTATTACCGCCGACGAATCAACCT CCACCGCCTACATGGAACTCAGCTCTCTGAGGTCAGAA GACACGGCCGTCTATTATTGCGCCAGACAGCATTCTGTT GGTTCTGTTTTCGATTACTGGGGTCAGGGTACTCTGGTT ACCGTCTCATCG | 130 |
| | light chain (Kappa) | DIQMTQSPSSLSASVGDRVTITCRASQSISNYLNWYQQKP GKAPKLLIYATSSLQSGVPSRFSGSGSGTDFTLTISSLQPE DFATYYCQQSYSFPYTFGQGTKVEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQGL SSPVTKSFNRGEC | 131 |
| | heavy chain | QVQLVQSGAEVKKPGSSVKVSCKASGGTFSSYAMSWVR QAPGQGLEWMGWIIPISGTTNYAQKFQGRVTITADESTST AYMELSSLRSEDTAVYYCARQHSVGSVFDYWGQGTLVTV SSASTKGPSVFPLAPCSRSTSESTAALGCLVKDYFPEPVT VSWNSGALTSGVHTFPAVLQSSGLYSLSSVVTVPSSSLGT KTYTCNVDHKPSNTKVDKRVESKYGPPCPPCPAPEAAGG PSVFLFPPKPKDTLMISRTPEVTCVVVDVSQEDPEVQFNW YVDGVEVHNAKTKPREEQFNSTYRVVSVLTVLHQDWLNG KEYKCKVSNKGLPSSIEKTISKAKGQPREPQVYTLPPSQE EMTKNQVSLTCLVKGFYPSDIAVEWESNGQPENNYKTTPP VLDSDGSFFLYSRLTVDKSRWQEGNVFSCSVMHEALHNH YTQKSLSLSLG | 132 |

TABLE 14

| clone | region | Amino acid sequence (N→C) or Nucleic acid sequence (5'→3') | SEQ ID NO |
|---|---|---|---|
| 16 | CDR-L1 | RASQDISSWLN | 133 |
| | CDR-L2 | AASSLQS | 134 |
| | CDR-L3 | QQSYSFPWT | 135 |
| | CDR-H1 | SYYMT | 136 |
| | CDR-H2 | GISPILGVTNYAQKFQG | 137 |
| | CDR-H3 | LLVGVSETYFDY | 138 |
| | light chain variable region | DIQMTQSPSSLSASVGDRVTITCRASQDISSWLNWYQQK PGKAPKLLIYAASSLQSGVPSRFSGSGSGTDFTLTISSLQP EDFATYYCQQSYSFPWTFGQGTKVEIK | 139 |

TABLE 14-continued

| clone | region | Amino acid sequence (N→C) or Nucleic acid sequence (5'→3') | SEQ ID NO |
|---|---|---|---|
| | light chain variable region coding gene | GACATTCAAATGACGCAGAGTCCCTCCTCACTGAGTGC TAGCGTGGGCGATCGTGTGACAATTACTTGTCGCGCTA GCCAGGATATCTCTTCTTGGCTGAACTGGTATCAGCAGA AACCGGGCAAGGCGCCAAAATTGCTGATTTACGCAGCA TCCTCTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTGGACGTTCGGGCAGGGAACTAA AGTGGAAATTAAA | 140 |
| | heavy chain variable region | QVQLVQSGAEVKKPGSSVKVSCKASGGTFSSYYMTWVR QAPGQGLEWMGGISPILGVTNYAQKFQGRVTITADESTST AYMELSSLRSEDTAVYYCARLLVGVSETYFDYWGQGTLVT VSS | 141 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACTACATGACCTGGGTGCG GCAGGCGCCCGGCCAGGGTCTCGAATGGATGGGGGGT ATTTCTCCAATCCTGGGTGTTACCAACTATGCACAAAAAT TCCAAGGCCGCGTAACTATTACCGCCGACGAATCAACCT CCACCGCCTACATGGAACTCAGCTCTCTGAGGTCAGAA GACACGGCCGTCTATTATTGCGCCAGACTGCTGGTTGG TGTTTCTGAAACTTACTTCGATTACTGGGGTCAGGGTAC TCTGGTTACCGTCTCATCG | 142 |
| | light chain (Kappa) | DIQMTQSPSSLSASVGDRVTITCRASQDISSWLNWYQQK PGKAPKLLIYAASSLQSGVPSRFSGSGSGTDFTLTISSLQP EDFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 143 |
| | heavy chain | QVQLVQSGAEVKKPGSSVKVSCKASGGTFSSYYMTWVR QAPGQGLEWMGGISPILGVTNYAQKFQGRVTITADESTST AYMELSSLRSEDTAVYYCARLLVGVSETYFDYWGQGTLVT VSSASTKGPSVFPLAPCSRSTSESTAALGCLVKDYFPEPV TVSWNSGALTSGVHTFPAVLQSSGLYSLSSVVTVPSSSLG TKTYTCNVDHKPSNTKVDKRVESKYGPPCPPCPAPEAAG GPSVFLFPPKPKDTLMISRTPEVTCVVVDVSQEDPEVQFN WYVDGVEVHNAKTKPREEQFNSTYRVVSVLTVLHQDWLN GKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHN HYTQKSLSLSLG | 144 |

TABLE 15

| clone | region | Amino acid sequence (N→C) or Nucleic acid sequence (5'→3') | SEQ ID NO |
|---|---|---|---|
| 17 | CDR-L1 | RASQSISNYLN | 145 |
| | CDR-L2 | AASNMHS | 146 |
| | CDR-L3 | QQSHSFPWT | 147 |
| | CDR-H1 | TYAMS | 148 |
| | CDR-H2 | GISPTLGIANYAQKFQG | 149 |
| | CDR-H3 | VRYAGWTGYFDL | 150 |
| | light chain variable region | DIQMTQSPSSLSASVGDRVTITCRASQSISNYLNWYQQKP GKAPKLLIYAASNMHSGVPSRFSGSGSGTDFTLTISSLQPE DFATYYCQQSHSFPWTFGQGTKVEIK | 151 |
| | light chain variable | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA | 152 |

TABLE 15-continued

| clone | region | Amino acid sequence (N→C) or Nucleic acid sequence (5'→3') | SEQ ID NO |
|-------|--------|------------------------------------------------------------|-----------|
| | region coding gene | AACCGGGCAAGGCGCCAAAATTGCTGATTTACGCAGCA TCCAATATGCACTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTCACTCTTTTCCGTGGACGTTCGGGCAGGGAACTAAA GTGGAAATTAAA | |
| | heavy chain variable region | QVQLVQSGAEVKKPGSSVKVSCKASGGTFSTYAMSWVR QAPGQGLEWMGGISPTLGIANYAQKFQGRVTITADESTST AYMELSSLRSEDTAVYYCARVRYAGWTGYFDLWGQGTLV TVSS | 153 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTACCTACGCAATGTCTTGGGTGCG GCAGGCGCCCGGCCAGGGTCTCGAATGGATGGGGGGT ATTTCTCCAACCCTGGGTATCGCAAACTATGCACAAAAT TCCAAGGCCGCGTAACTATTACCGCCGACGAATCAACCT CCACCGCCTACATGGAACTCAGCTCTCTGAGGTCAGAA GACACGGCCGTCTATTATTGCGCCAGAGTTCGTTACGCA GGTTGGACTGGTTACTTCGATCTGTGGGGTCAGGGTAC TCTGGTTACCGTCTCATCG | 154 |
| | light chain (Kappa) | DIQMTQSPSSLSASVGDRVTITCRASQSISNYLNWYQQKP GKAPKLLIYAASNMHSGVPSRFSGSGSGTDFTLTISSLQPE DFATYYCQQSHSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 155 |
| | heavy chain | QVQLVQSGAEVKKPGSSVKVSCKASGGTFSTYAMSWVR QAPGQGLEWMGGISPTLGIANYAQKFQGRVTITADESTST AYMELSSLRSEDTAVYYCARVRYAGWTGYFDLWGQGTLV TVSSASTKGPSVFPLAPCSRSTSESTAALGCLVKDYFPEP VTVSWNSGALTSGVHTFPAVLQSSGLYSLSSVVTVPSSSL GTKTYTCNVDHKPSNTKVDKRVESKYGPPCPPCPAPEAA GGPSVFLFPPKPKDTLMISRTPEVTCVVVDVSQEDPEVQF NWYVDGVEVHNAKTKPREEQFNSTYRVVSVLTVLHQDWL NGKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLG | 156 |

TABLE 16

| clone | region | Amino acid sequence (N→C) or Nucleic acid sequence (5'→3') | SEQ ID NO |
|-------|--------|------------------------------------------------------------|-----------|
| 18 | CDR-L1 | RASQSISRWLN | 157 |
| | CDR-L2 | AASRLQS | 158 |
| | CDR-L3 | QQSESFPWT | 159 |
| | CDR-H1 | SYDIN | 160 |
| | CDR-H2 | WIIPTSGSTNYAQKFQG | 161 |
| | CDR-H3 | DSQSSYIGYFDV | 162 |
| | light chain variable region | DIQMTQSPSSLSASVGDRVTITCRASQSISRWLNWYQQKP GKAPKLLIYAASRLQSGVPSRFSGSGSGTDFTLTISSLQPE DFATYYCQQSESFPWTFGQGTKVEIK | 163 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTCGTTGGCTGAACTGGTATCAGCAGA AACCGGGCAAGGCGCCAAAATTGCTGATTTACGCAGCA TCCCGTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA | 164 |

TABLE 16-continued

| clone | region | Amino acid sequence (N→C) or Nucleic acid sequence (5'→3') | SEQ ID NO |
|---|---|---|---|
| | | ATCTGAATCTTTTCCGTGGACGTTCGGGCAGGGAACTAA AGTGGAAATTAAA | |
| | heavy chain variable region | QVQLVQSGAEVKKPGSSVKVSCKASGGTFSSYDINWVRQ APGQGLEWMGWIIPTSGSTNYAQKFQGRVTITADESTSTA YMELSSLRSEDTAVYYCARDSQSSYIGYFDVWGQGTLVTV SS | 165 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTACGATATCAACTGGGTGCGG CAGGCGCCCGGCCAGGGTCTCGAATGGATGGGGTGGA TTATCCCAACCTCTGGTTCTACCAACTATGCACAAAATT CCAAGGCCGCGTAACTATTACCGCCGACGAATCAACCT CCACCGCCTACATGGAACTCAGCTCTCTGAGGTCAGAA GACACGGCCGTCTATTATTGCGCCAGAGATTCTCAGTCT TCTTACATCGGTTACTTCGATGTTTGGGGTCAGGGTACT CTGGTTACCGTCTCATCG | 166 |
| | light chain (Kappa) | DIQMTQSPSSLSASVGDRVTITCRASQSISRWLNWYQQKP GKAPKLLIYAASRLQSGVPSRFSGSGSGTDFTLTISSLQPE DFATYYCQQSESFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 167 |
| | heavy chain | QVQLVQSGAEVKKPGSSVKVSCKASGGTFSSYDINWVRQ APGQGLEWMGWIIPTSGSTNYAQKFQGRVTITADESTSTA YMELSSLRSEDTAVYYCARDSQSSYIGYFDVWGQGTLVTV SSASTKGPSVFPLAPCSRSTSESTAALGCLVKDYFPEPVT VSWNSGALTSGVHTFPAVLQSSGLYSLSSVVTVPSSSLGT KTYTCNVDHKPSNTKVDKRVESKYGPPCPPCPAPEAAGG PSVFLFPPKPKDTLMISRTPEVTCVVVDVSQEDPEVQFNW YVDGVEVHNAKTKPREEQFNSTYRVVSVLTVLHQDWLNG KEYKCKVSNKGLPSSIEKTISKAKGQPREPQVYTLPPSQE EMTKNQVSLTCLVKGFYPSDIAVEWESNGQPENNYKTTPP VLDSDGSFFLYSRLTVDKSRWQEGNVFSCSVMHEALHNH YTQKSLSLSLG | 168 |

TABLE 17

| clone | region | Amino acid sequence (N→C) or Nucleic acid sequence (5'→3') | SEQ ID NO |
|---|---|---|---|
| 19 | CDR-L1 | RASQSISNYLN | 169 |
| | CDR-L2 | DTSSLQS | 170 |
| | CDR-L3 | QQSYSTPYT | 171 |
| | CDR-H1 | AYGIS | 172 |
| | CDR-H2 | RIIPYLGTANYAQKFQG | 173 |
| | CDR-H3 | LSYGIGYESFDV | 174 |
| | light chain variable region | DIQMTQSPSSLSASVGDRVTITCRASQSISNYLNWYQQKP GKAPKLLIYDTSSLQSGVPSRFSGSGSGTDFTLTISSLQP EDFATYYCQQSYSTPYTFGQGTKVEIK | 175 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCGGGCAAGGCGCCAAAATTGCTGATTTACGATACTT CCTCTCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTACTCCGTACACGTTCGGGCAGGGAACTAAAG TGGAAATTAAA | 176 |

TABLE 17-continued

| clone | region | Amino acid sequence (N→C) or Nucleic acid sequence (5'→3') | SEQ ID NO |
|---|---|---|---|
| | heavy chain variable region | QVQLVQSGAEVKKPGSSVKVSCKASGGTFSAYGISWVRQ APGQGLEWMGRIIPYLGTANYAQKFQGRVTITADESTSTAY MELSSLRSEDTAVYYCARLSYGIGYESFDVWGQGTLVTVS S | 177 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTGCATACGGTATCTCTTGGGTGCG GCAGGCGCCCGGCCAGGGTCTCGAATGGATGGGGCGT ATTATCCCATACCTGGGTACCGCAAACTATGCACAAAAAT TCCAAGGCCGCGTAACTATTACCGCCGACGAATCAACCT CCACCGCCTACATGGAACTCAGCTCTCTGAGGTCAGAA GACACGGCCGTCTATTATTGCGCCAGACTGTCTTACGGT ATCGGTTACGAATCTTTCGATGTTTGGGGTCAGGGCACT TTAGTGACCGTCTCATCG | 178 |
| | light chain (Kappa) | DIQMTQSPSSLSASVGDRVTITCRASQSISNYLNWYQQKP GKAPKLLIYDTSSLQSGVPSRFSGSGSGTDFTLTISSLQPE DFATYYCQQSYSTPYTFGQGTKVEIKRTVAAPSVFIFPPSD EQLKSGTASVVCLLNNFYPREAKVQWKVDNALQSGNSQE SVTEQDSKDSTYSLSSTLTLSKADYEKHKVYACEVTHQGL SSPVTKSFNRGEC | 179 |
| | heavy chain | QVQLVQSGAEVKKPGSSVKVSCKASGGTFSAYGISWVRQ APGQGLEWMGRIIPYLGTANYAQKFQGRVTITADESTSTAY MELSSLRSEDTAVYYCARLSYGIGYESFDVWGQGTLVTVS SASTKGPSVFPLAPCSRSTSESTAALGQLVKDYFPEPVTV SWNSGALTSGVHTFPAVLQSSGLYSLSSVVTVPSSSLGTK TYTCNVDHKPSNTKVDKRVESKYGPPCPPCPAPEAAGGP SVFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHY TQKSLSLSLG | 180 |

TABLE 18

| clone | region | Amino acid sequence (N→C) or Nucleic acid sequence (5'→3') | SEQ ID NO |
|---|---|---|---|
| 20 | CDR-L1 | RASQSISSYLN | 181 |
| | CDR-L2 | DTSTLQS | 182 |
| | CDR-L3 | QQSYSFPWT | 183 |
| | CDR-H1 | SYAMS | 184 |
| | CDR-H2 | SISSSGGSTYYADSVKG | 185 |
| | CDR-H3 | ELGGYGFSYFDY | 186 |
| | light chain variable region | DIQMTQSPSSLSASVGDRVTITCRASQSISSYLNWYQQKP GKAPKLLIYDTSTLQSGVPSRFSGSGSGTDFTLTISSLQPE DFATYYCQQSYSFPWTFGQGTKVEIK | 187 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTTCTTACCTGAACTGGTATCAGCAGA AACCGGGCAAGGCGCCAAAATTGCTGATTTACGATACTT CCACTCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTTTTCCGTGGACGTTCGGGCAGGGAACTAAA GTGGAAATTAAA | 188 |
| | heavy chain variable region | QVQLVQSGAEVKKPGSSVKVSCKASGGTFSSYAMSWVR QAPGQGLEWMGSISSSGGSTYYADSVKGRVTITADESTST AYMELSSLRSEDTAVYYCARELGGYGFSYFDYWGQGTLV TVSS | 189 |

TABLE 18-continued

| clone | region | Amino acid sequence (N→C) or Nucleic acid sequence (5'→3') | SEQ ID NO |
|---|---|---|---|
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTATGCAATGTCTTGGGTGCGG CAGGCGCCCGGCCAGGGTCTCGAATGGATGGGGTCTA TCTCTTCTTCTGGTGGTTCTACTTACTATGCCGATTCAGT GAAGGGTCGCGTAACTATTACCGCCGACGAATCAACCT CCACCGCCTACATGGAACTCAGCTCTCTGAGGTCAGAA GACACGGCCGTCTATTATTGCGCCAGAGAACTGGGTGG TTACGGTTTCTCTTACTTCGATTACTGGGGTCAGGGCAC TTTAGTGACCGTCTCATCG | 190 |
| | light chain (Kappa) | DIQMTQSPSSLSASVGDRVTITCRASQSISSYLNWYQQKP GKAPKLLIYDTSTLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 191 |
| | heavy chain | QVQLVQSGAEVKKPGSSVKVSCKASGGTFSSYAMSWVR QAPGQGLEWMGSISSSGGSTYYADSVKGRVTITADESTST AYMELSSLRSEDTAVYYCARELGGYGFSYFDYWGQGTLV TVSSASTKGPSVFPLAPCSRSTSESTAALGCLVKDYFPEP VTVSWNSGALTSGVHTFPAVLQSSGLYSLSSVVTVPSSSL GTKTYTCNVDHKPSNTKVDKRVESKYGPPCPPCPAPEAA GGPSVFLFPPKPKDTLMISRTPEVTCVVVDVSQEDPEVQF NWYVDGVEVHNAKTKPREEQFNSTYRVVSVLTVLHQDWL NGKEYKCKVSNKGLPSSIEKTISKAKGQPREPQVYTLPPS QEEMTKNQVSLTCLVKGFYPSDIAVEWESNGQPENNYKT TPPVLDSDGSFFLYSRLTVDKSRWQEGNVFSCSVMHEAL HNHYTQKSLSLSLG | 192 |

TABLE 19

| clone | region | Amino acid sequence (N→C) or Nucleic acid sequence (5'→3') | SEQ ID NO |
|---|---|---|---|
| 21 | CDR-L1 | RASQSIRNYLN | 193 |
| | CDR-L2 | ATSSLQS | 194 |
| | CDR-L3 | QQSYSFPWT | 195 |
| | CDR-H1 | DYAMS | 196 |
| | CDR-H2 | GISGSDIYYADSVKG | 197 |
| | CDR-H3 | AVSYWSYTFDY | 198 |
| | light chain variable region | DIQMTQSPSSLSASVGDRVTITCRASQSIRNYLNWYQQKP GKAPKLLIYATSSLQSGVPSRFSGSGSGTDFTLTISSLQPE DFATYYCQQSYSFPWTFGQGTKVEIK | 199 |
| | light chain variable region coding y gene | GACATTCAAATGACGCAGAGTCCCTCCTCACTGAGTGC TAGCGTGGGCGATCGTGTGACAATTACTTGTCGCGCTA GCCAGTCTATCCGTAATTACCTGAACTGGTATCAGCAGA AACCGGGCAAGGCGCCAAAATTGCTGATTTACGCAACT TCCTCTCTGCAGTCTGGTGTACCGTCCCGTTTCTCTGG CAGCGGTTCTGGTACGGATTTTACCCTGACCATCTCAAG CCTCCAGCCTGAAGATTTTGCCACCTATTATTGTCAGCA ATCTTACTCTTTTCCGTGGACGTTCGGGCAGGGAACTAA AGTGGAAATTAAA | 200 |
| | heavy chain variable region | QVQLVQSGAEVKKPGSSVKVSCKASGGTFSDYAMSWVR QAPGQGLEWMGGISGSDIYYADSVKGRVTITADESTSTAY MELSSLRSEDTAVYYCARAVSYWSYTFDYWGQGTLVTVS S | 201 |
| | heavy chain variable | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTGATTATGCAATGTCTTGGGTGCGG | 202 |

TABLE 19-continued

| clone | region | Amino acid sequence (N→C) or Nucleic acid sequence (5'→3') | SEQ ID NO |
|---|---|---|---|
| | region coding gene | CAGGCGCCCGGCCAGGGTCTCGAATGGATGGGGGGTA TCTCTGGTTCTGATATCTACTATGCCGATTCAGTGAAGG GTCGCGTAACTATTACCGCCGACGAATCAACCTCCACCG CCTACATGGAACTCAGCTCTCTGAGGTCAGAAGACACG GCCGTCTATTATTGCGCCAGAGCAGTTTCTTACTGGTCT TACACTTTTGATTACTGGGGTCAGGGCACTTTAGTGACC GTCTCATCG | |
| | light chain (Kappa) | DIQMTQSPSSLSASVGDRVTITCRASQSIRNYLNWYQQKP GKAPKLLIYATSSLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 203 |
| | heavy chain | QVQLVQSGAEVKKPGSSVKVSCKASGGTFSDYAMSWVR QAPGQGLEWMGGISGSDIYYADSVKGRVTITADESTSTAY MELSSLRSEDTAVYYCARAVSYWSYTFDYWGQGTLVTVS SASTKGPSVFPLAPCSRSTSESTAALGCLVKDYFPEPVTV SWNSGALTSGVHTFPAVLQSSGLYSLSSVVTVPSSSLGTK TYTCNVDHKPSNTKVDKRVESKYGPPCPPCPAPEAAGGP SVFLFPPKPKDTLMISRTPEVTCVVVDVSQEDPEVQFNWY VDGVEVHNAKTKPREEQFNSTYRVVSVLTVLHQDWLNGK EYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHY TQKSLSLSLG | 204 |

TABLE 20

| clone | region | Amino acid sequence (N→C) or Nucleic acid sequence (5'→3') | SEQ ID NO |
|---|---|---|---|
| 22 | CDR-L1 | RASQSIGSYLN | 205 |
| | CDR-L2 | DASTLQS | 206 |
| | CDR-L3 | QQSYSFPWT | 207 |
| | CDR-H1 | SYAMH | 208 |
| | CDR-H2 | GISSSGGTTYYADSVKG | 209 |
| | CDR-H3 | ALGVVGGTWFDY | 210 |
| | light chain variable region | DIQMTQSPSSLSASVGDRVTITCRASQSIGSYLNWYQQKP GKAPKLLIYDASTLQSGVPSRFSGSGSGTDFTLTISSLQPE DFATYYCQQSYSFPWTFGQGTKVEIK | 211 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCGGTTCTTACCTGAACTGGTATCAGCAGA AACCCGGGCAAGGCGCCAAAATTGCTGATTTACGATGCAT CCACTCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTTTTCCGTGGACGTTCGGGCAGGGAACTAAA GTGGAAATTAAA | 212 |
| | heavy chain variable region | QVQLVQSGAEVKKPGSSVKVSCKASGGTFSSYAMHWVR QAPGQGLEWMGGISSSGGTTYYADSVKGRVTITADESTS TAYMELSSLRSEDTAVYYCARALGVVGGTWFDYWGQGTL VTVSS | 213 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTTCTTATGCAATGCACTGGGTGCG GCAGGCGCCCGGCCAGGGTCTCGAATGGATGGGGGGT ATCTCTTCTTCTGGTGGTACTACTTACTATGCCGATTCAG TGAAGGGTCGCGTAACTATTACCGCCGACGAATCAACCT CCACCGCCTACATGGAACTCAGCTCTCTGAGGTCAGAA | 214 |

TABLE 20-continued

| clone | region | Amino acid sequence (N→C) or Nucleic acid sequence (5'→3') | SEQ ID NO |
|---|---|---|---|
| | | GACACGGCCGTCTATTATTGCGCCAGAGCACTGGGTGT TGTTGGTGGTACTTGGTTCGATTACTGGGGTCAGGGCA CTTTAGTGACCGTCTCATCG | |
| | light chain (Kappa) | DIQMTQSPSSLSASVGDRVTITCRASQSIGSYLNWYQQKP GKAPKLLIYDASTLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 215 |
| | heavy chain | QVQLVQSGAEVKKPGSSVKVSCKASGGTFSSYAMHWVR QAPGQGLEWMGGISSSGGTTYYADSVKGRVTITADESTS TAYMELSSLRSEDTAVYYCARALGVVGGTWFDYWGQGTL VTVSSASTKGPSVFPLAPCSRSTSESTAALGCLVKDYFPE PVTVSWNSGALTSGVHTFPAVLQSSGLYSLSSVVTVPSSS LGTKTYTCNVDHKPSNTKVDKRVESKYGPPCPPCPAPEA AGGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLPP SQEEMTKNQVSLTCLVKGFYPSDIAVEWESNGQPENNYK TTPPVLDSDGSFFLYSRLTVDKSRWQEGNVFSCSVMHEA LHNHYTQKSLSLSLG | 216 |

TABLE 21

| clone | region | Amino acid sequence (N→C) or Nucleic acid sequence (5'→3') | SEQ ID NO |
|---|---|---|---|
| 23 | CDR-L1 | RASQSISNYLN | 217 |
| | CDR-L2 | DTSTLQS | 218 |
| | CDR-L3 | QQSYSFPWT | 219 |
| | CDR-H1 | DYAMH | 220 |
| | CDR-H2 | AISGSGGYTHYADSVKG | 221 |
| | CDR-H3 | SATFGVWETFDV | 222 |
| | light chain variable region | DIQMTQSPSSLSASVGDRVTITCRASQSISNYLNWYQQKP GKAPKLLIYDTSTLQSGVPSRFSGSGSGTDFTLTISSLQPE DFATYYCQQSYSFPWTFGQGTKVEIK | 223 |
| | light chain variable region coding gene | GACATTCAAATGACGCAGAGTCCCTCCTCACTGAGTGC TAGCGTGGGCGATCGTGTGACAATTACTTGTCGCGCTA GCCAGTCTATCTCTAATTACCTGAACTGGTATCAGCAGA AACCCGGCAAGGCGCCAAAATTGCTGATTTACGATACTT CCACTCTGCAGTCTGGTGTACCGTCCCGTTTCTCTGGC AGCGGTTCTGGTACGGATTTTACCCTGACCATCTCAAGC CTCCAGCCTGAAGATTTTGCCACCTATTATTGTCAGCAAT CTTACTCTTTTCCGTGGACGTTCGGGCAGGGAACTAAA GTGGAAATTAAA | 224 |
| | heavy chain variable region | QVQLVQSGAEVKKPGSSVKVSCKASGGTFSDYAMHWVR QAPGQGLEWMGAISGSGGYTHYADSVKGRVTITADESTS TAYMELSSLRSEDTAVYYCARSATFGVWETFDVWGQGTL VTVSS | 225 |
| | heavy chain variable region coding gene | CAAGTTCAGCTGGTCCAGAGCGGCGCAGAGGTGAAGA AGCCCGGCAGTTCTGTTAAGGTTTCCTGCAAAGCCTCA GGCGGGACTTTTAGTGATTATGCAATGCACTGGGTGCG GCAGGCGCCCGGCCAGGGTCTCGAATGGATGGGGGCA ATCTCTGGTTCTGGTGGTTACACTCACTATGCCGATTCA GTGAAGGGTCGCGTAACTATTACCGCCGACGAATCAAC CTCCACCGCCTACATGGAACTCAGCTCTCTGAGGTCAG AAGACACGGCCGTCTATTATTGCGCCAGATCTGCAACTT TCGGTGTTTGGGAAACTTTCGATGTTTGGGGTCAGGGC ACTTTAGTGACCGTCTCATCG | 226 |

TABLE 21-continued

| clone | region | Amino acid sequence (N→C) or Nucleic acid sequence (5'→3') | SEQ ID NO |
|-------|--------|-----------|-----|
| | light chain (Kappa) | DIQMTQSPSSLSASVGDRVTITCRASQSISNYLNWYQQKP GKAPKLLIYDTSTLQSGVPSRFSGSGSGTDFTLTISSLQPE DFATYYCQQSYSFPWTFGQGTKVEIKRTVAAPSVFIFPPS DEQLKSGTASVVCLLNNFYPREAKVQWKVDNALQSGNSQ ESVTEQDSKDSTYSLSSTLTLSKADYEKHKVYACEVTHQG LSSPVTKSFNRGEC | 227 |
| | heavy chain | QVQLVQSGAEVKKPGSSVKVSCKASGGTFSDYAMHWVR QAPGQGLEWMGAISGSGGYTHYADSVKGRVTITADESTS TAYMELSSLRSEDTAVYYCARSATFGVWETFDVWGQGTL VTVSSASTKGPSVFPLAPCSRSTSESTAALGQLVKDYFPE PVTVSWNSGALTSGVHTFPAVLQSSGLYSLSSVVTVPSSS LGTKTYTCNVDHKPSNTKVDKRVESKYGPPCPPCPAPEA AGGPSVFLFPPKPKDTLMISRTPEVTCVVVDVSQEDPEVQ FNWYVDGVEVHNAKTKPREEQFNSTYRVVSVLTVLHQDW LNGKEYKCKVSNKGLPSSIEKTISKAKGQPREPQVYTLPP SQEEMTKNQVSLTCLVKGFYPSDIAVEWESNGQPENNYK TTPPVLDSDGSFFLYSRLTVDKSRWQEGNVFSCSVMHEA LHNHYTQKSLSLSLG | 228 |

EXAMPLE 3. PREPARATION OF SELECTED ANTIBODIES

The vectors constructed in Example 2 were prepared using the Plasmid Plus Maxi kit (Qiagen). These vectors were used for expressing antibodies in ExpiCHO-S™ cells. The vectors were transfected into ExpiCHO-S™ cells (Gibco) ($1.2×10^9$ cells/Culture Volume 200 mL) by adding 640 µL of ExpiFectamine™ CHO reagent (Thermo Fisher). One day post-transfection, the cells were incubated in ExpiCHO™ Expression Media (Thermo Fisher) under the condition of 32° C. and 5% $CO_2$ for 7 to 11 days in total. On Day 1, 1200 µL of ExpiCHO™ Enhancer (Thermo Fisher) and 48 mL of ExpiCHO™ Feed (Thermo Fisher) were added to the culture.

The cultured cells were centrifuged at 3500 rpm at 4° C. for 20 minutes, and then, filtrated using 0.22 µm bottle-top filter system (Corning). The culture supernatant was harvested and purified using AKTA Pure L (GE healthcare). The culture supernatant was loaded into AKTA Pure L equipped with Hitrap MabSelectSure 5 mL column (GE healthcare) at the flow rate of 5 mL/min, and the column was washed with column volumes (CV) of 1×PBS. Then, elution buffer (0.1 M sodium citrate pH 3.4 buffer) was loaded to the column, to elute a protein of interest. The eluate was concentrated using Amicon Ultra Filter Device (MWCO 10K, Merck), centrifuged and subjected to buffer exchange with 1×PBS buffer.

The purified antibody samples were diluted with 1×PBS, to make the final concentration about 1 mg/mL. Ten (10) µL of Reducing Loading Buffer (3×) or Non-reducing Loading Buffer (3×) and 20 µL of the purified antibody sample were mixed and left in 95° C. heating bath for 2 minutes, and then, brought out and cooled. The sample was injected into SDS-PAGE Gradient Gel (4-12%) equipped on an electrophoresis device at the amount of 10 µg per well and developed on the gel. In order to analyze molecular weight of the sample, Precision Plus Protein™ Dual Color Standards (BIO-RAD) was injected to another separate well. The gel was stained with Coomassie staining solution and destained to obtain gel images (FIG. 1).

EXAMPLE 4. ANALYSIS OF BINDING AFFINITY OF THE SELECTED ANTIBODIES

The binding affinities of the 19 antibodies, which were selected in Example 3, to the antigen, LILRB1, were measured using Biacore T200 (GE healthcare). An anti-human IgG (Fc) antibody (GE healthcare, Cat. No. BR-1008-39, final concentration of 25 µg/mL) was flowed at the flow rate of 5 µL/min for 360 seconds to be immobilized at 5000-7000 RU on Series S Sensor Chip CM5 (GE healthcare, Cat. No. BR-1005-30) using Amine Coupling Kit (GE healthcare, Cat. No. BR-1000-50). The antigen, human LILRB1 protein (LILRB1-His, RnD systems Cat. No. 8989-T2) was injected thereto in 5 different concentrations from 25 nM to 400 nM at the flow rate of 30 µL/min to determine $k_a$ and $k_d$ values as shown in Table 22 and calculate $K_D$ value therefrom. Antibody No. 10 showed a binding affinity ($K_D$) of about 24.13 nM to the LILRB1 antigen, and antibody No. 13 showed a binding affinity ($K_D$) of about 30.27 nM to the LILRB1 antigen (Table 22). The sensorgram results for the antibody No. 13 are shown in FIG. 2.

TABLE 22

| | Antigen Binding Affinities ($K_D$) of LILRB1 antibodies | | |
|---|---|---|---|
| Clone number | $k_a$ ($× 10^5$) (1/Ms) | $k_d$ ($× 10^{-4}$) (1/s) | $K_D$ (nM) |
| 8 | 0.6166 | 46.37 | 75.2 |
| 10 | 0.1233 | 2.977 | 24.13 |
| 11 | 0.08662 | 1.061 | 12.25 |
| 13 | 0.9729 | 2.945 | 30.27 |
| 14 | 1.621 | 663.1 | 409.1 |
| 16 | 1.157 | 96.35 | 83.3 |
| 18 | 1.439 | 6.221 | 4.32 |
| 22 | 0.6826 | 340.8 | 499.3 |

EXAMPLE 5. ASSAY OF IN VITRO BIOLOGICAL ACTIVITIES OF THE SELECTED ANTIBODIES 5.1. Cell Surface Binding Assay In order to test whether or not the antibodies selected in Example 4 bind LILRB1 expressed on surface of cells, cell surface binding assay was performed. CHO cells overexpressing LILRB1 were cultured in Chemical Defined Medium, and added to a U-bottomed 96-well tissue culture plate (BD Falcon) to $2×10^5$ cells/well. Each of the selected antibodies was added to the well to the final concentration of 10 µg/mL per well, and incubated at 4° C. for 30 minutes. In order to see the level of LILRB1-specific binding of the selected antibodies, a human IgG4 isotype control antibody (Biolegend) was treated in the same manner. After washing with FACS buffer, the cells were treated with an anti-human Fc-biotin antibody (life technologies) and incubated at 4° C. for 1 hour. After washing with FACS buffer, streptavidin PE (BD Pharmigen) was added to each well and left at 4° C. for 30 minutes. After washing with FACS buffer, it was suspended and analyzed by iQue screener (Sartorius). As shown in FIG. 3, the No. 8, No. 10, No. 11, No. 13, and No. 18 antibodies showed a higher level of binding than that of the human IgG4 isotype control antibody.

5.2. Analysis of Increased Cancer Cell Killing Ability by Natural Killer (NK) Cells In order to determine whether the antibodies selected in Example 4 increase the degree of cancer cell lysis by NK cells, the cell death rate of HLA-G-overexpressing HEK293 cell by NK cell KHYG-1 was analyzed. KHYG-1 cells (JCRB) were added to 96-well tissue culture plate (BD Falcon) at the amount of $4\times10^5$ cells/well ($2\times10^4$ cells/mL). The selected antibody was added to the well to the final concentration of 10 µg/mL and incubated at 37° C. for one hour. As a negative control, a human IgG4 isotype control antibody (Biolegend) was treated in the same manner. HLA-G-overexpressing HEK293 cells were stained in a separate tube with IncuCyte CytoLight Rapid Red Reagent (Sartorius) according to the manufacturer's protocol. After one hour, the HLA-G-overexpressing HEK293 cells were added to the plate at the amount of $4\times10^5$ cells/well ($2\times10^4$ cells/mL). The plate was placed in IncuCyte S3 (Sartorius) equipped in an incubator under the condition of 37° C. and 5% $CO_2$, and images thereof were taken for 72 hours.

For comparison of the efficacy of each antibody, the normalized red area confluence value of the isotype control was converted to 1 to obtain the relative cell viability (Isotype=1) as shown in Equation 1 below.

Relative cell viability=[Normalized red area confluence value of antibody]/[Normalized red area confluence value of Isotype]  [Equation 1]

The obtained results are shown in FIG. 4. In FIG. 4, it can be interpreted that the lower the relative cell viability, the higher the NK cell mediated cytotoxicity by the anti-LILRB1 mAb. As shown in FIG. 4, all of the tested antibodies (antibody No. 10, No. 11, and No. 13) increased cell death of HLA-G-overexpressing HEK293 cells compared to human IgG4 isotype control. These results show that the antibody provided in the present invention exhibits high cytotoxicity against cancer cells.

EXAMPLE 6: ASSAY OF IN VIVO BIOLOGICAL ACTIVITIES OF THE TEST ANTIBODIES

Three antibodies (antibody No. 10, No. 11, and No. 13) whose binding ability to the antigen was confirmed in Example 3 were tested for their in vivo anti-cancer efficacies. For this purpose, it was tested whether or not the administration of three types of antibodies reduces the size of tumor where the tumor was generated by engrafting human colorectal carcinoma cells (Bioware Brite Cell Line HCT116 Red-Fluc colorectal cancer cells (PerkinElmer)) and THP-1 derived macrophage to the mice. As a negative control, human colon cancer xenograft mice prepared as above were treated with a human IgG1 isotype control antibody (BioXcell, Cat. No. BP0297).

6.1. Preparation of THP-1 Derived Macrophages

The THP-1 derived macrophages used above were prepared by differentiating THP-1 cells (ATCC) with 150 nM phorbol 12-myristate 13-acetate (PMA, Sigma), 20 ng/mL of interferon gamma (Peprotech) and 10 pg/mL of lipopolysaccharide (LPS, Sigma).

6.2. Measurement of Anti-Cancer Efficacy in Mouse Model

Five (5)-week-old female CIEA NOG Mouse (NOG immunodeficient mouse, Central Institute of Experimental Animals, Japan) were subcutaneously injected with a mixture of $3\times10^6$ cells of HCT116 Red-Fluc colorectal cancer cells, $3\times10^6$ cells of THP-1 derived macrophages and each of three antibodies (20 µg per mouse). From the 4th day after cell transplantation, each antibody was administered twice a week at the dosage of 5 mg/kg by intraperitoneal injection.

The change in tumor volume according to the administration of the antibody was measured and shown in FIG. 5. As shown in FIG. 5, all the tested antibodies (antibody No. 10, No. 11, and No. 13) showed statistically significant effect of inhibiting tumor growth in the mouse model transplanted with HCT116 colorectal cancer cells and THP-1 derived macrophages.

The invention claimed is:

1. An anti-LILRB1 antibody or antigen-binding fragment thereof, comprising:

(1) the CDR-L1 comprising the amino acid sequence of SEQ ID NO: 1, the CDR-L2 comprising the amino acid sequence of SEQ ID NO: 2, the CDR-L3 comprising the amino acid sequence of SEQ ID NO: 3, the CDR-H1 comprising the amino acid sequence of SEQ ID NO: 4, the CDR-H2 comprising the amino acid sequence of SEQ ID NO: 5, and the CDR-H3 comprising the amino acid sequence of SEQ ID NO: 6;

(2) the CDR-L1 comprising the amino acid sequence of SEQ ID NO: 13, the CDR-L2 comprising the amino acid sequence of SEQ ID NO: 14, the CDR-L3 comprising the amino acid sequence of SEQ ID NO: 15, the CDR-H1 comprising the amino acid sequence of SEQ ID NO: 16, the CDR-H2 comprising the amino acid sequence of SEQ ID NO: 17, and the CDR-H3 comprising the amino acid sequence of SEQ ID NO: 18;

(3) the CDR-L1 comprising the amino acid sequence of SEQ ID NO: 25, the CDR-L2 comprising the amino acid sequence of SEQ ID NO: 26, the CDR-L3 comprising the amino acid sequence of SEQ ID NO: 27, the CDR-H1 comprising the amino acid sequence of SEQ ID NO: 28, the CDR-H2 comprising the amino acid sequence of SEQ ID NO: 29, and the CDR-H3 comprising the amino acid sequence of SEQ ID NO: 30;

(4) the CDR-L1 comprising the amino acid sequence of SEQ ID NO: 37, the CDR-L2 comprising the amino acid sequence of SEQ ID NO: 38, the CDR-L3 comprising the amino acid sequence of SEQ ID NO: 39, the CDR-H1 comprising the amino acid sequence of SEQ ID NO: 40, the CDR-H2 comprising the amino acid sequence of SEQ ID NO: 41, and the CDR-H3 comprising the amino acid sequence of SEQ ID NO: 42;

(5) the CDR-L1 comprising the amino acid sequence of SEQ ID NO: 49, the CDR-L2 comprising the amino acid sequence of SEQ ID NO: 50, the CDR-L3 comprising the amino acid sequence of SEQ ID NO: 51, the CDR-H1 comprising the amino acid sequence of SEQ ID NO: 52, the CDR-H2 comprising the amino acid sequence of SEQ ID NO: 53, and the CDR-H3 comprising the amino acid sequence of SEQ ID NO: 54;

(6) the CDR-L1 comprising the amino acid sequence of SEQ ID NO: 61, the CDR-L2 comprising the amino acid sequence of SEQ ID NO: 62, the CDR-L3 comprising the amino acid sequence of SEQ ID NO: 63, the CDR-H1 comprising the amino acid sequence of SEQ ID NO: 64, the CDR-H2 comprising the amino acid sequence of SEQ ID NO: 65, and the CDR-H3 comprising the amino acid sequence of SEQ ID NO: 66;

(7) the CDR-L1 comprising the amino acid sequence of SEQ ID NO: 73, the CDR-L2 comprising the amino acid sequence of SEQ ID NO: 74, the CDR-L3 comprising the amino acid sequence of SEQ ID NO: 75, the CDR-H1 comprising the amino acid sequence of SEQ ID NO: 76, the CDR-H2 comprising the amino acid sequence of SEQ ID NO: 77, and the CDR-H3 comprising the amino acid sequence of SEQ ID NO: 78;

(8) the CDR-L1 comprising the amino acid sequence of SEQ ID NO: 85, the CDR-L2 comprising the amino acid sequence of SEQ ID NO:86, the CDR-L3 comprising the amino acid sequence of SEQ ID NO: 87, the CDR-H1 comprising the amino acid sequence of SEQ ID NO: 88, the CDR-H2 comprising the amino acid sequence of SEQ ID NO: 89, and the CDR-H3 comprising the amino acid sequence of SEQ ID NO: 90;

(9) the CDR-L1 comprising the amino acid sequence of SEQ ID NO: 97, the CDR-L2 comprising the amino acid sequence of SEQ ID NO: 98, the CDR-L3 comprising the amino acid sequence of SEQ ID NO: 99, the CDR-H1 comprising the amino acid sequence of SEQ ID NO: 100, the CDR-H2 comprising the amino acid sequence of SEQ ID NO: 101, and the CDR-H3 comprising the amino acid sequence of SEQ ID NO: 102;

(10) the CDR-L1 comprising the amino acid sequence of SEQ ID NO: 109, the CDR-L2 comprising the amino acid sequence of SEQ ID NO: 110, the CDR-L3 comprising the amino acid sequence of SEQ ID NO: 111, the CDR-H1 comprising the amino acid sequence of SEQ ID NO: 112, the CDR-H2 comprising the amino acid sequence of SEQ ID NO: 113, and the CDR-H3 comprising the amino acid sequence of SEQ ID NO: 114;

(11) the CDR-L1 comprising the amino acid sequence of SEQ ID NO: 121, the CDR-L2 comprising the amino acid sequence of SEQ ID NO: 122, the CDR-L3 comprising the amino acid sequence of SEQ ID NO: 123, the CDR-H1 comprising the amino acid sequence of SEQ ID NO: 124, the CDR-H2 comprising the amino acid sequence of SEQ ID NO: 125, and the CDR-H3 comprising the amino acid sequence of SEQ ID NO: 126;

(12) the CDR-L1 comprising the amino acid sequence of SEQ ID NO: 133, the CDR-L2 comprising the amino acid sequence of SEQ ID NO: 134, the CDR-L3 comprising the amino acid sequence of SEQ ID NO: 135, the CDR-H1 comprising the amino acid sequence of SEQ ID NO: 136, the CDR-H2 comprising the amino acid sequence of SEQ ID NO: 137, and the CDR-H3 comprising the amino acid sequence of SEQ ID NO: 138;

(13) the CDR-L1 comprising the amino acid sequence of SEQ ID NO: 145, the CDR-L2 comprising the amino acid sequence of SEQ ID NO: 146, the CDR-L3 comprising the amino acid sequence of SEQ ID NO: 147, the CDR-H1 comprising the amino acid sequence of SEQ ID NO: 148, the CDR-H2 comprising the amino acid sequence of SEQ ID NO: 149, and the CDR-H3 comprising the amino acid sequence of SEQ ID NO: 150;

(14) the CDR-L1 comprising the amino acid sequence of SEQ ID NO: 157, the CDR-L2 comprising the amino acid sequence of SEQ ID NO: 158, the CDR-L3 comprising the amino acid sequence of SEQ ID NO: 159, the CDR-H1 comprising the amino acid sequence of SEQ ID NO: 160, the CDR-H2 comprising the amino acid sequence of SEQ ID NO: 161, and the CDR-H3 comprising the amino acid sequence of SEQ ID NO: 162;

(15) the CDR-L1 comprising the amino acid sequence of SEQ ID NO: 169, the CDR-L2 comprising the amino acid sequence of SEQ ID NO: 170, the CDR-L3 comprising the amino acid sequence of SEQ ID NO: 171, the CDR-H1 comprising the amino acid sequence of SEQ ID NO: 172, the CDR-H2 comprising the amino acid sequence of SEQ ID NO: 173, and the CDR-H3 comprising the amino acid sequence of SEQ ID NO: 174;

(16) the CDR-L1 comprising the amino acid sequence of SEQ ID NO: 181, the CDR-L2 comprising the amino acid sequence of SEQ ID NO: 182, the CDR-L3 comprising the amino acid sequence of SEQ ID NO: 183, the CDR-H1 comprising the amino acid sequence of SEQ ID NO: 184, the CDR-H2 comprising the amino acid sequence of SEQ ID NO: 185, and the CDR-H3 comprising the amino acid sequence of SEQ ID NO: 186;

(17) the CDR-L1 comprising the amino acid sequence of SEQ ID NO: 193, the CDR-L2 comprising the amino acid sequence of SEQ ID NO: 194, the CDR-L3 comprising the amino acid sequence of SEQ ID NO: 195, the CDR-H1 comprising the amino acid sequence of SEQ ID NO: 196, the CDR-H2 comprising the amino acid sequence of SEQ ID NO: 197, and the CDR-H3 comprising the amino acid sequence of SEQ ID NO: 198;

(18) the CDR-L1 comprising the amino acid sequence of SEQ ID NO: 205, the CDR-L2 comprising the amino acid sequence of SEQ ID NO: 206, the CDR-L3 comprising the amino acid sequence of SEQ ID NO: 207, the CDR-H1 comprising the amino acid sequence of SEQ ID NO: 208, the CDR-H2 comprising the amino acid sequence of SEQ ID NO: 209, and the CDR-H3 comprising the amino acid sequence of SEQ ID NO: 210; or

(19) the CDR-L1 comprising the amino acid sequence of SEQ ID NO: 217, the CDR-L2 comprising the amino acid sequence of SEQ ID NO: 218, the CDR-L3 comprising the amino acid sequence of SEQ ID NO: 219, the CDR-H1 comprising the amino acid sequence of SEQ ID NO: 220, the CDR-H2 comprising the amino acid sequence of SEQ ID NO: 221, and the CDR-H3 comprising the amino acid sequence of SEQ ID NO: 222.

2. The anti-LILRB1 antibody or antigen-binding fragment thereof of claim 1, comprising:

a light chain variable region and
a heavy chain variable region comprising:
a) SEQ ID NOs: 7 and 9,
b) SEQ ID NOs: 19 and 21,
c) SEQ ID NOs: 31 and 33,
d) SEQ ID NOs: 43 and 45,
e) SEQ ID NOs: 55 and 57,
f) SEQ ID NOs: 67 and 69,
g) SEQ ID NOs: 79 and 81,
h) SEQ ID NOs: 91 and 93,
i) SEQ ID NOs: 103 and 105,
j) SEQ ID NOs: 115 and 117,
k) SEQ ID NOs: 127 and 129,
l) SEQ ID NOs: 139 and 141,
m) SEQ ID NOs: 151 and 153,
n) SEQ ID NOs: 163 and 165,
o) SEQ ID NOs: 175 and 177,
p) SEQ ID NOs: 187 and 189,
q) SEQ ID NOs: 199 and 201,
r) SEQ ID NOs: 211 and 213, or
s) SEQ ID NOs: 223 and 225, respectively.

3. The anti-LILRB1 antibody or antigen-binding fragment thereof of claim 1, wherein the antibody is a human IgG1 or IgG4 antibody.

4. The anti-LILRB1 antibody or antigen-binding fragment thereof of claim 1, wherein the antigen-binding fragment is a scFv, (scFv)$_2$, Fab, Fab', or F(ab')$_2$ of the anti-LILRB1 antibody, a fusion polypeptide comprising a scFv fused with an immunoglobulin Fc, or a fusion polypeptide comprising a scFv fused with a constant region of a light chain.

5. A pharmaceutical composition for treating a cancer, comprising the anti-LILRB1 antibody or antigen-binding fragment thereof of claim 1.

6. The pharmaceutical composition of claim 5, wherein the cancer has overexpression of MHC Class I.

7. The pharmaceutical composition of claim 5, wherein the composition has an activity of inhibiting immune evasion of cancer cells.

8. A nucleic acid molecule encoding the antibody or antigen-binding fragment thereof of claim 1.

9. A recombinant vector comprising the nucleic acid molecule of claim 8.

10. A recombinant cell comprising the recombinant vector of claim 9.

11. A method of preparing an anti-LILRB1 antibody or antigen-binding fragment thereof, comprising culturing the recombinant cell of claim 10.

12. A pharmaceutical composition for inhibiting immune evasion of cancer cells, comprising the anti-LILRB1 antibody or antigen-binding fragment thereof of claim 1.

13. A method for treating a cancer, comprising administering to a subject in need thereof a pharmaceutically effective amount of the anti-LILRB1 antibody or antigen-binding fragment thereof of claim 1.

14. The method of claim 13, wherein the cancer has overexpression of MHC Class I.

15. A method for inhibiting immune evasion of cancer cells, comprising administering to a subject in need thereof a pharmaceutically effective amount of the anti-LILRB1 antibody or antigen-binding fragment thereof of claim 1.

16. The pharmaceutical composition of claim 5, wherein the cancer is selected from the group consisting of lung cancer, peritoneal carcinoma, skin cancer, squamous cell carcinoma, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, leukemia, lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma, uterine carcinoma, salivary gland tumor, renal cell carcinoma, kidney cancer, prostate cancer, vulvar cancer, thyroid cancer, head and neck cancer, brain cancer, biliary tract cancer, gallbladder cancer, and bone osteosarcoma.

17. The method of claim 13, wherein the cancer is selected from the group consisting of lung cancer, peritoneal carcinoma, skin cancer, squamous cell carcinoma, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, leukemia, lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma, uterine carcinoma, salivary gland tumor, renal cell carcinoma, kidney cancer, prostate cancer, vulvar cancer, thyroid cancer, head and neck cancer, brain cancer, biliary tract cancer, gallbladder cancer, and bone osteosarcoma.

* * * * *

SEQUENCE LISTING

```
<160> NUMBER OF SEQ ID NOS: 230

<210> SEQ ID NO 1
<211> LENGTH: 11
<212> TYPE: PRT
<213> ORGANISM: Artificial Sequence
<220> FEATURE:
<223> OTHER INFORMATION: Synthetic (5_CDR-L1)

<400> SEQUENCE: 1

Arg Ala Ser Gln Ser Ile Ala Asn Tyr Leu Asn
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic (5_CDR-L2)
```

```
<400> SEQUENCE: 2

Ala Thr Ser Thr Leu Gln Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic (5_CDR-L3)

<400> SEQUENCE: 3

Gln Gln Ser Tyr Ser Phe Pro Trp Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic (5_CDR-H1)

<400> SEQUENCE: 4

Ala Tyr Gly Ile His
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic (5_CDR-H2)

<400> SEQUENCE: 5

Trp Ile Ile Pro Leu Ser Gly Gly Ala His Tyr Ala Gln Lys Phe Gln
1               5                   10                  15

Gly

<210> SEQ ID NO 6
<211> LENGTH: 10
<212> TYPE: PRT
<213> ORGANISM: Artificial Sequence
<220> FEATURE:
<223> OTHER INFORMATION: Synthetic (5_CDR-H3)

<400> SEQUENCE: 6

Leu Tyr Gly Trp Ala Glu Tyr Phe Asp Val
1               5                   10

<210> SEQ ID NO 7
<211> LENGTH: 107
<212> TYPE: PRT
<213> ORGANISM: Artificial Sequence
<220> FEATURE:
<223> OTHER INFORMATION: Synthetic (5_LightChain_VariableRegion)

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly
```

-continued

```
         50              55              60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100             105
```

```
<210> SEQ ID NO 8
<211> LENGTH: 321
<212> TYPE: DNA
<213> ORGANISM: Artificial Sequence
<220> FEATURE:
<223> OTHER INFORMATION: Synthetic (5_LightChain_VariableRegion_gene)

<400> SEQUENCE: 8
gacattcaaa tgacgcagag tccctcctca ctgagtgcta gcgtgggcga tcgtgtgaca      60
attacttgtc gcgctagcca gtctatcgca aattacctga actggtatca gcagaaaccg     120
ggcaaggcgc caaaattgct gatttacgca acttccactc tgcagtctgg tgtaccgtcc     180
cgtttctctg gcagcggttc tggtacggat tttaccctga ccatctcaag cctccagcct     240
gaagattttg ccacctatta ttgtcagcaa tcttactctt ttccgtggac gttcgggcag     300
ggaactaaag tggaaattaa a                                               321
```

```
<210> SEQ ID NO 9
<211> LENGTH: 119
<212> TYPE: PRT
<213> ORGANISM: Artificial Sequence
<220> FEATURE:
<223> OTHER INFORMATION: Synthetic (5_HeavyChain_VariableRegion)

<400> SEQUENCE: 9

Gln Val Gln Leu Val Gln Ser Gly Ala Glu Val Lys Lys Pro Gly Ser
1               5               10              15

Ser Val Lys Val Ser Cys Lys Ala Ser Gly Gly Thr Phe Ser Ala Tyr
                20              25              30

Gly Ile His Trp Val Arg Gln Ala Pro Gly Gln Gly Leu Glu Trp Met
        35              40              45

Gly Trp Ile Ile Pro Leu Ser Gly Gly Ala His Tyr Ala Gln Lys Phe
    50              55              60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Trp Ala Glu Tyr Phe Asp Val Trp Gly Gln Gly
            100             105             110

Thr Leu Val Thr Val Ser Ser
        115
```

```
<210> SEQ ID NO 10
<211> LENGTH: 357
<212> TYPE: DNA
<213> ORGANISM: Artificial Sequence
<220> FEATURE:
<223> OTHER INFORMATION: Synthetic (5_HeavyChain_VariableRegion_gene)

<400> SEQUENCE: 10
caagttcagc tggtccagag cggcgcagag gtgaagaagc ccggcagttc tgttaaggtt      60
```

```
tcctgcaaag cctcaggcgg gacttttagt gcatacggta tccattgggt gcggcaggcg    120
cccggccagg gtctcgaatg gatggggtgg attatcccac tgtctggtgg tgcacattat    180
gcacaaaaat tccaaggccg cgtaactatt accgccgacg aatcaacctc caccgcctac    240
atggaactca gctctctgag gtcagaagac acggccgtct attattgcgc cagactgtac    300
ggttgggcag aatacttcga tgtttggggt cagggtactc tggttaccgt ctcatcg      357
```

```
<210> SEQ ID NO 11
<211> LENGTH: 214
<212> TYPE: PRT
<213> ORGANISM: Artificial Sequence
<220> FEATURE:
<223> OTHER INFORMATION: Synthetic (5_LightChain_Kappa)

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asn Tyr
                20                  25                  30

Leu Asn Trp Tyr Gln Gln Lys Pro Gly Lys Ala Pro Lys Leu Leu Ile
            35                  40                  45

Tyr Ala Thr Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

```
<210> SEQ ID NO 12
<211> LENGTH: 445
<212> TYPE: PRT
<213> ORGANISM: Artificial Sequence
<220> FEATURE:
<223> OTHER INFORMATION: Synthetic (5_HeavyChain)

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
                20                  25                  30

Gly Ile His Trp Val Arg Gln Ala Pro Gly Gln Gly Leu Glu Trp Met
```

-continued

```
                35                  40                  45

Gly Trp Ile Ile Pro Leu Ser Gly Gly Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Trp Ala Glu Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445
```

<210> SEQ ID NO 13

```
<211> LENGTH: 11
<212> TYPE: PRT
<213> ORGANISM: Artificial Sequence
<220> FEATURE:
<223> OTHER INFORMATION: Synthetic (6_CDR-L1)

<400> SEQUENCE: 13

Arg Ala Ser Gln Ser Ile Ser Asn Tyr Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic (6_CDR-L2)

<400> SEQUENCE: 14

Ala Ala Ser Thr Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (6_CDR-L3)

<400> SEQUENCE: 15

Gln Gln Ser Tyr Ser Phe Pro Trp Thr
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic (6_CDR-H1)

<400> SEQUENCE: 16

Ser Tyr Thr Ile Ser
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic (6_CDR-H2)

<400> SEQUENCE: 17

Trp Ile Ser Pro Glu Leu Gly Thr Ser Asn Tyr Ala Gln Lys Phe Gln
1               5                   10                  15

Gly

<210> SEQ ID NO 18
<211> LENGTH: 12
<212> TYPE: PRT
<213> ORGANISM: Artificial Sequence
<220> FEATURE:
<223> OTHER INFORMATION: Synthetic (6_CDR-H3)

<400> SEQUENCE: 18

Leu Arg Tyr Gly Gln Thr Leu Tyr Gly Phe Asp Ile
1               5                   10
```

<210> SEQ ID NO 19
<211> LENGTH: 107
<212> TYPE: PRT
<213> ORGANISM: Artificial Sequence
<220> FEATURE:
<223> OTHER INFORMATION: Synthetic (6_LightChain_VariableRegion)

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105
```

<210> SEQ ID NO 20
<211> LENGTH: 321
<212> TYPE: DNA
<213> ORGANISM: Artificial Sequence
<220> FEATURE:
<223> OTHER INFORMATION: Synthetic (6_LightChain_VariableRegion_gene)

<400> SEQUENCE: 20

```
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc caaaattgct gatttacgca gcatccactc tgcagtctgg tgtaccgtcc     180
cgtttctctg gcagcggttc tggtacggat tttaccctga ccatctcaag cctccagcct     240
gaagattttg ccacctatta ttgtcagcaa tcttactctt ttccgtggac gttcgggcag     300
ggaactaaag tggaaattaa a                                               321
```

<210> SEQ ID NO 21
<211> LENGTH: 121
<212> TYPE: PRT
<213> ORGANISM: Artificial Sequence
<220> FEATURE:
<223> OTHER INFORMATION: Synthetic (6_HeavyChain_VariableRegion)

<400> SEQUENCE: 21

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Ser Pro Glu Leu Gly Thr Ser Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Leu Arg Tyr Gly Gln Thr Leu Tyr Gly Phe Asp Ile Trp Gly
            100                 105                 110

Gln Gly Thr Leu Val Thr Val Ser Ser
        115                 120
```

```
<210> SEQ ID NO 22
<211> LENGTH: 363
<212> TYPE: DNA
<213> ORGANISM: Artificial Sequence
<220> FEATURE:
<223> OTHER INFORMATION: Synthetic (6_HeavyChain_VariableRegion_gene)

<400> SEQUENCE: 22
caagttcagc tggtccagag cggcgcagag gtgaagaagc ccggcagttc tgttaaggtt      60
tcctgcaaag cctcaggcgg gacttttagt tcttacacca tttcttgggt gcggcaggcg     120
cccggccagg gtctcgaatg gatggggtgg atttctccag aactgggtac ctctaactat     180
gcacaaaaat tccaaggccg cgtaactatt accgccgacg aatcaacctc caccgcctac     240
atggaactca gctctctgag gtcagaagac acggccgtct attattgcgc cagactgcgt     300
tacggtcaga ctctgtacgg tttcgatatc tggggtcagg gtactctggt taccgtctca     360
tcg                                                                   363
```

```
<210> SEQ ID NO 23
<211> LENGTH: 214
<212> TYPE: PRT
<213> ORGANISM: Artificial Sequence
<220> FEATURE:
<223> OTHER INFORMATION: Synthetic (6_LightChain_Kappa)

<400> SEQUENCE: 23

Asp Ile Gln Met Thr Gln Ser Pro Ser Ser Leu Ser Ala Ser Val Gly
1                 5                  10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 24
<211> LENGTH: 447
<212> TYPE: PRT
<213> ORGANISM: Artificial Sequence
<220> FEATURE:
<223> OTHER INFORMATION: Synthetic (6_HeavyChain)

<400> SEQUENCE: 24

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Trp Ile Ser Pro Glu Leu Gly Thr Ser Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Arg Tyr Gly Gln Thr Leu Tyr Gly Phe Asp Ile Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
     370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
        435                 440                 445
```

<210> SEQ ID NO 25
<211> LENGTH: 11
<212> TYPE: PRT
<213> ORGANISM: Artificial Sequence
<220> FEATURE:
<223> OTHER INFORMATION: Synthetic (7_CDR-L1)

<400> SEQUENCE: 25

```
Arg Ala Ser Gln Ser Ile Ser Asn Trp Leu Asn
1               5                   10
```

<210> SEQ ID NO 26
<211> LENGTH: 7
<212> TYPE: PRT
<213> ORGANISM: Artificial Sequence
<220> FEATURE:
<223> OTHER INFORMATION: Synthetic (7_CDR-L2)

<400> SEQUENCE: 26

```
Gly Thr Ser Ser Leu Gln Ser
1               5
```

<210> SEQ ID NO 27
<211> LENGTH: 9
<212> TYPE: PRT
<213> ORGANISM: Artificial Sequence
<220> FEATURE:
<223> OTHER INFORMATION: Synthetic (7_CDR-L3)

<400> SEQUENCE: 27

```
Gln Gln Ser Tyr Ser Phe Pro Phe Thr
1               5
```

<210> SEQ ID NO 28
<211> LENGTH: 5
<212> TYPE: PRT
<213> ORGANISM: Artificial Sequence
<220> FEATURE:
<223> OTHER INFORMATION: Synthetic (7_CDR-H1)

<400> SEQUENCE: 28

```
Ser Tyr Gly Met His
1               5
```

<210> SEQ ID NO 29
<211> LENGTH: 17
<212> TYPE: PRT
<213> ORGANISM: Artificial Sequence
<220> FEATURE:
<223> OTHER INFORMATION: Synthetic (7_CDR-H2)

```
<400> SEQUENCE: 29

Trp Ile Ile Pro Val Ser Gly Gly Ala Thr Tyr Ala Gln Lys Phe Gln
1               5                   10                  15

Gly

<210> SEQ ID NO 30
<211> LENGTH: 11
<212> TYPE: PRT
<213> ORGANISM: Artificial Sequence
<220> FEATURE:
<223> OTHER INFORMATION: Synthetic (7_CDR-H3)

<400> SEQUENCE: 30

Gly Ser Trp Ala Tyr Tyr Ala Glu Phe Asp Tyr
1               5                   10

<210> SEQ ID NO 31
<211> LENGTH: 107
<212> TYPE: PRT
<213> ORGANISM: Artificial Sequence
<220> FEATURE:
<223> OTHER INFORMATION: Synthetic (7_LightChain_VariableRegion)

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
                20                  25                  30

Leu Asn Trp Tyr Gln Gln Lys Pro Gly Lys Ala Pro Lys Leu Leu Ile
            35                  40                  45

Tyr Gly Thr Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Phe
                85                  90                  95

Thr Phe Gly Gln Gly Thr Lys Val Glu Ile Lys
            100                 105

<210> SEQ ID NO 32
<211> LENGTH: 321
<212> TYPE: DNA
<213> ORGANISM: Artificial Sequence
<220> FEATURE:
<223> OTHER INFORMATION: Synthetic (7_LightChain_VariableRegion_gene)

<400> SEQUENCE: 32
gacattcaaa tgacgcagag tccctcctca ctgagtgcta gcgtgggcga tcgtgtgaca      60
attacttgtc gcgctagcca gtctatctct aattggctga ctggtatca gcagaaaccg     120 ggcaaggcgc caaaattgct gatttacggt acttcctctc tgcagtctgg tgtaccgtcc     180
cgtttctctg gcagcggttc tggtacggat tttaccctga ccatctcaag cctccagcct     240
gaagattttg ccacctatta ttgtcagcaa tcttactctt ttccgtttac gttcgggcag     300
ggaactaaag tggaaattaa a                                                321

<210> SEQ ID NO 33
<211> LENGTH: 120
<212> TYPE: PRT
<213> ORGANISM: Artificial Sequence
<220> FEATURE:
```

-continued

<223> OTHER INFORMATION: Synthetic (7_HeavyChain_VariableRegion)

<400> SEQUENCE: 33

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Met His Trp Val Arg Gln Ala Pro Gly Gln Gly Leu Glu Trp Met
        35                  40                  45

Gly Trp Ile Ile Pro Val Ser Gly Gly Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Trp Ala Tyr Tyr Ala Glu Phe Asp Tyr Trp Gly Gln
            100                 105                 110

Gly Thr Leu Val Thr Val Ser Ser
        115                 120
```

<210> SEQ ID NO 34
<211> LENGTH: 360
<212> TYPE: DNA
<213> ORGANISM: Artificial Sequence
<220> FEATURE:
<223> OTHER INFORMATION: Synthetic (7_HeavyChain_VariableRegion_gene)

<400> SEQUENCE: 34

```
caagttcagc tggtccagag cggcgcagag gtgaagaagc ccggcagttc tgttaaggtt        60
tcctgcaaag cctcaggcgg gacttttagt tcttacggta tgcattgggt gcggcaggcg       120
cccggccagg gtctcgaatg gatggggtgg attatcccag tttctggtgg tgcaacctat       180
gcacaaaaat tccaaggccg cgtaactatt accgccgacg aatcaacctc caccgcctac       240
atggaactca gctctctgag gtcagaagac acggccgtct attattgcgc cagaggttct       300
tgggcatact acgctgaatt cgattactgg ggtcagggca ctttagtgac cgtctcatcg       360
```

<210> SEQ ID NO 35
<211> LENGTH: 214
<212> TYPE: PRT
<213> ORGANISM: Artificial Sequence
<220> FEATURE:
<223> OTHER INFORMATION: Synthetic (7_LightChain_Kappa)

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Asn Trp Tyr Gln Gln Lys Pro Gly Lys Ala Pro Lys Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Phe
                85                  90                  95

Thr Phe Gly Gln Gly Thr Lys Val Glu Ile Lys Arg Thr Val Ala Ala
```

```
                100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 36
<211> LENGTH: 446
<212> TYPE: PRT
<213> ORGANISM: Artificial Sequence
<220> FEATURE:
<223> OTHER INFORMATION: Synthetic (7_HeavyChain)

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Met His Trp Val Arg Gln Ala Pro Gly Gln Gly Leu Glu Trp Met
        35                  40                  45

Gly Trp Ile Ile Pro Val Ser Gly Gly Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Trp Ala Tyr Tyr Ala Glu Phe Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
```

-continued

```
                     245                 250                 255

Pro Glu Val Thr Cys Val Val Val Asp Val Ser Gln Glu Asp Pro Glu
                 260                 265                 270

Val Gln Phe Asn Trp Tyr Val Asp Gly Val Glu Val His Asn Ala Lys
             275                 280                 285

Thr Lys Pro Arg Glu Glu Gln Phe Asn Ser Thr Tyr Arg Val Val Ser
         290                 295                 300

Val Leu Thr Val Leu His Gln Asp Trp Leu Asn Gly Lys Glu Tyr Lys
     305                 310                 315                 320

Cys Lys Val Ser Asn Lys Gly Leu Pro Ser Ser Ile Glu Lys Thr Ile
                 325                 330                 335

Ser Lys Ala Lys Gly Gln Pro Arg Glu Pro Gln Val Tyr Thr Leu Pro
                 340                 345                 350

Pro Ser Gln Glu Glu Met Thr Lys Asn Gln Val Ser Leu Thr Cys Leu
             355                 360                 365

Val Lys Gly Phe Tyr Pro Ser Asp Ile Ala Val Glu Trp Glu Ser Asn
         370                 375                 380

Gly Gln Pro Glu Asn Asn Tyr Lys Thr Thr Pro Pro Val Leu Asp Ser
     385                 390                 395                 400

Asp Gly Ser Phe Phe Leu Tyr Ser Arg Leu Thr Val Asp Lys Ser Arg
                 405                 410                 415

Trp Gln Glu Gly Asn Val Phe Ser Cys Ser Val Met His Glu Ala Leu
             420                 425                 430

His Asn His Tyr Thr Gln Lys Ser Leu Ser Leu Ser Leu Gly
         435                 440                 445
```

```
<210> SEQ ID NO 37
<211> LENGTH: 11
<212> TYPE: PRT
<213> ORGANISM: Artificial Sequence
<220> FEATURE:
<223> OTHER INFORMATION: Synthetic (8_CDR-L1)

<400> SEQUENCE: 37

Arg Ala Ser Gln Ser Ile Ser Ser Tyr Leu Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic (8_CDR-L2)

<400> SEQUENCE: 38

Ala Ala Ser Thr Leu Gln Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic (8_CDR-L3)

<400> SEQUENCE: 39

Gln Gln Ser Tyr Ser Phe Pro Tyr Thr
1               5

<210> SEQ ID NO 40
```

```
<211> LENGTH: 5
<212> TYPE: PRT
<213> ORGANISM: Artificial Sequence
<220> FEATURE:
<223> OTHER INFORMATION: Synthetic (8_CDR-H1)

<400> SEQUENCE: 40

Ser Tyr Gly Ile His
1               5

<210> SEQ ID NO 41
<211> LENGTH: 17
<212> TYPE: PRT
<213> ORGANISM: Artificial Sequence
<220> FEATURE:
<223> OTHER INFORMATION: Synthetic (8_CDR-H2)

<400> SEQUENCE: 41

Trp Ile Ile Pro Ile Ser Gly Thr Thr Asn Tyr Ala Gln Lys Phe Gln
1               5                   10                  15

Gly

<210> SEQ ID NO 42
<211> LENGTH: 11
<212> TYPE: PRT
<213> ORGANISM: Artificial Sequence
<220> FEATURE:
<223> OTHER INFORMATION: Synthetic (8_CDR-H3)

<400> SEQUENCE: 42

Val Gly Gly Val Gly Leu Tyr Val Phe Asp Val
1               5                   10

<210> SEQ ID NO 43
<211> LENGTH: 107
<212> TYPE: PRT
<213> ORGANISM: Artificial Sequence
<220> FEATURE:
<223> OTHER INFORMATION: Synthetic (8_LightChain_VariableRegion)

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Tyr
                85                  90                  95

Thr Phe Gly Gln Gly Thr Lys Val Glu Ile Lys
            100                 105

<210> SEQ ID NO 44
<211> LENGTH: 321
<212> TYPE: DNA
<213> ORGANISM: Artificial Sequence
<220> FEATURE:
<223> OTHER INFORMATION: Synthetic (8_LightChain_VariableRegion_gene)

<400> SEQUENCE: 44
```

```
gacattcaaa tgacgcagag tccctcctca ctgagtgcta gcgtgggcga tcgtgtgaca      60
attacttgtc gcgctagcca gtctatctct tcttacctga actggtatca gcagaaaccg     120
ggcaaggcgc caaaattgct gatttacgca gcatccactc tgcagtctgg tgtaccgtcc     180
cgtttctctg gcagcggttc tggtacggat tttaccctga ccatctcaag cctccagcct     240
gaagattttg ccacctatta ttgtcagcaa tcttactctt ttccgtacac gttcgggcag     300
ggaactaaag tggaaattaa a                                                321
```

```
<210> SEQ ID NO 45
<211> LENGTH: 120
<212> TYPE: PRT
<213> ORGANISM: Artificial Sequence
<220> FEATURE:
<223> OTHER INFORMATION: Synthetic (8_HeavyChain_VariableRegion)

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile His Trp Val Arg Gln Ala Pro Gly Gln Gly Leu Glu Trp Met
        35                  40                  45

Gly Trp Ile Ile Pro Ile Ser Gly Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Gly Val Gly Leu Tyr Val Phe Asp Val Trp Gly Gln
            100                 105                 110

Gly Thr Leu Val Thr Val Ser Ser
        115                 120
```

```
<210> SEQ ID NO 46
<211> LENGTH: 360
<212> TYPE: DNA
<213> ORGANISM: Artificial Sequence
<220> FEATURE:
<223> OTHER INFORMATION: Synthetic (8_HeavyChain_VariableRegion_gene)

<400> SEQUENCE: 46
caagttcagc tggtccagag cggcgcagag gtgaagaagc ccggcagttc tgttaaggtt      60
tcctgcaaag cctcaggcgg gacttttagt tcttacggta tccattgggt gcggcaggcg     120
cccggccagt gtctcgaatg gatggggtgg attatcccaa tctctggtac caccaactat     180
gcacaaaaat ccaaggccg cgtaactatt accgccgacg aatcaacctc caccgcctac      240
atggaactca gctctctgag gtcagaagac acggccgtct attattgcgc cagagttggt     300
ggtgttggtc tgtacgtttt cgatgtttgg ggtcagggta ctctggttac cgtctcatcg     360
```

```
<210> SEQ ID NO 47
<211> LENGTH: 214
<212> TYPE: PRT
<213> ORGANISM: Artificial Sequence
<220> FEATURE:
<223> OTHER INFORMATION: Synthetic (8_LightChain_Kappa)

<400> SEQUENCE: 47
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 48
<211> LENGTH: 446
<212> TYPE: PRT
<213> ORGANISM: Artificial Sequence
<220> FEATURE:
<223> OTHER INFORMATION: Synthetic (8_HeavyChain)

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile His Trp Val Arg Gln Ala Pro Gly Gln Gly Leu Glu Trp Met
        35                  40                  45

Gly Trp Ile Ile Pro Ile Ser Gly Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Gly Val Gly Leu Tyr Val Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
        130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
        435                 440                 445
```

```
<210> SEQ ID NO 49
<211> LENGTH: 11
<212> TYPE: PRT
<213> ORGANISM: Artificial Sequence
<220> FEATURE:
<223> OTHER INFORMATION: Synthetic (9_CDR-L1)

<400> SEQUENCE: 49

Arg Ala Ser Gln Ser Ile Ser Asn Tyr Leu Asn
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Synthetic (9_CDR-L2)

<400> SEQUENCE: 50
```

Ala Ala Ser Ser Leu Gln Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic (9_CDR-L3)

<400> SEQUENCE: 51

Gln Gln Ser Tyr Ser Phe Pro Trp Thr
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic (9_CDR-H1)

<400> SEQUENCE: 52

Ser Tyr Ala Ile His
1               5

<210> SEQ ID NO 53
<211> LENGTH: 17
<212> TYPE: PRT
<213> ORGANISM: Artificial Sequence
<220> FEATURE:
<223> OTHER INFORMATION: Synthetic (9_CDR-H2)

<400> SEQUENCE: 53

Trp Ile Val Pro Gly Leu Gly Val Thr Asn Tyr Ala Gln Lys Phe Gln
1               5                   10                  15

Gly

<210> SEQ ID NO 54
<211> LENGTH: 12
<212> TYPE: PRT
<213> ORGANISM: Artificial Sequence
<220> FEATURE:
<223> OTHER INFORMATION: Synthetic (9_CDR-H3)

<400> SEQUENCE: 54

Gln Ala Thr Leu Tyr Gln Thr Glu Tyr Met Asp Val
1               5                   10

<210> SEQ ID NO 55
<211> LENGTH: 107
<212> TYPE: PRT
<213> ORGANISM: Artificial Sequence
<220> FEATURE:
<223> OTHER INFORMATION: Synthetic (9_LightChain_VariableRegion)

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105
```

```
<210> SEQ ID NO 56
<211> LENGTH: 321
<212> TYPE: DNA
<213> ORGANISM: Artificial Sequence
<220> FEATURE:
<223> OTHER INFORMATION: Synthetic (9_LightChain_VariableRegion_gene)
```

```
<400> SEQUENCE: 56
```

```
gacattcaaa tgacgcagag tccctcctca ctgagtgcta gcgtgggcga tcgtgtgaca        60
attacttgtc gcgctagcca gtctatctct aattacctga actggtatca gcagaaaccg       120
ggcaaggcgc caaaattgct gatttacgca gcatcctctc tgcagtctgg tgtaccgtcc       180
cgtttctctg gcagcggttc tggtacggat tttaccctga ccatctcaag cctccagcct       240
gaagattttg ccacctatta ttgtcagcaa tcttactctt tccgtggac gttcgggcag        300 ggaactaaag tggaaattaa a                                                 321
```

```
<210> SEQ ID NO 57
<211> LENGTH: 121
<212> TYPE: PRT
<213> ORGANISM: Artificial Sequence
<220> FEATURE:
<223> OTHER INFORMATION: Synthetic (9_HeavyChain_VariableRegion)
```

```
<400> SEQUENCE: 57
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile His Trp Val Arg Gln Ala Pro Gly Gln Gly Leu Glu Trp Met
            35                  40                  45

Gly Trp Ile Val Pro Gly Leu Gly Val Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Thr Leu Tyr Gln Thr Glu Tyr Met Asp Val Trp Gly
            100                 105                 110

Gln Gly Thr Leu Val Thr Val Ser Ser
        115                 120
```

```
<210> SEQ ID NO 58
<211> LENGTH: 363
<212> TYPE: DNA
<213> ORGANISM: Artificial Sequence
<220> FEATURE:
<223> OTHER INFORMATION: Synthetic (9_HeavyChain_VariableRegion_gene)
```

```
<400> SEQUENCE: 58
```

```
caagttcagc tggtccagag cggcgcagag gtgaagaagc ccggcagttc tgttaaggtt        60
tcctgcaaag cctcaggcgg gacttttagt tcttacgcaa tccattgggt gcggcaggcg       120
```

```
cccggccagg gtctcgaatg gatggggtgg attgttccag gtctgggtgt taccaactat      180
gcacaaaaat tccaaggccg cgtaactatt accgccgacg aatcaacctc caccgcctac      240
atggaactca gctctctgag gtcagaagac acggccgtct attattgcgc cagacaggca      300
actctgtacc agactgaata catggatgtt tggggtcagg gtactctggt taccgtctca      360
tcg                                                                   363
```

```
<210> SEQ ID NO 59
<211> LENGTH: 214
<212> TYPE: PRT
<213> ORGANISM: Artificial Sequence
<220> FEATURE:
<223> OTHER INFORMATION: Synthetic (9_LightChain_Kappa)

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 60
<211> LENGTH: 447
<212> TYPE: PRT
<213> ORGANISM: Artificial Sequence
<220> FEATURE:
<223> OTHER INFORMATION: Synthetic (9_HeavyChain)

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile His Trp Val Arg Gln Ala Pro Gly Gln Gly Leu Glu Trp Met
    35                  40                  45

Gly Trp Ile Val Pro Gly Leu Gly Val Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln Ala Thr Leu Tyr Gln Thr Glu Tyr Met Asp Val Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
            435                 440                 445
```

```
<210> SEQ ID NO 61
<211> LENGTH: 11
<212> TYPE: PRT
<213> ORGANISM: Artificial Sequence
<220> FEATURE:
<223> OTHER INFORMATION: Synthetic (10_CDR-L1)

<400> SEQUENCE: 61

Arg Ala Ser Gln Ser Ile Ser Asn Tyr Leu Asn
1               5               10

<210> SEQ ID NO 62
<211> LENGTH: 7
<212> TYPE: PRT
<213> ORGANISM: Artificial Sequence
<220> FEATURE:
<223> OTHER INFORMATION: Synthetic (10_CDR-L2)

<400> SEQUENCE: 62

Ala Ala Ser Asn Leu Gln Ser
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic (10_CDR-L3)

<400> SEQUENCE: 63

Gln Gln Ser Tyr Ser Phe Pro Phe Thr
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic (10_CDR-H1)

<400> SEQUENCE: 64

Ser His Tyr Met His
1               5

<210> SEQ ID NO 65
<211> LENGTH: 17
<212> TYPE: PRT
<213> ORGANISM: Artificial Sequence
<220> FEATURE:
<223> OTHER INFORMATION: Synthetic (10_CDR-H2)

<400> SEQUENCE: 65

Trp Ile Ser Pro Tyr Leu Gly Ser Thr Asn Tyr Ala Gln Lys Phe Gln
1               5                   10                  15

Gly

<210> SEQ ID NO 66
<211> LENGTH: 12
<212> TYPE: PRT
<213> ORGANISM: Artificial Sequence
<220> FEATURE:
<223> OTHER INFORMATION: Synthetic (10_CDR-H3)

<400> SEQUENCE: 66

Asp Glu Thr Gly Ser Thr Tyr Gly Ala Phe Asp Tyr
1               5                   10
```

<210> SEQ ID NO 67
<211> LENGTH: 107
<212> TYPE: PRT
<213> ORGANISM: Artificial Sequence
<220> FEATURE:
<223> OTHER INFORMATION: Synthetic (10_LightChain_VariableRegion)

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Phe
                85                  90                  95

Thr Phe Gly Gln Gly Thr Lys Val Glu Ile Lys
            100                 105
```

<210> SEQ ID NO 68
<211> LENGTH: 321
<212> TYPE: DNA
<213> ORGANISM: Artificial Sequence
<220> FEATURE:
<223> OTHER INFORMATION: Synthetic (10_LightChain_VariableRegion_gene)

<400> SEQUENCE: 68

```
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc aaaattgct  gatttacgca gcatccaatc tgcagtctgg tgtaccgtcc     180
cgtttctctg gcagcggttc tggtacggat tttaccctga ccatctcaag cctccagcct     240
gaagattttg ccacctatta ttgtcagcaa tcttactctt ttccgtttac gttcgggcag     300
ggaactaaag tggaaattaa a                                               321
```

<210> SEQ ID NO 69
<211> LENGTH: 121
<212> TYPE: PRT
<213> ORGANISM: Artificial Sequence
<220> FEATURE:
<223> OTHER INFORMATION: Synthetic (10_HeavyChain_VariableRegion)

<400> SEQUENCE: 69

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Tyr Met His Trp Val Arg Gln Ala Pro Gly Gln Gly Leu Glu Trp Met
            35                  40                  45

Gly Trp Ile Ser Pro Tyr Leu Gly Ser Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

```
                        85              90              95
Ala Arg Asp Glu Thr Gly Ser Thr Tyr Gly Ala Phe Asp Tyr Trp Gly
            100             105             110

Gln Gly Thr Leu Val Thr Val Ser Ser
        115             120

<210> SEQ ID NO 70
<211> LENGTH: 363
<212> TYPE: DNA
<213> ORGANISM: Artificial Sequence
<220> FEATURE:
<223> OTHER INFORMATION: Synthetic (10_HeavyChain_VariableRegion_gene)

<400> SEQUENCE: 70
caagttcagc tggtccagag cggcgcagag gtgaagaagc ccggcagttc tgttaaggtt     60
tcctgcaaag cctcaggcgg gacttttagt tctcattaca tgcattgggt gcggcaggcg    120
cccggccagg gtctcgaatg gatggggtgg atttctccat acctgggttc taccaactat    180
gcacaaaaat tccaaggccg cgtaactatt accgccgacg aatcaacctc caccgcctac    240
atggaactca gctctctgag gtcagaagac acggccgtct attattgcgc cagagatgaa    300
actggttcta cttacggtgc attcgattac tggggtcagg gtactctggt taccgtctca    360
tcg                                                                 363

<210> SEQ ID NO 71
<211> LENGTH: 214
<212> TYPE: PRT
<213> ORGANISM: Artificial Sequence
<220> FEATURE:
<223> OTHER INFORMATION: Synthetic (10_LightChain_Kappa)

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Phe
                85                  90                  95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
                165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
```

```
          195                 200                 205

Phe Asn Arg Gly Glu Cys
    210

<210> SEQ ID NO 72
<211> LENGTH: 447
<212> TYPE: PRT
<213> ORGANISM: Artificial Sequence
<220> FEATURE:
<223> OTHER INFORMATION: Synthetic (10_HeavyChain)

<400> SEQUENCE: 72

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
            20                  25                  30

Tyr Met His Trp Val Arg Gln Ala Pro Gly Gln Gly Leu Glu Trp Met
        35                  40                  45

Gly Trp Ile Ser Pro Tyr Leu Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Thr Gly Ser Thr Tyr Gly Ala Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
```

-continued

```
                340               345               350
Pro Pro Ser Gln Glu Glu Met Thr Lys Asn Gln Val Ser Leu Thr Cys
        355               360               365
Leu Val Lys Gly Phe Tyr Pro Ser Asp Ile Ala Val Glu Trp Glu Ser
    370               375               380
Asn Gly Gln Pro Glu Asn Asn Tyr Lys Thr Thr Pro Pro Val Leu Asp
385               390               395               400
Ser Asp Gly Ser Phe Phe Leu Tyr Ser Arg Leu Thr Val Asp Lys Ser
                405               410               415
Arg Trp Gln Glu Gly Asn Val Phe Ser Cys Ser Val Met His Glu Ala
            420               425               430
Leu His Asn His Tyr Thr Gln Lys Ser Leu Ser Leu Ser Leu Gly
        435               440               445
```

<210> SEQ ID NO 73
<211> LENGTH: 11
<212> TYPE: PRT
<213> ORGANISM: Artificial Sequence
<220> FEATURE:
<223> OTHER INFORMATION: Synthetic (11_CDR-L1)

<400> SEQUENCE: 73

```
Arg Ala Ser Gln Ser Ile Ser Asn Tyr Leu Asn
1               5               10
```

<210> SEQ ID NO 74
<211> LENGTH: 7
<212> TYPE: PRT
<213> ORGANISM: Artificial Sequence
<220> FEATURE:
<223> OTHER INFORMATION: Synthetic (11_CDR-L2)

<400> SEQUENCE: 74

```
Asp Ala Ser Thr Leu Gln Ser
1               5
```

<210> SEQ ID NO 75
<211> LENGTH: 9
<212> TYPE: PRT
<213> ORGANISM: Artificial Sequence
<220> FEATURE:
<223> OTHER INFORMATION: Synthetic (11_CDR-L3)

<400> SEQUENCE: 75

```
Gln Gln Ser Tyr Ser Phe Pro Trp Thr
1               5
```

<210> SEQ ID NO 76
<211> LENGTH: 5
<212> TYPE: PRT
<213> ORGANISM: Artificial Sequence
<220> FEATURE:
<223> OTHER INFORMATION: Synthetic (11_CDR-H1)

<400> SEQUENCE: 76

```
Ser Tyr Tyr Val His
1               5
```

<210> SEQ ID NO 77
<211> LENGTH: 17
<212> TYPE: PRT
<213> ORGANISM: Artificial Sequence
<220> FEATURE:
<223> OTHER INFORMATION: Synthetic (11_CDR-H2)

<400> SEQUENCE: 77

Trp Ile Ser Pro Tyr Ser Gly Gly Thr Asn Tyr Ala Gln Lys Phe Gln
1               5                   10                  15

Gly

<210> SEQ ID NO 78
<211> LENGTH: 12
<212> TYPE: PRT
<213> ORGANISM: Artificial Sequence
<220> FEATURE:
<223> OTHER INFORMATION: Synthetic (11_CDR-H3)

<400> SEQUENCE: 78

Asp Tyr Tyr Val Ser Ala Tyr Gly Ala Phe Asp Tyr
1               5                   10

<210> SEQ ID NO 79
<211> LENGTH: 107
<212> TYPE: PRT
<213> ORGANISM: Artificial Sequence
<220> FEATURE:
<223> OTHER INFORMATION: Synthetic (11_LightChain_VariableRegion)

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105

<210> SEQ ID NO 80
<211> LENGTH: 321
<212> TYPE: DNA
<213> ORGANISM: Artificial Sequence
<220> FEATURE:
<223> OTHER INFORMATION: Synthetic (11_LightChain_VariableRegion_gene)

<400> SEQUENCE: 80
gacattcaaa tgacgcagag tccctcctca ctgagtgcta gcgtgggcga tcgtgtgaca        60
attacttgtc gcgctagcca gtctatctct aattacctga actggtatca gcagaaaccg       120
ggcaaggcgc caaaattgct gatttacgat gcatccactc tgcagtctgg tgtaccgtcc       180
cgtttctctg gcagcggttc tggtacggat tttaccctga ccatctcaag cctccagcct       240
gaagattttg ccacctatta ttgtcagcaa tcttactctt ttccgtggac gttcgggcag       300
ggaactaaag tggaaattaa a                                                  321

<210> SEQ ID NO 81
<211> LENGTH: 121
<212> TYPE: PRT
<213> ORGANISM: Artificial Sequence
<220> FEATURE:
<223> OTHER INFORMATION: Synthetic (11_HeavyChain_VariableRegion)

<400> SEQUENCE: 81

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Val His Trp Val Arg Gln Ala Pro Gly Gln Gly Leu Glu Trp Met
        35                  40                  45

Gly Trp Ile Ser Pro Tyr Ser Gly Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Val Ser Ala Tyr Gly Ala Phe Asp Tyr Trp Gly
            100                 105                 110

Gln Gly Thr Leu Val Thr Val Ser Ser
        115                 120
```

<210> SEQ ID NO 82
<211> LENGTH: 363
<212> TYPE: DNA
<213> ORGANISM: Artificial Sequence
<220> FEATURE:
<223> OTHER INFORMATION: Synthetic (11_HeavyChain_VariableRegion_gene)

<400> SEQUENCE: 82

```
caagttcagc tggtccagag cggcgcagag gtgaagaagc ccggcagttc tgttaaggtt      60
tcctgcaaag cctcaggcgg gacttttagt tcttactacg ttcattgggt gcggcaggcg     120
cccggccagg gtctcgaatg gatggggtgg atttctccat actctggtgg taccaactat     180
gcacaaaaat tccaaggccg cgtaactatt accgccgacg aatcaacctc caccgcctac     240
atggaactca gctctctgag gtcagaagac acggccgtct attattgcgc cagagattac     300
tacgtttctg catacggtgc attcgattac tggggtcagg gtactctggt taccgtctca     360
tcg                                                                    363
```

<210> SEQ ID NO 83
<211> LENGTH: 214
<212> TYPE: PRT
<213> ORGANISM: Artificial Sequence
<220> FEATURE:
<223> OTHER INFORMATION: Synthetic (11_LightChain_Kappa)

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
```

```
                       85                   90                   95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 84
<211> LENGTH: 447
<212> TYPE: PRT
<213> ORGANISM: Artificial Sequence
<220> FEATURE:
<223> OTHER INFORMATION: Synthetic (11_HeavyChain)

<400> SEQUENCE: 84

Gln Val Gln Leu Val Gln Ser Gly Ala Glu Val Lys Lys Pro Gly Ser
1                   5                   10                  15

Ser Val Lys Val Ser Cys Lys Ala Ser Gly Gly Thr Phe Ser Ser Tyr
                20                  25                  30

Tyr Val His Trp Val Arg Gln Ala Pro Gly Gln Gly Leu Glu Trp Met
            35                  40                  45

Gly Trp Ile Ser Pro Tyr Ser Gly Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Val Ser Ala Tyr Gly Ala Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
```

-continued

```
225              230              235              240

Val Phe Leu Phe Pro Pro Lys Pro Lys Asp Thr Leu Met Ile Ser Arg
            245              250              255

Thr Pro Glu Val Thr Cys Val Val Val Asp Val Ser Gln Glu Asp Pro
            260              265              270

Glu Val Gln Phe Asn Trp Tyr Val Asp Gly Val Glu Val His Asn Ala
            275              280              285

Lys Thr Lys Pro Arg Glu Glu Gln Phe Asn Ser Thr Tyr Arg Val Val
            290              295              300

Ser Val Leu Thr Val Leu His Gln Asp Trp Leu Asn Gly Lys Glu Tyr
305              310              315              320

Lys Cys Lys Val Ser Asn Lys Gly Leu Pro Ser Ser Ile Glu Lys Thr
            325              330              335

Ile Ser Lys Ala Lys Gly Gln Pro Arg Glu Pro Gln Val Tyr Thr Leu
            340              345              350

Pro Pro Ser Gln Glu Glu Met Thr Lys Asn Gln Val Ser Leu Thr Cys
            355              360              365

Leu Val Lys Gly Phe Tyr Pro Ser Asp Ile Ala Val Glu Trp Glu Ser
            370              375              380

Asn Gly Gln Pro Glu Asn Asn Tyr Lys Thr Thr Pro Pro Val Leu Asp
385              390              395              400

Ser Asp Gly Ser Phe Phe Leu Tyr Ser Arg Leu Thr Val Asp Lys Ser
            405              410              415

Arg Trp Gln Glu Gly Asn Val Phe Ser Cys Ser Val Met His Glu Ala
            420              425              430

Leu His Asn His Tyr Thr Gln Lys Ser Leu Ser Leu Ser Leu Gly
            435              440              445

<210> SEQ ID NO 85
<211> LENGTH: 11
<212> TYPE: PRT
<213> ORGANISM: Artificial Sequence
<220> FEATURE:
<223> OTHER INFORMATION: Synthetic (12_CDR-L1)

<400> SEQUENCE: 85

Arg Ala Ser Gln Asp Ile Ser Asn Tyr Leu Asn
1               5              10

<210> SEQ ID NO 86
<211> LENGTH: 7
<212> TYPE: PRT
<213> ORGANISM: Artificial Sequence
<220> FEATURE:
<223> OTHER INFORMATION: Synthetic (12_CDR-L2)

<400> SEQUENCE: 86

Ala Thr Ser Ser Leu Gln Ser
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic (12_CDR-L3)

<400> SEQUENCE: 87

Gln Gln Ser Tyr Ser Phe Pro Trp Thr
1               5
```

<210> SEQ ID NO 88
<211> LENGTH: 5
<212> TYPE: PRT
<213> ORGANISM: Artificial Sequence
<220> FEATURE:
<223> OTHER INFORMATION: Synthetic (12_CDR-H1)

<400> SEQUENCE: 88

Ser Tyr Asp Ile His
1               5

<210> SEQ ID NO 89
<211> LENGTH: 17
<212> TYPE: PRT
<213> ORGANISM: Artificial Sequence
<220> FEATURE:
<223> OTHER INFORMATION: Synthetic (12_CDR-H2)

<400> SEQUENCE: 89

Arg Ile Val Pro Tyr Leu Gly Val Thr Asn Tyr Ala Gln Lys Phe Gln
1               5                   10                  15

Gly

<210> SEQ ID NO 90
<211> LENGTH: 12
<212> TYPE: PRT
<213> ORGANISM: Artificial Sequence
<220> FEATURE:
<223> OTHER INFORMATION: Synthetic (12_CDR-H3)

<400> SEQUENCE: 90

Arg Gln Ser Gln Ser Ser Val Tyr Ala Phe Asp Ile
1               5                   10

<210> SEQ ID NO 91
<211> LENGTH: 107
<212> TYPE: PRT
<213> ORGANISM: Artificial Sequence
<220> FEATURE:
<223> OTHER INFORMATION: Synthetic (12_LightChain_VariableRegion)

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Thr Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105

<210> SEQ ID NO 92
<211> LENGTH: 321
<212> TYPE: DNA
<213> ORGANISM: Artificial Sequence
<220> FEATURE:

<223> OTHER INFORMATION: Synthetic (12_LightChain_VariableRegion_gene)

<400> SEQUENCE: 92
gacattcaaa tgacgcagag tccctcctca ctgagtgcta gcgtgggcga tcgtgtgaca          60
attacttgtc gcgctagcca ggatatctct aattacctga actggtatca gcagaaaccg         120
ggcaaggcgc caaaattgct gatttacgca acttcctctc tgcagtctgg tgtaccgtcc         180
cgtttctctg gcagcggttc tggtacggat tttacccctga ccatctcaag cctccagcct        240
gaagattttg ccacctatta ttgtcagcaa tcttactctt ttccgtggac gttcgggcag         300
ggaactaaag tggaaattaa a                                                    321

<210> SEQ ID NO 93
<211> LENGTH: 121
<212> TYPE: PRT
<213> ORGANISM: Artificial Sequence
<220> FEATURE:
<223> OTHER INFORMATION: Synthetic (12_HeavyChain_VariableRegion)

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile His Trp Val Arg Gln Ala Pro Gly Gln Gly Leu Glu Trp Met
        35                  40                  45

Gly Arg Ile Val Pro Tyr Leu Gly Val Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gln Ser Gln Ser Ser Val Tyr Ala Phe Asp Ile Trp Gly
            100                 105                 110

Gln Gly Thr Leu Val Thr Val Ser Ser
        115                 120

<210> SEQ ID NO 94
<211> LENGTH: 363
<212> TYPE: DNA
<213> ORGANISM: Artificial Sequence
<220> FEATURE:
<223> OTHER INFORMATION: Synthetic (12_HeavyChain_VariableRegion_gene)

<400> SEQUENCE: 94
caagttcagc tggtccagag cggcgcagag gtgaagaagc ccggcagttc tgttaaggtt          60
tcctgcaaag cctcaggcgg gacttttagt tcttacgata tccattgggt gcggcaggcg         120
cccggccagg gtctcgaatg gatgggggcgt attgttccat acctgggtgt taccaactat        180
gcacaaaaat ccaaggccg cgtaactatt accgccgacg aatcaacctc caccgcctac         240
atggaactca gctctctgag gtcagaagac acggccgtct attattgcgc cagacgtcag         300
tctcagtctt ctgtttacgc attcgatatc tggggtcagg cactttagt gaccgtctca         360 tcg                                                                        363

<210> SEQ ID NO 95
<211> LENGTH: 214
<212> TYPE: PRT
<213> ORGANISM: Artificial Sequence -continued
<220> FEATURE:
<223> OTHER INFORMATION: Synthetic (12_LightChain_Kappa)

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 96
<211> LENGTH: 447
<212> TYPE: PRT
<213> ORGANISM: Artificial Sequence
<220> FEATURE:
<223> OTHER INFORMATION: Synthetic (12_HeavyChain)

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile His Trp Val Arg Gln Ala Pro Gly Gln Gly Leu Glu Trp Met
        35                  40                  45

Gly Arg Ile Val Pro Tyr Leu Gly Val Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gln Ser Gln Ser Ser Val Tyr Ala Phe Asp Ile Trp Gly
            100                 105                 110

Gln Gly Thr Leu Val Thr Val Ser Ser Ala Ser Thr Lys Gly Pro Ser

-continued

```
            115                 120                 125
Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
        435                 440                 445
```

```
<210> SEQ ID NO 97
<211> LENGTH: 11
<212> TYPE: PRT
<213> ORGANISM: Artificial Sequence
<220> FEATURE:
<223> OTHER INFORMATION: Synthetic (13_CDR-L1)

<400> SEQUENCE: 97

Arg Ala Ser Gln Ser Ile Ser Asn Tyr Leu Asn
1               5               10

<210> SEQ ID NO 98
<211> LENGTH: 7
<212> TYPE: PRT
```

-continued

<213> ORGANISM: Artificial Sequence
<220> FEATURE:
<223> OTHER INFORMATION: Synthetic (13_CDR-L2)

<400> SEQUENCE: 98

Ala Ala Ser Arg Leu Gln Ser
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic (13_CDR-L3)

<400> SEQUENCE: 99

Gln Gln Ser Tyr Ser Phe Pro Phe Thr
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic (13_CDR-H1)

<400> SEQUENCE: 100

Gly Tyr Tyr Ile His
1               5

<210> SEQ ID NO 101
<211> LENGTH: 17
<212> TYPE: PRT
<213> ORGANISM: Artificial Sequence
<220> FEATURE:
<223> OTHER INFORMATION: Synthetic (13_CDR-H2)

<400> SEQUENCE: 101

Trp Ile Ser Pro Ser Ser Gly Gly Thr Ile Tyr Ala Gln Lys Phe Gln
1               5                   10                  15

Gly

<210> SEQ ID NO 102
<211> LENGTH: 12
<212> TYPE: PRT
<213> ORGANISM: Artificial Sequence
<220> FEATURE:
<223> OTHER INFORMATION: Synthetic (13_CDR-H3)

<400> SEQUENCE: 102

Asp Ile Ser Val Arg Val Val Gln Ala Phe Asp Tyr
1               5                   10

<210> SEQ ID NO 103
<211> LENGTH: 107
<212> TYPE: PRT
<213> ORGANISM: Artificial Sequence
<220> FEATURE:
<223> OTHER INFORMATION: Synthetic (13_LightChain_VariableRegion)

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Phe
                85                  90                  95

Thr Phe Gly Gln Gly Thr Lys Val Glu Ile Lys
            100                 105

<210> SEQ ID NO 104
<211> LENGTH: 321
<212> TYPE: DNA
<213> ORGANISM: Artificial Sequence
<220> FEATURE:
<223> OTHER INFORMATION: Synthetic (13_LightChain_VariableRegion_gene)

<400> SEQUENCE: 104
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc aaaattgct gatttacgca gcatcccgtc tgcagtctgg tgtaccgtcc      180
cgtttctctg gcagcggttc tggtacggat tttaccctga ccatctcaag cctccagcct     240
gaagattttg ccacctatta ttgtcagcaa tcttactctt ttccgtttac gttcgggcag     300
ggaactaaag tggaaattaa a                                               321

<210> SEQ ID NO 105
<211> LENGTH: 121
<212> TYPE: PRT
<213> ORGANISM: Artificial Sequence
<220> FEATURE:
<223> OTHER INFORMATION: Synthetic (13_HeavyChain_VariableRegion)

<400> SEQUENCE: 105

Gln Val Gln Leu Val Gln Ser Gly Ala Glu Val Lys Lys Pro Gly Ser
1                   5                   10                  15

Ser Val Lys Val Ser Cys Lys Ala Ser Gly Gly Thr Phe Ser Gly Tyr
            20                  25                  30

Tyr Ile His Trp Val Arg Gln Ala Pro Gly Gln Gly Leu Glu Trp Met
        35                  40                  45

Gly Trp Ile Ser Pro Ser Ser Gly Gly Thr Ile Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Val Arg Val Val Gln Ala Phe Asp Tyr Trp Gly
            100                 105                 110

Gln Gly Thr Leu Val Thr Val Ser Ser
        115                 120

<210> SEQ ID NO 106
<211> LENGTH: 363
<212> TYPE: DNA
<213> ORGANISM: Artificial Sequence
<220> FEATURE:
<223> OTHER INFORMATION: Synthetic (13_HeavyChain_VariableRegion_gene)

```
<400> SEQUENCE: 106
caagttcagc tggtccagag cggcgcagag gtgaagaagc ccggcagttc tgttaaggtt      60
tcctgcaaag cctcaggcgg gactttagt ggttactaca tccattgggt gcggcaggcg      120
cccggccagg gtctcgaatg gatggggtgg atttctccat cttctggtgg taccatctat      180
gcacaaaaat tccaaggccg cgtaactatt accgccgacg aatcaacctc caccgcctac      240
atggaactca gctctctgag gtcagaagac acggccgtct attattgcgc cagagatatc      300
tctgttcgtg ttgttcaggc attcgattac tggggtcagg gtactctggt taccgtctca      360
tcg                                                                    363

<210> SEQ ID NO 107
<211> LENGTH: 214
<212> TYPE: PRT
<213> ORGANISM: Artificial Sequence
<220> FEATURE:
<223> OTHER INFORMATION: Synthetic (13_LightChain_Kappa)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 108
<211> LENGTH: 447
<212> TYPE: PRT
<213> ORGANISM: Artificial Sequence
<220> FEATURE:
<223> OTHER INFORMATION: Synthetic (13_HeavyChain)

<400> SEQUENCE: 108

Gln Val Gln Leu Val Gln Ser Gly Ala Glu Val Lys Lys Pro Gly Ser
```

-continued

```
1                   5                   10                  15

Ser Val Lys Val Ser Cys Lys Ala Ser Gly Gly Thr Phe Ser Gly Tyr
            20                  25                  30

Tyr Ile His Trp Val Arg Gln Ala Pro Gly Gln Gly Leu Glu Trp Met
            35                  40                  45

Gly Trp Ile Ser Pro Ser Ser Gly Gly Thr Ile Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ile Ser Val Arg Val Val Gln Ala Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430
```

Leu His Asn His Tyr Thr Gln Lys Ser Leu Ser Leu Ser Leu Gly
        435                 440                 445

<210> SEQ ID NO 109
<211> LENGTH: 11
<212> TYPE: PRT
<213> ORGANISM: Artificial Sequence
<220> FEATURE:
<223> OTHER INFORMATION: Synthetic (14_CDR-L1)

<400> SEQUENCE: 109

Arg Ala Ser Gln Ser Ile Ser Asn Tyr Leu Asn
1               5                   10

<210> SEQ ID NO 110
<211> LENGTH: 7
<212> TYPE: PRT
<213> ORGANISM: Artificial Sequence
<220> FEATURE:
<223> OTHER INFORMATION: Synthetic (14_CDR-L2)

<400> SEQUENCE: 110

Ala Thr Ser Asn Leu Gln Ser
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic (14_CDR-L3)

<400> SEQUENCE: 111

Gln Gln Ser Tyr Ser Phe Pro Trp Thr
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic (14_CDR-H1)

<400> SEQUENCE: 112

Ser Tyr Tyr Met His
1               5

<210> SEQ ID NO 113
<211> LENGTH: 17
<212> TYPE: PRT
<213> ORGANISM: Artificial Sequence
<220> FEATURE:
<223> OTHER INFORMATION: Synthetic (14_CDR-H2)

<400> SEQUENCE: 113

Trp Ile Ser Pro Tyr Leu Gly Ile Thr Asn Tyr Ala Gln Lys Phe Gln
1               5                   10                  15

Gly

<210> SEQ ID NO 114
<211> LENGTH: 12
<212> TYPE: PRT
<213> ORGANISM: Artificial Sequence
<220> FEATURE:
<223> OTHER INFORMATION: Synthetic (14_CDR-H3)

<400> SEQUENCE: 114

Ala Gly Tyr Gln Gln Ala Gln Tyr Trp Phe Asp Tyr
1               5                   10

<210> SEQ ID NO 115
<211> LENGTH: 107
<212> TYPE: PRT
<213> ORGANISM: Artificial Sequence
<220> FEATURE:
<223> OTHER INFORMATION: Synthetic (14_LightChain_VariableRegion)

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Thr Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105

<210> SEQ ID NO 116
<211> LENGTH: 321
<212> TYPE: DNA
<213> ORGANISM: Artificial Sequence
<220> FEATURE:
<223> OTHER INFORMATION: Synthetic (14_LightChain_VariableRegion_gene)

<400> SEQUENCE: 116
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc caaaattgct gatttacgca acttccaatc tgcagtctgg tgtaccgtcc     180
cgtttctctg gcagcggttc tggtacggat tttaccctga ccatctcaag cctccagcct     240
gaagattttg ccacctatta ttgtcagcaa tcttactctt ttccgtggac gttcgggcag     300
ggaactaaag tggaaattaa a                                               321

<210> SEQ ID NO 117
<211> LENGTH: 121
<212> TYPE: PRT
<213> ORGANISM: Artificial Sequence
<220> FEATURE:
<223> OTHER INFORMATION: Synthetic (14_HeavyChain_VariableRegion)

<400> SEQUENCE: 117

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Tyr Met His Trp Val Arg Gln Ala Pro Gly Gln Gly Leu Glu Trp Met
            35                  40                  45

Gly Trp Ile Ser Pro Tyr Leu Gly Ile Thr Asn Tyr Ala Gln Lys Phe
        50                  55                  60

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Tyr Gln Gln Ala Gln Tyr Trp Phe Asp Tyr Trp Gly
            100                 105                 110

Gln Gly Thr Leu Val Thr Val Ser Ser
        115                 120
```

```
<210> SEQ ID NO 118
<211> LENGTH: 363
<212> TYPE: DNA
<213> ORGANISM: Artificial Sequence
<220> FEATURE:
<223> OTHER INFORMATION: Synthetic (14_HeavyChain_VariableRegion_gene)

<400> SEQUENCE: 118
caagttcagc tggtccagag cggcgcagag gtgaagaagc ccggcagttc tgttaaggtt    60
tcctgcaaag cctcaggcgg gacttttagt tcttactaca tgcattgggt gcggcaggcg   120
cccggccagt gtctcgaatg gatggggtgg atttctccat acctgggtat caccaactat   180
gcacaaaaat tccaaggccg cgtaactatt accgccgacg aatcaacctc caccgcctac   240
atggaactca gctctctgag gtcagaagac acggccgtct attattgcgc cagagcaggt   300
taccagcagg cacagtactg gttcgattac tggggtcagg gcactttagt gaccgtctca   360
tcg                                                                 363
```

```
<210> SEQ ID NO 119
<211> LENGTH: 214
<212> TYPE: PRT
<213> ORGANISM: Artificial Sequence
<220> FEATURE:
<223> OTHER INFORMATION: Synthetic (14_LightChain_Kappa)

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Thr Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 120
<211> LENGTH: 447
<212> TYPE: PRT
<213> ORGANISM: Artificial Sequence
<220> FEATURE:
<223> OTHER INFORMATION: Synthetic (14_HeavyChain)

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
        20                  25                  30

Tyr Met His Trp Val Arg Gln Ala Pro Gly Gln Gly Leu Glu Trp Met
        35                  40                  45

Gly Trp Ile Ser Pro Tyr Leu Gly Ile Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Gly Tyr Gln Gln Ala Gln Tyr Trp Phe Asp Tyr Trp Gly
        100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
        165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445
```

```
<210> SEQ ID NO 121
<211> LENGTH: 11
<212> TYPE: PRT
<213> ORGANISM: Artificial Sequence
<220> FEATURE:
<223> OTHER INFORMATION: Synthetic (15_CDR-L1)

<400> SEQUENCE: 121

Arg Ala Ser Gln Ser Ile Ser Asn Tyr Leu Asn
1               5                   10

<210> SEQ ID NO 122
<211> LENGTH: 7
<212> TYPE: PRT
<213> ORGANISM: Artificial Sequence
<220> FEATURE:
<223> OTHER INFORMATION: Synthetic (15_CDR-L2)

<400> SEQUENCE: 122

Ala Thr Ser Ser Leu Gln Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic (15_CDR-L3)

<400> SEQUENCE: 123

Gln Gln Ser Tyr Ser Phe Pro Tyr Thr
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic (15_CDR-H1)

<400> SEQUENCE: 124

Ser Tyr Ala Met Ser
1               5

<210> SEQ ID NO 125
```

```
<211> LENGTH: 17
<212> TYPE: PRT
<213> ORGANISM: Artificial Sequence
<220> FEATURE:
<223> OTHER INFORMATION: Synthetic (15_CDR-H2)

<400> SEQUENCE: 125

Trp Ile Ile Pro Ile Ser Gly Thr Thr Asn Tyr Ala Gln Lys Phe Gln
1               5                   10                  15

Gly

<210> SEQ ID NO 126
<211> LENGTH: 10
<212> TYPE: PRT
<213> ORGANISM: Artificial Sequence
<220> FEATURE:
<223> OTHER INFORMATION: Synthetic (15_CDR-H3)

<400> SEQUENCE: 126

Gln His Ser Val Gly Ser Val Phe Asp Tyr
1               5                   10

<210> SEQ ID NO 127
<211> LENGTH: 107
<212> TYPE: PRT
<213> ORGANISM: Artificial Sequence
<220> FEATURE:
<223> OTHER INFORMATION: Synthetic (15_LightChain_VariableRegion)

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Tyr
                85                  90                  95

Thr Phe Gly Gln Gly Thr Lys Val Glu Ile Lys
            100                 105

<210> SEQ ID NO 128
<211> LENGTH: 321
<212> TYPE: DNA
<213> ORGANISM: Artificial Sequence
<220> FEATURE:
<223> OTHER INFORMATION: Synthetic (15_LightChain_VariableRegion_gene)

<400> SEQUENCE: 128
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc aaaattgct gatttacgca acttcctctc tgcagtctgg tgtaccgtcc      180
cgtttctctg gcagcggttc tggtacggat tttaccctga ccatctcaag cctccagcct     240
gaagattttg ccacctatta ttgtcagcaa tcttactctt ttccgtacac gttcgggcag     300
ggaactaaag tggaaattaa a                                                321
```

```
<210> SEQ ID NO 129
<211> LENGTH: 119
<212> TYPE: PRT
<213> ORGANISM: Artificial Sequence
<220> FEATURE:
<223> OTHER INFORMATION: Synthetic (15_HeavyChain_VariableRegion)

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Trp Ile Ile Pro Ile Ser Gly Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gln His Ser Val Gly Ser Val Phe Asp Tyr Trp Gly Gln Gly
            100                 105                 110

Thr Leu Val Thr Val Ser Ser
        115

<210> SEQ ID NO 130
<211> LENGTH: 357
<212> TYPE: DNA
<213> ORGANISM: Artificial Sequence
<220> FEATURE:
<223> OTHER INFORMATION: Synthetic (15_HeavyChain_VariableRegion_gene)

<400> SEQUENCE: 130
caagttcagc tggtccagag cggcgcagag gtgaagaagc ccggcagttc tgttaaggtt      60
tcctgcaaag cctcaggcgg gacttttagt tcttacgcaa tgtcttgggt gcggcaggcg     120
cccggccagg gtctcgaatg gatggggtgg attatcccaa tctctggtac caccaactat     180
gcacaaaaat tccaaggccg cgtaactatt accgccgacg aatcaacctc caccgcctac     240
atggaactca gctctctgag gtcagaagac acggccgtct attattgcgc cagacagcat     300
tctgttggtt ctgttttcga ttactggggt cagggtactc tggttaccgt ctcatcg       357

<210> SEQ ID NO 131
<211> LENGTH: 214
<212> TYPE: PRT
<213> ORGANISM: Artificial Sequence
<220> FEATURE:
<223> OTHER INFORMATION: Synthetic (15_LightChain_Kappa)

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
65              70              75              80

Glu Asp Phe Ala Thr Tyr Tyr Cys Gln Gln Ser Tyr Ser Phe Pro Tyr
                85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
            115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
            195             200             205

Phe Asn Arg Gly Glu Cys
    210

<210> SEQ ID NO 132
<211> LENGTH: 445
<212> TYPE: PRT
<213> ORGANISM: Artificial Sequence
<220> FEATURE:
<223> OTHER INFORMATION: Synthetic (15_HeavyChain)

<400> SEQUENCE: 132

Gln Val Gln Leu Val Gln Ser Gly Ala Glu Val Lys Lys Pro Gly Ser
1               5               10              15

Ser Val Lys Val Ser Cys Lys Ala Ser Gly Gly Thr Phe Ser Ser Tyr
            20              25              30

Ala Met Ser Trp Val Arg Gln Ala Pro Gly Gln Gly Leu Glu Trp Met
            35              40              45

Gly Trp Ile Ile Pro Ile Ser Gly Thr Thr Asn Tyr Ala Gln Lys Phe
    50              55              60

Gln Gly Arg Val Thr Ile Thr Ala Asp Glu Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Gln His Ser Val Gly Ser Val Phe Asp Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Cys Ser Arg Ser Thr Ser Glu Ser Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Lys Thr Tyr Thr Cys Asn Val Asp His Lys Pro
            195             200             205

Ser Asn Thr Lys Val Asp Lys Arg Val Glu Ser Lys Tyr Gly Pro Pro
```

```
         210              215              220

Cys Pro Pro Cys Pro Ala Pro Glu Ala Ala Gly Gly Pro Ser Val Phe
225              230              235              240

Leu Phe Pro Pro Lys Pro Lys Asp Thr Leu Met Ile Ser Arg Thr Pro
             245              250              255

Glu Val Thr Cys Val Val Val Asp Val Ser Gln Glu Asp Pro Glu Val
             260              265              270

Gln Phe Asn Trp Tyr Val Asp Gly Val Glu Val His Asn Ala Lys Thr
         275              280              285

Lys Pro Arg Glu Glu Gln Phe Asn Ser Thr Tyr Arg Val Val Ser Val
     290              295              300

Leu Thr Val Leu His Gln Asp Trp Leu Asn Gly Lys Glu Tyr Lys Cys
305              310              315              320

Lys Val Ser Asn Lys Gly Leu Pro Ser Ser Ile Glu Lys Thr Ile Ser
             325              330              335

Lys Ala Lys Gly Gln Pro Arg Glu Pro Gln Val Tyr Thr Leu Pro Pro
             340              345              350

Ser Gln Glu Glu Met Thr Lys Asn Gln Val Ser Leu Thr Cys Leu Val
             355              360              365

Lys Gly Phe Tyr Pro Ser Asp Ile Ala Val Glu Trp Glu Ser Asn Gly
     370              375              380

Gln Pro Glu Asn Asn Tyr Lys Thr Thr Pro Pro Val Leu Asp Ser Asp
385              390              395              400

Gly Ser Phe Phe Leu Tyr Ser Arg Leu Thr Val Asp Lys Ser Arg Trp
             405              410              415

Gln Glu Gly Asn Val Phe Ser Cys Ser Val Met His Glu Ala Leu His
             420              425              430

Asn His Tyr Thr Gln Lys Ser Leu Ser Leu Ser Leu Gly
         435              440              445
```

<210> SEQ ID NO 133
<211> LENGTH: 11
<212> TYPE: PRT
<213> ORGANISM: Artificial Sequence
<220> FEATURE:
<223> OTHER INFORMATION: Synthetic (16_CDR-L1)

<400> SEQUENCE: 133

```
Arg Ala Ser Gln Asp Ile Ser Ser Trp Leu Asn
1               5               10
```

<210> SEQ ID NO 134
<211> LENGTH: 7
<212> TYPE: PRT
<213> ORGANISM: Artificial Sequence
<220> FEATURE:
<223> OTHER INFORMATION: Synthetic (16_CDR-L2)

<400> SEQUENCE: 134

```
Ala Ala Ser Ser Leu Gln Ser
1               5
```

<210> SEQ ID NO 135
<211> LENGTH: 9
<212> TYPE: PRT
<213> ORGANISM: Artificial Sequence
<220> FEATURE:
<223> OTHER INFORMATION: Synthetic (16_CDR-L3)

<400> SEQUENCE: 135

```
Gln Gln Ser Tyr Ser Phe Pro Trp Thr
1               5
```

```
<210> SEQ ID NO 136
<211> LENGTH: 5
<212> TYPE: PRT
<213> ORGANISM: Artificial Sequence
<220> FEATURE:
<223> OTHER INFORMATION: Synthetic (16_CDR-H1)
```

```
<400> SEQUENCE: 136
```

```
Ser Tyr Tyr Met Thr
1               5
```

```
<210> SEQ ID NO 137
<211> LENGTH: 17
<212> TYPE: PRT
<213> ORGANISM: Artificial Sequence
<220> FEATURE:
<223> OTHER INFORMATION: Synthetic (16_CDR-H2)
```

```
<400> SEQUENCE: 137
```

```
Gly Ile Ser Pro Ile Leu Gly Val Thr Asn Tyr Ala Gln Lys Phe Gln
1               5                   10                  15

Gly
```

```
<210> SEQ ID NO 138
<211> LENGTH: 12
<212> TYPE: PRT
<213> ORGANISM: Artificial Sequence
<220> FEATURE:
<223> OTHER INFORMATION: Synthetic (16_CDR-H3)
```

```
<400> SEQUENCE: 138
```

```
Leu Leu Val Gly Val Ser Glu Thr Tyr Phe Asp Tyr
1               5                   10
```

```
<210> SEQ ID NO 139
<211> LENGTH: 107
<212> TYPE: PRT
<213> ORGANISM: Artificial Sequence
<220> FEATURE:
<223> OTHER INFORMATION: Synthetic (16_LightChain_VariableRegion)
```

```
<400> SEQUENCE: 139
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105
```

```
<210> SEQ ID NO 140
<211> LENGTH: 321
```

```
<212> TYPE: DNA
<213> ORGANISM: Artificial Sequence
<220> FEATURE:
<223> OTHER INFORMATION: Synthetic (16_LightChain_VariableRegion_gene)

<400> SEQUENCE: 140
gacattcaaa tgacgcagag tccctcctca ctgagtgcta gcgtgggcga tcgtgtgaca        60
attacttgtc gcgctagcca ggatatctct tcttggctga actggtatca gcagaaaccg       120
ggcaaggcgc caaaattgct gatttacgca gcatcctctc tgcagtctgg tgtaccgtcc       180
cgtttctctg gcagcggttc tggtacggat tttaccctga ccatctcaag cctccagcct       240
gaagattttg ccacctatta ttgtcagcaa tcttactctt ttccgtggac gttcgggcag       300
ggaactaaag tggaaattaa a                                                 321

<210> SEQ ID NO 141
<211> LENGTH: 121
<212> TYPE: PRT
<213> ORGANISM: Artificial Sequence
<220> FEATURE:
<223> OTHER INFORMATION: Synthetic (16_HeavyChain_VariableRegion)

<400> SEQUENCE: 141

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Met Thr Trp Val Arg Gln Ala Pro Gly Gln Gly Leu Glu Trp Met
        35                  40                  45

Gly Gly Ile Ser Pro Ile Leu Gly Val Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Val Gly Val Ser Glu Thr Tyr Phe Asp Tyr Trp Gly
            100                 105                 110

Gln Gly Thr Leu Val Thr Val Ser Ser
        115                 120

<210> SEQ ID NO 142
<211> LENGTH: 363
<212> TYPE: DNA
<213> ORGANISM: Artificial Sequence
<220> FEATURE:
<223> OTHER INFORMATION: Synthetic (16_HeavyChain_VariableRegion_gene)

<400> SEQUENCE: 142
caagttcagc tggtccagag cggcgcagag gtgaagaagc ccggcagttc tgttaaggtt        60
tcctgcaaag cctcaggcgg dacttttagt tcttactaca tgacctgggt gcggcaggcg       120
cccggccagg gtctcgaatg gatggggggt atttctccaa tcctgggtgt taccaactat       180
gcacaaaaat tccaaggccg cgtaactatt accgccgacg aatcaacctc caccgcctac       240
atggaactca gctctctgag gtcagaagac acggccgtct attattgcgc cagactgctg       300
gttggtgttt ctgaaactta cttcgattac tggggtcagg gtactctggt taccgtctca       360
tcg                                                                     363

<210> SEQ ID NO 143
```

<211> LENGTH: 214
<212> TYPE: PRT
<213> ORGANISM: Artificial Sequence
<220> FEATURE:
<223> OTHER INFORMATION: Synthetic (16_LightChain_Kappa)

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 144
<211> LENGTH: 447
<212> TYPE: PRT
<213> ORGANISM: Artificial Sequence
<220> FEATURE:
<223> OTHER INFORMATION: Synthetic (16_HeavyChain)

<400> SEQUENCE: 144

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Met Thr Trp Val Arg Gln Ala Pro Gly Gln Gly Leu Glu Trp Met
        35                  40                  45

Gly Gly Ile Ser Pro Ile Leu Gly Val Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Val Gly Val Ser Glu Thr Tyr Phe Asp Tyr Trp Gly

-continued

```
                100                  105                  110

Gln Gly Thr Leu Val Thr Val Ser Ser Ala Ser Thr Lys Gly Pro Ser
            115                  120                  125

Val Phe Pro Leu Ala Pro Cys Ser Arg Ser Thr Ser Glu Ser Thr Ala
    130                  135                  140

Ala Leu Gly Cys Leu Val Lys Asp Tyr Phe Pro Glu Pro Val Thr Val
145                  150                  155                  160

Ser Trp Asn Ser Gly Ala Leu Thr Ser Gly Val His Thr Phe Pro Ala
                165                  170                  175

Val Leu Gln Ser Ser Gly Leu Tyr Ser Leu Ser Ser Val Val Thr Val
                180                  185                  190

Pro Ser Ser Ser Leu Gly Thr Lys Thr Tyr Thr Cys Asn Val Asp His
            195                  200                  205

Lys Pro Ser Asn Thr Lys Val Asp Lys Arg Val Glu Ser Lys Tyr Gly
    210                  215                  220

Pro Pro Cys Pro Pro Cys Pro Ala Pro Glu Ala Ala Gly Gly Pro Ser
225                  230                  235                  240

Val Phe Leu Phe Pro Pro Lys Pro Lys Asp Thr Leu Met Ile Ser Arg
                245                  250                  255

Thr Pro Glu Val Thr Cys Val Val Val Asp Val Ser Gln Glu Asp Pro
                260                  265                  270

Glu Val Gln Phe Asn Trp Tyr Val Asp Gly Val Glu Val His Asn Ala
            275                  280                  285

Lys Thr Lys Pro Arg Glu Glu Gln Phe Asn Ser Thr Tyr Arg Val Val
    290                  295                  300

Ser Val Leu Thr Val Leu His Gln Asp Trp Leu Asn Gly Lys Glu Tyr
305                  310                  315                  320

Lys Cys Lys Val Ser Asn Lys Gly Leu Pro Ser Ser Ile Glu Lys Thr
                325                  330                  335

Ile Ser Lys Ala Lys Gly Gln Pro Arg Glu Pro Gln Val Tyr Thr Leu
                340                  345                  350

Pro Pro Ser Gln Glu Glu Met Thr Lys Asn Gln Val Ser Leu Thr Cys
            355                  360                  365

Leu Val Lys Gly Phe Tyr Pro Ser Asp Ile Ala Val Glu Trp Glu Ser
    370                  375                  380

Asn Gly Gln Pro Glu Asn Asn Tyr Lys Thr Thr Pro Pro Val Leu Asp
385                  390                  395                  400

Ser Asp Gly Ser Phe Phe Leu Tyr Ser Arg Leu Thr Val Asp Lys Ser
                405                  410                  415

Arg Trp Gln Glu Gly Asn Val Phe Ser Cys Ser Val Met His Glu Ala
            420                  425                  430

Leu His Asn His Tyr Thr Gln Lys Ser Leu Ser Leu Ser Leu Gly
            435                  440                  445
```

<210> SEQ ID NO 145
<211> LENGTH: 11
<212> TYPE: PRT
<213> ORGANISM: Artificial Sequence
<220> FEATURE:
<223> OTHER INFORMATION: Synthetic (17_CDR-L1)

<400> SEQUENCE: 145

```
Arg Ala Ser Gln Ser Ile Ser Asn Tyr Leu Asn
1               5                  10
```

-continued

```
<210> SEQ ID NO 146
<211> LENGTH: 7
<212> TYPE: PRT
<213> ORGANISM: Artificial Sequence
<220> FEATURE:
<223> OTHER INFORMATION: Synthetic (17_CDR-L2)

<400> SEQUENCE: 146

Ala Ala Ser Asn Met His Ser
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic (17_CDR-L3)

<400> SEQUENCE: 147

Gln Gln Ser His Ser Phe Pro Trp Thr
1               5

<210> SEQ ID NO 148
<211> LENGTH: 5
<212> TYPE: PRT
<213> ORGANISM: Artificial Sequence
<220> FEATURE:
<223> OTHER INFORMATION: Synthetic (17_CDR-H1)

<400> SEQUENCE: 148

Thr Tyr Ala Met Ser
1               5

<210> SEQ ID NO 149
<211> LENGTH: 17
<212> TYPE: PRT
<213> ORGANISM: Artificial Sequence
<220> FEATURE:
<223> OTHER INFORMATION: Synthetic (17_CDR-H2)

<400> SEQUENCE: 149

Gly Ile Ser Pro Thr Leu Gly Ile Ala Asn Tyr Ala Gln Lys Phe Gln
1               5                   10                  15

Gly

<210> SEQ ID NO 150
<211> LENGTH: 12
<212> TYPE: PRT
<213> ORGANISM: Artificial Sequence
<220> FEATURE:
<223> OTHER INFORMATION: Synthetic (17_CDR-H3)

<400> SEQUENCE: 150

Val Arg Tyr Ala Gly Trp Thr Gly Tyr Phe Asp Leu
1               5                   10

<210> SEQ ID NO 151
<211> LENGTH: 107
<212> TYPE: PRT
<213> ORGANISM: Artificial Sequence
<220> FEATURE:
<223> OTHER INFORMATION: Synthetic (17_LightChain_VariableRegion)

<400> SEQUENCE: 151

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Ser Ile Ser Asn Tyr
        20                  25                  30

Leu Asn Trp Tyr Gln Gln Lys Pro Gly Lys Ala Pro Lys Leu Leu Ile
        35                  40                  45

Tyr Ala Ala Ser Asn Met His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Phe Pro Trp
                85                  90                  95

Thr Phe Gly Gln Gly Thr Lys Val Glu Ile Lys
            100                 105
```

```
<210> SEQ ID NO 152
<211> LENGTH: 321
<212> TYPE: DNA
<213> ORGANISM: Artificial Sequence
<220> FEATURE:
<223> OTHER INFORMATION: Synthetic (17_LightChain_VariableRegion_gene)

<400> SEQUENCE: 152
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc caaaattgct gatttacgca gcatccaata tgcactctgg tgtaccgtcc     180
cgtttctctg gcagcggttc tggtacggat tttaccctga ccatctcaag cctccagcct     240
gaagattttg ccacctatta ttgtcagcaa tctcactctt ttccgtggac gttcgggcag     300
ggaactaaag tggaaattaa a                                               321
```

```
<210> SEQ ID NO 153
<211> LENGTH: 121
<212> TYPE: PRT
<213> ORGANISM: Artificial Sequence
<220> FEATURE:
<223> OTHER INFORMATION: Synthetic (17_HeavyChain_VariableRegion)

<400> SEQUENCE: 153

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
        20                  25                  30

Ala Met Ser Trp Val Arg Gln Ala Pro Gly Gln Gly Leu Glu Trp Met
        35                  40                  45

Gly Gly Ile Ser Pro Thr Leu Gly Ile Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Tyr Ala Gly Trp Thr Gly Tyr Phe Asp Leu Trp Gly
            100                 105                 110

Gln Gly Thr Leu Val Thr Val Ser Ser
        115                 120
```

```
<210> SEQ ID NO 154
<211> LENGTH: 363
<212> TYPE: DNA
<213> ORGANISM: Artificial Sequence
```

<220> FEATURE:
<223> OTHER INFORMATION: Synthetic (17_HeavyChain_VariableRegion_gene)

<400> SEQUENCE: 154

```
caagttcagc tggtccagag cggcgcagag gtgaagaagc ccggcagttc tgttaaggtt      60
tcctgcaaag cctcaggcgg gacttttagt acctacgcaa tgtcttgggt gcggcaggcg     120
cccggccagg gtctcgaatg gatggggggt atttctccaa ccctgggtat cgcaaactat     180
gcacaaaaat tccaaggccg cgtaactatt accgccgacg aatcaacctc caccgcctac     240
atggaactca gctctctgag gtcagaagac acggccgtct attattgcgc cagagttcgt     300
tacgcaggtt ggactggtta cttcgatctg tggggtcagg gtactctggt taccgtctca     360
tcg                                                                    363
```

<210> SEQ ID NO 155
<211> LENGTH: 214
<212> TYPE: PRT
<213> ORGANISM: Artificial Sequence
<220> FEATURE:
<223> OTHER INFORMATION: Synthetic (17_LightChain_Kappa)

<400> SEQUENCE: 155

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Met His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 156
<211> LENGTH: 447
<212> TYPE: PRT
<213> ORGANISM: Artificial Sequence
<220> FEATURE:
<223> OTHER INFORMATION: Synthetic (17_HeavyChain)

-continued

<400> SEQUENCE: 156

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Ala Met Ser Trp Val Arg Gln Ala Pro Gly Gln Gly Leu Glu Trp Met
            35                  40                  45

Gly Gly Ile Ser Pro Thr Leu Gly Ile Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Arg Tyr Ala Gly Trp Thr Gly Tyr Phe Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445

<210> SEQ ID NO 157
<211> LENGTH: 11
<212> TYPE: PRT
<213> ORGANISM: Artificial Sequence
<220> FEATURE:
<223> OTHER INFORMATION: Synthetic (18_CDR-L1)

<400> SEQUENCE: 157

Arg Ala Ser Gln Ser Ile Ser Arg Trp Leu Asn
1               5                   10

<210> SEQ ID NO 158
<211> LENGTH: 7
<212> TYPE: PRT
<213> ORGANISM: Artificial Sequence
<220> FEATURE:
<223> OTHER INFORMATION: Synthetic (18_CDR-L2)

<400> SEQUENCE: 158

Ala Ala Ser Arg Leu Gln Ser
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic (18_CDR-L3)

<400> SEQUENCE: 159

Gln Gln Ser Glu Ser Phe Pro Trp Thr
1               5

<210> SEQ ID NO 160
<211> LENGTH: 5
<212> TYPE: PRT
<213> ORGANISM: Artificial Sequence
<220> FEATURE:
<223> OTHER INFORMATION: Synthetic (18_CDR-H1)

<400> SEQUENCE: 160

Ser Tyr Asp Ile Asn
1               5

<210> SEQ ID NO 161
<211> LENGTH: 17
<212> TYPE: PRT
<213> ORGANISM: Artificial Sequence
<220> FEATURE:
<223> OTHER INFORMATION: Synthetic (18_CDR-H2)

<400> SEQUENCE: 161

Trp Ile Ile Pro Thr Ser Gly Ser Thr Asn Tyr Ala Gln Lys Phe Gln
1               5                   10                  15

Gly

<210> SEQ ID NO 162
<211> LENGTH: 12
<212> TYPE: PRT
<213> ORGANISM: Artificial Sequence
<220> FEATURE:
<223> OTHER INFORMATION: Synthetic (18_CDR-H3)

<400> SEQUENCE: 162

Asp Ser Gln Ser Ser Tyr Ile Gly Tyr Phe Asp Val
1               5                   10

<210> SEQ ID NO 163
<211> LENGTH: 107
<212> TYPE: PRT
<213> ORGANISM: Artificial Sequence
<220> FEATURE:
<223> OTHER INFORMATION: Synthetic (18_LightChain_VariableRegion)

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Trp
                20                  25                  30

Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Ser Phe Pro Trp
                85                  90                  95

Thr Phe Gly Gln Gly Thr Lys Val Glu Ile Lys
            100                 105

<210> SEQ ID NO 164
<211> LENGTH: 321
<212> TYPE: DNA
<213> ORGANISM: Artificial Sequence
<220> FEATURE:
<223> OTHER INFORMATION: Synthetic (18_LightChain_VariableRegion_gene)

<400> SEQUENCE: 164
gacattcaaa tgacgcagag tccctcctca ctgagtgcta gcgtgggcga tcgtgtgaca         60
attacttgtc gcgctagcca gtctatctct cgttggctga actggtatca gcagaaaccg        120
ggcaaggcgc caaaattgct gatttacgca gcatcccgtc tgcagtctgg tgtaccgtcc        180
cgtttctctg gcagcggttc tggtacggat tttaccctga ccatctcaag cctccagcct        240
gaagattttg ccacctatta ttgtcagcaa tctgaatctt ttccgtggac gttcgggcag        300
ggaactaaag tggaaattaa a                                                  321

<210> SEQ ID NO 165
<211> LENGTH: 121
<212> TYPE: PRT
<213> ORGANISM: Artificial Sequence
<220> FEATURE:
<223> OTHER INFORMATION: Synthetic (18_HeavyChain_VariableRegion)

<400> SEQUENCE: 165

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Asp Ile Asn Trp Val Arg Gln Ala Pro Gly Gln Gly Leu Glu Trp Met
            35                  40                  45

```
Gly Trp Ile Ile Pro Thr Ser Gly Ser Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Gln Ser Ser Tyr Ile Gly Tyr Phe Asp Val Trp Gly
                100                 105                 110

Gln Gly Thr Leu Val Thr Val Ser Ser
        115                 120
```

```
<210> SEQ ID NO 166
<211> LENGTH: 363
<212> TYPE: DNA
<213> ORGANISM: Artificial Sequence
<220> FEATURE:
<223> OTHER INFORMATION: Synthetic (18_HeavyChain_VariableRegion_gene)

<400> SEQUENCE: 166
caagttcagc tggtccagag cggcgcagag gtgaagaagc ccggcagttc tgttaaggtt      60
tcctgcaaag cctcaggcgg gacttttagt tcttacgata tcaactgggt gcggcaggcg     120
cccggccagg gtctcgaatg gatggggtgg attatcccaa cctctggttc taccaactat     180
gcacaaaaat tccaaggccg cgtaactatt accgccgacg aatcaacctc caccgcctac     240
atggaactca gctctctgag gtcagaagac acggccgtct attattgcgc cagagattct     300
cagtcttctt acatcggtta cttcgatgtt tggggtcagg gtactctggt taccgtctca     360
tcg                                                                   363
```

```
<210> SEQ ID NO 167
<211> LENGTH: 214
<212> TYPE: PRT
<213> ORGANISM: Artificial Sequence
<220> FEATURE:
<223> OTHER INFORMATION: Synthetic (18_LightChain_Kappa)

<400> SEQUENCE: 167
```

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Ile Ser Arg Trp
                20                  25                  30

Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
                165                     170                     175

Ser Thr Leu Thr Leu Ser Lys Ala Asp Tyr Glu Lys His Lys Val Tyr
                180                     185                     190

Ala Cys Glu Val Thr His Gln Gly Leu Ser Ser Pro Val Thr Lys Ser
                195                     200                     205

Phe Asn Arg Gly Glu Cys
        210

<210> SEQ ID NO 168
<211> LENGTH: 447
<212> TYPE: PRT
<213> ORGANISM: Artificial Sequence
<220> FEATURE:
<223> OTHER INFORMATION: Synthetic (18_HeavyChain)

<400> SEQUENCE: 168

Gln Val Gln Leu Val Gln Ser Gly Ala Glu Val Lys Lys Pro Gly Ser
1                       5                       10                      15

Ser Val Lys Val Ser Cys Lys Ala Ser Gly Gly Thr Phe Ser Ser Tyr
                20                      25                      30

Asp Ile Asn Trp Val Arg Gln Ala Pro Gly Gln Gly Leu Glu Trp Met
        35                      40                      45

Gly Trp Ile Ile Pro Thr Ser Gly Ser Thr Asn Tyr Ala Gln Lys Phe
        50                      55                      60

Gln Gly Arg Val Thr Ile Thr Ala Asp Glu Ser Thr Ser Thr Ala Tyr
65                      70                      75                      80

Met Glu Leu Ser Ser Leu Arg Ser Glu Asp Thr Ala Val Tyr Tyr Cys
                85                      90                      95

Ala Arg Asp Ser Gln Ser Ser Tyr Ile Gly Tyr Phe Asp Val Trp Gly
                100                     105                     110

Gln Gly Thr Leu Val Thr Val Ser Ser Ala Ser Thr Lys Gly Pro Ser
                115                     120                     125

Val Phe Pro Leu Ala Pro Cys Ser Arg Ser Thr Ser Glu Ser Thr Ala
        130                     135                     140

Ala Leu Gly Cys Leu Val Lys Asp Tyr Phe Pro Glu Pro Val Thr Val
145                     150                     155                     160

Ser Trp Asn Ser Gly Ala Leu Thr Ser Gly Val His Thr Phe Pro Ala
                165                     170                     175

Val Leu Gln Ser Ser Gly Leu Tyr Ser Leu Ser Ser Val Val Thr Val
                180                     185                     190

Pro Ser Ser Ser Leu Gly Thr Lys Thr Tyr Thr Cys Asn Val Asp His
                195                     200                     205

Lys Pro Ser Asn Thr Lys Val Asp Lys Arg Val Glu Ser Lys Tyr Gly
        210                     215                     220

Pro Pro Cys Pro Pro Cys Pro Ala Pro Glu Ala Ala Gly Gly Pro Ser
225                     230                     235                     240

Val Phe Leu Phe Pro Pro Lys Pro Lys Asp Thr Leu Met Ile Ser Arg
                245                     250                     255

Thr Pro Glu Val Thr Cys Val Val Val Asp Val Ser Gln Glu Asp Pro
                260                     265                     270

Glu Val Gln Phe Asn Trp Tyr Val Asp Gly Val Glu Val His Asn Ala
                275                     280                     285

Lys Thr Lys Pro Arg Glu Glu Gln Phe Asn Ser Thr Tyr Arg Val Val
        290                     295                     300

```
Ser Val Leu Thr Val Leu His Gln Asp Trp Leu Asn Gly Lys Glu Tyr
305             310             315             320

Lys Cys Lys Val Ser Asn Lys Gly Leu Pro Ser Ser Ile Glu Lys Thr
            325             330             335

Ile Ser Lys Ala Lys Gly Gln Pro Arg Glu Pro Gln Val Tyr Thr Leu
            340             345             350

Pro Pro Ser Gln Glu Glu Met Thr Lys Asn Gln Val Ser Leu Thr Cys
            355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Arg Leu Thr Val Asp Lys Ser
                405             410             415

Arg Trp Gln Glu Gly Asn Val Phe Ser Cys Ser Val Met His Glu Ala
            420             425             430

Leu His Asn His Tyr Thr Gln Lys Ser Leu Ser Leu Ser Leu Gly
        435             440             445

<210> SEQ ID NO 169
<211> LENGTH: 11
<212> TYPE: PRT
<213> ORGANISM: Artificial Sequence
<220> FEATURE:
<223> OTHER INFORMATION: Synthetic (19_CDR-L1)

<400> SEQUENCE: 169

Arg Ala Ser Gln Ser Ile Ser Asn Tyr Leu Asn
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Synthetic (19_CDR-L2)

<400> SEQUENCE: 170

Asp Thr Ser Ser Leu Gln Ser
1               5

<210> SEQ ID NO 171
<211> LENGTH: 9
<212> TYPE: PRT
<213> ORGANISM: Artificial Sequence
<220> FEATURE:
<223> OTHER INFORMATION: Synthetic (19_CDR-L3)

<400> SEQUENCE: 171

Gln Gln Ser Tyr Ser Thr Pro Tyr Thr
1               5

<210> SEQ ID NO 172
<211> LENGTH: 5
<212> TYPE: PRT
<213> ORGANISM: Artificial Sequence
<220> FEATURE:
<223> OTHER INFORMATION: Synthetic (19_CDR-H1)

<400> SEQUENCE: 172

Ala Tyr Gly Ile Ser
1               5
```

```
<210> SEQ ID NO 173
<211> LENGTH: 17
<212> TYPE: PRT
<213> ORGANISM: Artificial Sequence
<220> FEATURE:
<223> OTHER INFORMATION: Synthetic (19_CDR-H2)

<400> SEQUENCE: 173

Arg Ile Ile Pro Tyr Leu Gly Thr Ala Asn Tyr Ala Gln Lys Phe Gln
1               5                   10                  15

Gly

<210> SEQ ID NO 174
<211> LENGTH: 12
<212> TYPE: PRT
<213> ORGANISM: Artificial Sequence
<220> FEATURE:
<223> OTHER INFORMATION: Synthetic (19_CDR-H3)

<400> SEQUENCE: 174

Leu Ser Tyr Gly Ile Gly Tyr Glu Ser Phe Asp Val
1               5                   10

<210> SEQ ID NO 175
<211> LENGTH: 107
<212> TYPE: PRT
<213> ORGANISM: Artificial Sequence
<220> FEATURE:
<223> OTHER INFORMATION: Synthetic (19_LightChain_VariableRegion)

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 176
<211> LENGTH: 321
<212> TYPE: DNA
<213> ORGANISM: Artificial Sequence
<220> FEATURE:
<223> OTHER INFORMATION: Synthetic (19_LightChain_VariableRegion_gene)

<400> SEQUENCE: 176
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc aaaaattgct gatttacgat acttcctctc tgcagtctgg tgtaccgtcc     180
cgtttctctg gcagcggttc tggtacggat tttaccctga ccatctcaag cctccagcct     240
gaagattttg ccacctatta ttgtcagcaa tcttactcta ctccgtacac gttcgggcag     300
```
ggaactaaag tggaaattaa a                                                      321

<210> SEQ ID NO 177
<211> LENGTH: 121
<212> TYPE: PRT
<213> ORGANISM: Artificial Sequence
<220> FEATURE:
<223> OTHER INFORMATION: Synthetic (19_HeavyChain_VariableRegion)

<400> SEQUENCE: 177

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Gly Ile Ser Trp Val Arg Gln Ala Pro Gly Gln Gly Leu Glu Trp Met
        35                  40                  45

Gly Arg Ile Ile Pro Tyr Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Tyr Gly Ile Gly Tyr Glu Ser Phe Asp Val Trp Gly
            100                 105                 110

Gln Gly Thr Leu Val Thr Val Ser Ser
        115                 120

<210> SEQ ID NO 178
<211> LENGTH: 363
<212> TYPE: DNA
<213> ORGANISM: Artificial Sequence
<220> FEATURE:
<223> OTHER INFORMATION: Synthetic (19_HeavyChain_VariableRegion_gene)

<400> SEQUENCE: 178
caagttcagc tggtccagag cggcgcagag gtgaagaagc ccggcagttc tgttaaggtt      60
tcctgcaaag cctcaggcgg gactttagt gcatacggta tctcttgggt gcggcaggcg      120
cccggccagg gtctcgaatg gatggggcgt attatcccat acctgggtac cgcaaactat      180
gcacaaaaat tccaaggccg cgtaactatt accgccgacg aatcaacctc caccgcctac      240
atggaactca gctctctgag gtcagaagac acggccgtct attattgcgc cagactgtct      300
tacggtatcg gttacgaatc tttcgatgtt tggggtcagg gcactttagt gaccgtctca      360
tcg                                                                    363

<210> SEQ ID NO 179
<211> LENGTH: 214
<212> TYPE: PRT
<213> ORGANISM: Artificial Sequence
<220> FEATURE:
<223> OTHER INFORMATION: Synthetic (19_LightChain_Kappa)

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

-continued

```
Tyr Asp Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 180
<211> LENGTH: 447
<212> TYPE: PRT
<213> ORGANISM: Artificial Sequence
<220> FEATURE:
<223> OTHER INFORMATION: Synthetic (19_HeavyChain)

<400> SEQUENCE: 180
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Tyr
            20                  25                  30

Gly Ile Ser Trp Val Arg Gln Ala Pro Gly Gln Gly Leu Glu Trp Met
            35                  40                  45

Gly Arg Ile Ile Pro Tyr Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Leu Ser Tyr Gly Ile Gly Tyr Glu Ser Phe Asp Val Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190
```

```
Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
        435                 440                 445
```

<210> SEQ ID NO 181
<211> LENGTH: 11
<212> TYPE: PRT
<213> ORGANISM: Artificial Sequence
<220> FEATURE:
<223> OTHER INFORMATION: Synthetic (20_CDR-L1)

<400> SEQUENCE: 181

```
Arg Ala Ser Gln Ser Ile Ser Ser Tyr Leu Asn
1               5                   10
```

<210> SEQ ID NO 182
<211> LENGTH: 7
<212> TYPE: PRT
<213> ORGANISM: Artificial Sequence
<220> FEATURE:
<223> OTHER INFORMATION: Synthetic (20_CDR-L2)

<400> SEQUENCE: 182

```
Asp Thr Ser Thr Leu Gln Ser
1               5
```

<210> SEQ ID NO 183
<211> LENGTH: 9
<212> TYPE: PRT

<213> ORGANISM: Artificial Sequence
<220> FEATURE:
<223> OTHER INFORMATION: Synthetic (20_CDR-L3)

<400> SEQUENCE: 183

Gln Gln Ser Tyr Ser Phe Pro Trp Thr
1               5

<210> SEQ ID NO 184
<211> LENGTH: 5
<212> TYPE: PRT
<213> ORGANISM: Artificial Sequence
<220> FEATURE:
<223> OTHER INFORMATION: Synthetic (20_CDR-H1)

<400> SEQUENCE: 184

Ser Tyr Ala Met Ser
1               5

<210> SEQ ID NO 185
<211> LENGTH: 17
<212> TYPE: PRT
<213> ORGANISM: Artificial Sequence
<220> FEATURE:
<223> OTHER INFORMATION: Synthetic (20_CDR-H2)

<400> SEQUENCE: 185

Ser Ile Ser Ser Ser Gly Gly Ser Thr Tyr Tyr Ala Asp Ser Val Lys
1               5                   10                  15

Gly

<210> SEQ ID NO 186
<211> LENGTH: 12
<212> TYPE: PRT
<213> ORGANISM: Artificial Sequence
<220> FEATURE:
<223> OTHER INFORMATION: Synthetic (20_CDR-H3)

<400> SEQUENCE: 186

Glu Leu Gly Gly Tyr Gly Phe Ser Tyr Phe Asp Tyr
1               5                   10

<210> SEQ ID NO 187
<211> LENGTH: 107
<212> TYPE: PRT
<213> ORGANISM: Artificial Sequence
<220> FEATURE:
<223> OTHER INFORMATION: Synthetic (20_LightChain_VariableRegion)

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys

```
                100                 105
```

<210> SEQ ID NO 188
<211> LENGTH: 321
<212> TYPE: DNA
<213> ORGANISM: Artificial Sequence
<220> FEATURE:
<223> OTHER INFORMATION: Synthetic (20_LightChain_VariableRegion_gene)

<400> SEQUENCE: 188

```
gacattcaaa tgacgcagag tccctcctca ctgagtgcta gcgtgggcga tcgtgtgaca        60
attacttgtc gcgctagcca gtctatctct tcttacctga actggtatca gcagaaaccg       120
ggcaaggcgc caaaattgct gatttacgat acttccactc tgcagtctgg tgtaccgtcc       180
cgtttctctg gcagcggttc tggtacggat tttacccctga ccatctcaag cctccagcct      240
gaagattttg ccacctatta ttgtcagcaa tcttactctt ttccgtggac gttcgggcag       300
ggaactaaag tggaaattaa a                                                 321
```

<210> SEQ ID NO 189
<211> LENGTH: 121
<212> TYPE: PRT
<213> ORGANISM: Artificial Sequence
<220> FEATURE:
<223> OTHER INFORMATION: Synthetic (20_HeavyChain_VariableRegion)

<400> SEQUENCE: 189

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Met Ser Trp Val Arg Gln Ala Pro Gly Gln Gly Leu Glu Trp Met
            35                  40                  45

Gly Ser Ile Ser Ser Ser Gly Gly Ser Thr Tyr Tyr Ala Asp Ser Val
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Leu Gly Gly Tyr Gly Phe Ser Tyr Phe Asp Tyr Trp Gly
            100                 105                 110

Gln Gly Thr Leu Val Thr Val Ser Ser
        115                 120
```

<210> SEQ ID NO 190
<211> LENGTH: 363
<212> TYPE: DNA
<213> ORGANISM: Artificial Sequence
<220> FEATURE:
<223> OTHER INFORMATION: Synthetic (20_HeavyChain_VariableRegion_gene)

<400> SEQUENCE: 190

```
caagttcagc tggtccagag cggcgcagag gtgaagaagc ccggcagttc tgttaaggtt        60
tcctgcaaag cctcaggcgg gactttagt tcttatgcaa tgtcttggt gcggcaggcg         120 cccggccagg gtctcgaatg gatggggtct atctcttctt ctggtggttc tacttactat       180
gccgattcag tgaagggtcg cgtaactatt accgccgacg aatcaacctc caccgcctac       240
atggaactca gctctctgag gtcagaagac acggccgtct attattgcgc cagagaactg       300
ggtggttacg gtttctctta cttcgattac tggggtcagg gcactttagt gaccgtctca       360
```

-continued tcg                                                                                       363

<210> SEQ ID NO 191
<211> LENGTH: 214
<212> TYPE: PRT
<213> ORGANISM: Artificial Sequence
<220> FEATURE:
<223> OTHER INFORMATION: Synthetic (20_LightChain_Kappa)

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 192
<211> LENGTH: 447
<212> TYPE: PRT
<213> ORGANISM: Artificial Sequence
<220> FEATURE:
<223> OTHER INFORMATION: Synthetic (20_HeavyChain)

<400> SEQUENCE: 192

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met Ser Trp Val Arg Gln Ala Pro Gly Gln Gly Leu Glu Trp Met
        35                  40                  45

Gly Ser Ile Ser Ser Ser Gly Gly Ser Thr Tyr Tyr Ala Asp Ser Val
    50                  55                  60

Lys Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Glu Leu Gly Gly Tyr Gly Phe Ser Tyr Phe Asp Tyr Trp Gly
               100                 105                 110

Gln Gly Thr Leu Val Thr Val Ser Ser Ala Ser Thr Lys Gly Pro Ser
               115                 120                 125

Val Phe Pro Leu Ala Pro Cys Ser Arg Ser Thr Ser Glu Ser Thr Ala
       130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
               165                 170                 175

Val Leu Gln Ser Ser Gly Leu Tyr Ser Leu Ser Ser Val Val Thr Val
               180                 185                 190

Pro Ser Ser Ser Leu Gly Thr Lys Thr Tyr Thr Cys Asn Val Asp His
       195                 200                 205

Lys Pro Ser Asn Thr Lys Val Asp Lys Arg Val Glu Ser Lys Tyr Gly
       210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
               245                 250                 255

Thr Pro Glu Val Thr Cys Val Val Val Asp Val Ser Gln Glu Asp Pro
               260                 265                 270

Glu Val Gln Phe Asn Trp Tyr Val Asp Gly Val Glu Val His Asn Ala
               275                 280                 285

Lys Thr Lys Pro Arg Glu Glu Gln Phe Asn Ser Thr Tyr Arg Val Val
       290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
               325                 330                 335

Ile Ser Lys Ala Lys Gly Gln Pro Arg Glu Pro Gln Val Tyr Thr Leu
               340                 345                 350

Pro Pro Ser Gln Glu Glu Met Thr Lys Asn Gln Val Ser Leu Thr Cys
               355                 360                 365

Leu Val Lys Gly Phe Tyr Pro Ser Asp Ile Ala Val Glu Trp Glu Ser
       370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
               405                 410                 415

Arg Trp Gln Glu Gly Asn Val Phe Ser Cys Ser Val Met His Glu Ala
               420                 425                 430

Leu His Asn His Tyr Thr Gln Lys Ser Leu Ser Leu Ser Leu Gly
               435                 440                 445
```

<210> SEQ ID NO 193
<211> LENGTH: 11
<212> TYPE: PRT
<213> ORGANISM: Artificial Sequence
<220> FEATURE:
<223> OTHER INFORMATION: Synthetic (21_CDR-L1)

<400> SEQUENCE: 193

```
Arg Ala Ser Gln Ser Ile Arg Asn Tyr Leu Asn
1               5                   10

<210> SEQ ID NO 194
<211> LENGTH: 7
<212> TYPE: PRT
<213> ORGANISM: Artificial Sequence
<220> FEATURE:
<223> OTHER INFORMATION: Synthetic (21_CDR-L2)

<400> SEQUENCE: 194

Ala Thr Ser Ser Leu Gln Ser
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic (21_CDR-L3)

<400> SEQUENCE: 195

Gln Gln Ser Tyr Ser Phe Pro Trp Thr
1               5

<210> SEQ ID NO 196
<211> LENGTH: 5
<212> TYPE: PRT
<213> ORGANISM: Artificial Sequence
<220> FEATURE:
<223> OTHER INFORMATION: Synthetic (21_CDR-H1)

<400> SEQUENCE: 196

Asp Tyr Ala Met Ser
1               5

<210> SEQ ID NO 197
<211> LENGTH: 15
<212> TYPE: PRT
<213> ORGANISM: Artificial Sequence
<220> FEATURE:
<223> OTHER INFORMATION: Synthetic (21_CDR-H2)

<400> SEQUENCE: 197

Gly Ile Ser Gly Ser Asp Ile Tyr Tyr Ala Asp Ser Val Lys Gly
1               5                   10                  15

<210> SEQ ID NO 198
<211> LENGTH: 11
<212> TYPE: PRT
<213> ORGANISM: Artificial Sequence
<220> FEATURE:
<223> OTHER INFORMATION: Synthetic (21_CDR-H3)

<400> SEQUENCE: 198

Ala Val Ser Tyr Trp Ser Tyr Thr Phe Asp Tyr
1               5                   10

<210> SEQ ID NO 199
<211> LENGTH: 107
<212> TYPE: PRT
<213> ORGANISM: Artificial Sequence
<220> FEATURE:
<223> OTHER INFORMATION: Synthetic (21_LightChain_VariableRegion)

<400> SEQUENCE: 199
```

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Arg Asn Tyr
            20              25              30

Leu Asn Trp Tyr Gln Gln Lys Pro Gly Lys Ala Pro Lys Leu Leu Ile
        35              40              45

Tyr Ala Thr Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Phe Pro Trp
                85              90              95

Thr Phe Gly Gln Gly Thr Lys Val Glu Ile Lys
            100             105
```

```
<210> SEQ ID NO 200
<211> LENGTH: 321
<212> TYPE: DNA
<213> ORGANISM: Artificial Sequence
<220> FEATURE:
<223> OTHER INFORMATION: Synthetic (21_LightChain_VariableRegion_gene)

<400> SEQUENCE: 200
gacattcaaa tgacgcagag tccctcctca ctgagtgcta gcgtgggcga tcgtgtgaca        60
attacttgtc gcgctagcca gtctatccgt aattacctga actggtatca gcagaaaccg       120
ggcaaggcgc caaaattgct gatttacgca acttcctctc tgcagtctgg tgtaccgtcc       180
cgtttctctg gcagcggttc tggtacggat tttaccctga ccatctcaag cctccagcct       240
gaagattttg ccacctatta ttgtcagcaa tcttactctt ttccgtggac gttcgggcag       300
ggaactaaag tggaaattaa a                                                 321
```

```
<210> SEQ ID NO 201
<211> LENGTH: 118
<212> TYPE: PRT
<213> ORGANISM: Artificial Sequence
<220> FEATURE:
<223> OTHER INFORMATION: Synthetic (21_HeavyChain_VariableRegion)

<400> SEQUENCE: 201

Gln Val Gln Leu Val Gln Ser Gly Ala Glu Val Lys Lys Pro Gly Ser
1               5               10              15

Ser Val Lys Val Ser Cys Lys Ala Ser Gly Gly Thr Phe Ser Asp Tyr
            20              25              30

Ala Met Ser Trp Val Arg Gln Ala Pro Gly Gln Gly Leu Glu Trp Met
        35              40              45

Gly Gly Ile Ser Gly Ser Asp Ile Tyr Tyr Ala Asp Ser Val Lys Gly
    50              55              60

Arg Val Thr Ile Thr Ala Asp Glu Ser Thr Ser Thr Ala Tyr Met Glu
65              70              75              80

Leu Ser Ser Leu Arg Ser Glu Asp Thr Ala Val Tyr Tyr Cys Ala Arg
                85              90              95

Ala Val Ser Tyr Trp Ser Tyr Thr Phe Asp Tyr Trp Gly Gln Gly Thr
            100             105             110

Leu Val Thr Val Ser Ser
        115
```

```
<210> SEQ ID NO 202
```

-continued

<211> LENGTH: 354
<212> TYPE: DNA
<213> ORGANISM: Artificial Sequence
<220> FEATURE:
<223> OTHER INFORMATION: Synthetic (21_HeavyChain_VariableRegion_gene)

<400> SEQUENCE: 202
caagttcagc tggtccagag cggcgcagag gtgaagaagc ccggcagttc tgttaaggtt      60
tcctgcaaag cctcaggcgg gacttttagt gattatgcaa tgtcttgggt gcggcaggcg     120
cccggccagg gtctcgaatg gatggggggt atctctggtt ctgatatcta ctatgccgat     180
tcagtgaagg gtcgcgtaac tattaccgcc gacgaatcaa cctccaccgc ctacatggaa     240
ctcagctctc tgaggtcaga agacacggcc gtctattatt gcgccagagc agtttcttac     300
tggtcttaca cttttgatta ctggggtcag ggcactttag tgaccgtctc atcg           354

<210> SEQ ID NO 203
<211> LENGTH: 214
<212> TYPE: PRT
<213> ORGANISM: Artificial Sequence
<220> FEATURE:
<223> OTHER INFORMATION: Synthetic (21_LightChain_Kappa)

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 204
<211> LENGTH: 444
<212> TYPE: PRT
<213> ORGANISM: Artificial Sequence
<220> FEATURE:
<223> OTHER INFORMATION: Synthetic (21_HeavyChain)

<400> SEQUENCE: 204

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Met Ser Trp Val Arg Gln Ala Pro Gly Gln Gly Leu Glu Trp Met
        35                  40                  45

Gly Gly Ile Ser Gly Ser Asp Ile Tyr Tyr Ala Asp Ser Val Lys Gly
    50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Ala Val Ser Tyr Trp Ser Tyr Thr Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
```

-continued

```
              405               410               415
Glu Gly Asn Val Phe Ser Cys Ser Val Met His Glu Ala Leu His Asn
        420               425               430

His Tyr Thr Gln Lys Ser Leu Ser Leu Ser Leu Gly
      435               440

<210> SEQ ID NO 205
<211> LENGTH: 11
<212> TYPE: PRT
<213> ORGANISM: Artificial Sequence
<220> FEATURE:
<223> OTHER INFORMATION: Synthetic (22_CDR-L1)

<400> SEQUENCE: 205

Arg Ala Ser Gln Ser Ile Gly Ser Tyr Leu Asn
1               5               10

<210> SEQ ID NO 206
<211> LENGTH: 7
<212> TYPE: PRT
<213> ORGANISM: Artificial Sequence
<220> FEATURE:
<223> OTHER INFORMATION: Synthetic (22_CDR-L2)

<400> SEQUENCE: 206

Asp Ala Ser Thr Leu Gln Ser
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic (22_CDR-L3)

<400> SEQUENCE: 207

Gln Gln Ser Tyr Ser Phe Pro Trp Thr
1               5

<210> SEQ ID NO 208
<211> LENGTH: 5
<212> TYPE: PRT
<213> ORGANISM: Artificial Sequence
<220> FEATURE:
<223> OTHER INFORMATION: Synthetic (22_CDR-H1)

<400> SEQUENCE: 208

Ser Tyr Ala Met His
1               5

<210> SEQ ID NO 209
<211> LENGTH: 17
<212> TYPE: PRT
<213> ORGANISM: Artificial Sequence
<220> FEATURE:
<223> OTHER INFORMATION: Synthetic (22_CDR-H2)

<400> SEQUENCE: 209

Gly Ile Ser Ser Ser Gly Gly Thr Thr Tyr Tyr Ala Asp Ser Val Lys
1               5               10               15

Gly

<210> SEQ ID NO 210
<211> LENGTH: 12
<212> TYPE: PRT
```

-continued

<210> ORGANISM: Artificial Sequence
<220> FEATURE:
<223> OTHER INFORMATION: Synthetic (22_CDR-H3)

<400> SEQUENCE: 210

Ala Leu Gly Val Val Gly Gly Thr Trp Phe Asp Tyr
1               5                   10

<210> SEQ ID NO 211
<211> LENGTH: 107
<212> TYPE: PRT
<213> ORGANISM: Artificial Sequence
<220> FEATURE:
<223> OTHER INFORMATION: Synthetic (22_LightChain_VariableRegion)

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105

<210> SEQ ID NO 212
<211> LENGTH: 321
<212> TYPE: DNA
<213> ORGANISM: Artificial Sequence
<220> FEATURE:
<223> OTHER INFORMATION: Synthetic (22_LightChain_VariableRegion_gene)

<400> SEQUENCE: 212
gacattcaaa tgacgcagag tccctcctca ctgagtgcta gcgtgggcga tcgtgtgaca      60
attacttgtc gcgctagcca gtctatcggt tcttacctga actggtatca gcagaaaccg     120
ggcaaggcgc caaaattgct gatttacgat gcatccactc tgcagtctgg tgtaccgtcc     180
cgtttctctg gcagcggttc tggtacggat tttaccctga ccatctcaag cctccagcct     240
gaagattttg ccacctatta ttgtcagcaa tcttactctt tccgtggac gttcgggcag     300 ggaactaaag tggaaattaa a                                             321

<210> SEQ ID NO 213
<211> LENGTH: 121
<212> TYPE: PRT
<213> ORGANISM: Artificial Sequence
<220> FEATURE:
<223> OTHER INFORMATION: Synthetic (22_HeavyChain_VariableRegion)

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Met His Trp Val Arg Gln Ala Pro Gly Gln Gly Leu Glu Trp Met

-continued

```
           35                  40                  45
Gly Gly Ile Ser Ser Ser Gly Gly Thr Thr Tyr Tyr Ala Asp Ser Val
      50                  55                  60
Lys Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ala Leu Gly Val Val Gly Gly Thr Trp Phe Asp Tyr Trp Gly
           100                 105                 110
Gln Gly Thr Leu Val Thr Val Ser Ser
        115                 120

<210> SEQ ID NO 214
<211> LENGTH: 363
<212> TYPE: DNA
<213> ORGANISM: Artificial Sequence
<220> FEATURE:
<223> OTHER INFORMATION: Synthetic (22_HeavyChain_VariableRegion_gene)

<400> SEQUENCE: 214
caagttcagc tggtccagag cggcgcagag gtgaagaagc ccggcagttc tgttaaggtt      60
tcctgcaaag cctcaggcgg gactttagt tcttatgcaa tgcactgggt gcggcaggcg     120
cccggccagg gtctcgaatg gatggggggt atctcttctt ctggtggtac tacttactat     180
gccgattcag tgaagggtcg cgtaactatt accgccgacg aatcaacctc caccgcctac     240
atggaactca gctctctgag gtcagaagac acggccgtct attattgcgc cagagcactg     300
ggtgttgttg gtggtacttg gttcgattac tggggtcagg gcactttagt gaccgtctca     360
tcg                                                                    363

<210> SEQ ID NO 215
<211> LENGTH: 214
<212> TYPE: PRT
<213> ORGANISM: Artificial Sequence
<220> FEATURE:
<223> OTHER INFORMATION: Synthetic (22_LightChain_Kappa)

<400> SEQUENCE: 215

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Gly Ser Tyr
                20                  25                  30
Leu Asn Trp Tyr Gln Gln Lys Pro Gly Lys Ala Pro Lys Leu Leu Ile
           35                  40                  45
Tyr Asp Ala Ser Thr Leu Gln Ser Gly Val Pro Ser Arg Phe Ser Gly
      50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Phe Pro Trp
                85                  90                  95
Thr Phe Gly Gln Gly Thr Lys Val Glu Ile Lys Arg Thr Val Ala Ala
           100                 105                 110
Pro Ser Val Phe Ile Phe Pro Pro Ser Asp Glu Gln Leu Lys Ser Gly
           115                 120                 125
Thr Ala Ser Val Val Cys Leu Leu Asn Asn Phe Tyr Pro Arg Glu Ala
      130                 135                 140
Lys Val Gln Trp Lys Val Asp Asn Ala Leu Gln Ser Gly Asn Ser Gln
```

```
145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 216
<211> LENGTH: 447
<212> TYPE: PRT
<213> ORGANISM: Artificial Sequence
<220> FEATURE:
<223> OTHER INFORMATION: Synthetic (22_HeavyChain)

<400> SEQUENCE: 216

Gln Val Gln Leu Val Gln Ser Gly Ala Glu Val Lys Lys Pro Gly Ser
1                 5                 10                 15

Ser Val Lys Val Ser Cys Lys Ala Ser Gly Gly Thr Phe Ser Ser Tyr
                20                 25                 30

Ala Met His Trp Val Arg Gln Ala Pro Gly Gln Gly Leu Glu Trp Met
                35                 40                 45

Gly Gly Ile Ser Ser Ser Gly Gly Thr Thr Tyr Tyr Ala Asp Ser Val
                50                 55                 60

Lys Gly Arg Val Thr Ile Thr Ala Asp Glu Ser Thr Ser Thr Ala Tyr
65                 70                 75                 80

Met Glu Leu Ser Ser Leu Arg Ser Glu Asp Thr Ala Val Tyr Tyr Cys
                85                 90                 95

Ala Arg Ala Leu Gly Val Val Gly Gly Thr Trp Phe Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
                195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
```

-continued

```
            290             295             300
Ser Val Leu Thr Val Leu His Gln Asp Trp Leu Asn Gly Lys Glu Tyr
305                 310             315                 320

Lys Cys Lys Val Ser Asn Lys Gly Leu Pro Ser Ser Ile Glu Lys Thr
                325             330             335

Ile Ser Lys Ala Lys Gly Gln Pro Arg Glu Pro Gln Val Tyr Thr Leu
            340             345             350

Pro Pro Ser Gln Glu Glu Met Thr Lys Asn Gln Val Ser Leu Thr Cys
        355             360             365

Leu Val Lys Gly Phe Tyr Pro Ser Asp Ile Ala Val Glu Trp Glu Ser
        370             375             380

Asn Gly Gln Pro Glu Asn Asn Tyr Lys Thr Thr Pro Pro Val Leu Asp
385             390             395             400

Ser Asp Gly Ser Phe Phe Leu Tyr Ser Arg Leu Thr Val Asp Lys Ser
                405             410             415

Arg Trp Gln Glu Gly Asn Val Phe Ser Cys Ser Val Met His Glu Ala
            420             425             430

Leu His Asn His Tyr Thr Gln Lys Ser Leu Ser Leu Ser Leu Gly
        435             440             445

<210> SEQ ID NO 217
<211> LENGTH: 11
<212> TYPE: PRT
<213> ORGANISM: Artificial Sequence
<220> FEATURE:
<223> OTHER INFORMATION: Synthetic (23_CDR-L1)

<400> SEQUENCE: 217

Arg Ala Ser Gln Ser Ile Ser Asn Tyr Leu Asn
1               5               10

<210> SEQ ID NO 218
<211> LENGTH: 7
<212> TYPE: PRT
<213> ORGANISM: Artificial Sequence
<220> FEATURE:
<223> OTHER INFORMATION: Synthetic (23_CDR-L2)

<400> SEQUENCE: 218

Asp Thr Ser Thr Leu Gln Ser
1               5

<210> SEQ ID NO 219
<211> LENGTH: 9
<212> TYPE: PRT
<213> ORGANISM: Artificial Sequence
<220> FEATURE:
<223> OTHER INFORMATION: Synthetic (23_CDR-L3)

<400> SEQUENCE: 219

Gln Gln Ser Tyr Ser Phe Pro Trp Thr
1               5

<210> SEQ ID NO 220
<211> LENGTH: 5
<212> TYPE: PRT
<213> ORGANISM: Artificial Sequence
<220> FEATURE:
<223> OTHER INFORMATION: Synthetic (23_CDR-H1)

<400> SEQUENCE: 220

Asp Tyr Ala Met His
```

-continued 1               5

<210> SEQ ID NO 221
<211> LENGTH: 17
<212> TYPE: PRT
<213> ORGANISM: Artificial Sequence
<220> FEATURE:
<223> OTHER INFORMATION: Synthetic (23_CDR-H2)

<400> SEQUENCE: 221

Ala Ile Ser Gly Ser Gly Gly Tyr Thr His Tyr Ala Asp Ser Val Lys
1               5                   10                  15

Gly

<210> SEQ ID NO 222
<211> LENGTH: 12
<212> TYPE: PRT
<213> ORGANISM: Artificial Sequence
<220> FEATURE:
<223> OTHER INFORMATION: Synthetic (23_CDR-H3)

<400> SEQUENCE: 222

Ser Ala Thr Phe Gly Val Trp Glu Thr Phe Asp Val
1               5                   10

<210> SEQ ID NO 223
<211> LENGTH: 107
<212> TYPE: PRT
<213> ORGANISM: Artificial Sequence
<220> FEATURE:
<223> OTHER INFORMATION: Synthetic (23_LightChain_VariableRegion)

<400> SEQUENCE: 223

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Thr Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Phe Pro Trp
                85                  90                  95

Thr Phe Gly Gln Gly Thr Lys Val Glu Ile Lys
            100                 105

<210> SEQ ID NO 224
<211> LENGTH: 321
<212> TYPE: DNA
<213> ORGANISM: Artificial Sequence
<220> FEATURE:
<223> OTHER INFORMATION: Synthetic (23_LightChain_VariableRegion_gene)

<400> SEQUENCE: 224
gacattcaaa tgacgcagag tccctcctca ctgagtgcta gcgtgggcga tcgtgtgaca      60
attacttgtc gcgctagcca gtctatctct aattacctga actggtatca gcagaaaccg     120
ggcaaggcgc caaaattgct gatttacgat acttccactc tgcagtctgg tgtaccgtcc     180
cgtttctctg gcagcggttc tggtacggat tttaccctga ccatctcaag cctccagcct     240

```
gaagattttg ccacctatta ttgtcagcaa tcttactctt ttccgtggac gttcgggcag      300
ggaactaaag tggaaattaa a                                                 321
```

<210> SEQ ID NO 225
<211> LENGTH: 121
<212> TYPE: PRT
<213> ORGANISM: Artificial Sequence
<220> FEATURE:
<223> OTHER INFORMATION: Synthetic (23_HeavyChain_VariableRegion)

<400> SEQUENCE: 225

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Met His Trp Val Arg Gln Ala Pro Gly Gln Gly Leu Glu Trp Met
        35                  40                  45

Gly Ala Ile Ser Gly Ser Gly Gly Tyr Thr His Tyr Ala Asp Ser Val
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Thr Phe Gly Val Trp Glu Thr Phe Asp Val Trp Gly
            100                 105                 110

Gln Gly Thr Leu Val Thr Val Ser Ser
        115                 120
```

<210> SEQ ID NO 226
<211> LENGTH: 363
<212> TYPE: DNA
<213> ORGANISM: Artificial Sequence
<220> FEATURE:
<223> OTHER INFORMATION: Synthetic (23_HeavyChain_VariableRegion_gene)

<400> SEQUENCE: 226

```
caagttcagc tggtccagag cggcgcagag gtgaagaagc ccggcagttc tgttaaggtt       60
tcctgcaaag cctcaggcgg gacttttagt gattatgcaa tgcactgggt gcggcaggcg      120
cccggccagg gtctcgaatg gatggggggca atctctggtt ctggtggtta cactcactat      180
gccgattcag tgaagggtcg cgtaactatt accgccgacg aatcaacctc caccgcctac      240
atggaactca gctctctgag gtcagaagac acggccgtct attattgcgc cagatctgca      300
actttcggtg tttgggaaac tttcgatgtt tggggtcagg gcactttagt gaccgtctca      360
tcg                                                                    363
```

<210> SEQ ID NO 227
<211> LENGTH: 214
<212> TYPE: PRT
<213> ORGANISM: Artificial Sequence
<220> FEATURE:
<223> OTHER INFORMATION: Synthetic (23_LightChain_Kappa)

<400> SEQUENCE: 227

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
```

-continued

```
            35                      40                      45

Tyr Asp Thr Ser Thr Leu Gln Ser Gly Val Pro Ser Arg Phe Ser Gly
    50                      55                      60

Ser Gly Ser Gly Thr Asp Phe Thr Leu Thr Ile Ser Ser Leu Gln Pro
65                      70                      75                      80

Glu Asp Phe Ala Thr Tyr Tyr Cys Gln Gln Ser Tyr Ser Phe Pro Trp
                85                      90                      95

Thr Phe Gly Gln Gly Thr Lys Val Glu Ile Lys Arg Thr Val Ala Ala
                100                     105                     110

Pro Ser Val Phe Ile Phe Pro Pro Ser Asp Glu Gln Leu Lys Ser Gly
                115                     120                     125

Thr Ala Ser Val Val Cys Leu Leu Asn Asn Phe Tyr Pro Arg Glu Ala
    130                     135                     140

Lys Val Gln Trp Lys Val Asp Asn Ala Leu Gln Ser Gly Asn Ser Gln
145                     150                     155                     160

Glu Ser Val Thr Glu Gln Asp Ser Lys Asp Ser Thr Tyr Ser Leu Ser
                165                     170                     175

Ser Thr Leu Thr Leu Ser Lys Ala Asp Tyr Glu Lys His Lys Val Tyr
                180                     185                     190

Ala Cys Glu Val Thr His Gln Gly Leu Ser Ser Pro Val Thr Lys Ser
                195                     200                     205

Phe Asn Arg Gly Glu Cys
    210
```

<210> SEQ ID NO 228
<211> LENGTH: 447
<212> TYPE: PRT
<213> ORGANISM: Artificial Sequence
<220> FEATURE:
<223> OTHER INFORMATION: Synthetic (23_HeavyChain)

<400> SEQUENCE: 228

```
Gln Val Gln Leu Val Gln Ser Gly Ala Glu Val Lys Lys Pro Gly Ser
1                       5                       10                      15

Ser Val Lys Val Ser Cys Lys Ala Ser Gly Gly Thr Phe Ser Asp Tyr
                20                      25                      30

Ala Met His Trp Val Arg Gln Ala Pro Gly Gln Gly Leu Glu Trp Met
            35                      40                      45

Gly Ala Ile Ser Gly Ser Gly Gly Tyr Thr His Tyr Ala Asp Ser Val
    50                      55                      60

Lys Gly Arg Val Thr Ile Thr Ala Asp Glu Ser Thr Ser Thr Ala Tyr
65                      70                      75                      80

Met Glu Leu Ser Ser Leu Arg Ser Glu Asp Thr Ala Val Tyr Tyr Cys
                85                      90                      95

Ala Arg Ser Ala Thr Phe Gly Val Trp Glu Thr Phe Asp Val Trp Gly
                100                     105                     110

Gln Gly Thr Leu Val Thr Val Ser Ser Ala Ser Thr Lys Gly Pro Ser
            115                     120                     125

Val Phe Pro Leu Ala Pro Cys Ser Arg Ser Thr Ser Glu Ser Thr Ala
    130                     135                     140

Ala Leu Gly Cys Leu Val Lys Asp Tyr Phe Pro Glu Pro Val Thr Val
145                     150                     155                     160

Ser Trp Asn Ser Gly Ala Leu Thr Ser Gly Val His Thr Phe Pro Ala
                165                     170                     175

Val Leu Gln Ser Ser Gly Leu Tyr Ser Leu Ser Ser Val Val Thr Val
```

-continued

```
                180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
    210                 215                 220
Pro Pro Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
            245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
            405                 410                 415
Arg Trp Gln Glu Gly Asn Val Phe Ser Cys Ser Val Met His Glu Ala
        420                 425                 430
Leu His Asn His Tyr Thr Gln Lys Ser Leu Ser Leu Ser Leu Gly
        435                 440                 445
```

<210> SEQ ID NO 229
<211> LENGTH: 326
<212> TYPE: PRT
<213> ORGANISM: Artificial Sequence
<220> FEATURE:
<223> OTHER INFORMATION: Synthetic (IgG4_Fc)

<400> SEQUENCE: 229

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
```

-continued

```
              100               105               110

Glu Ala Ala Gly Gly Pro Ser Val Phe Leu Phe Pro Pro Lys Pro Lys
            115               120               125

Asp Thr Leu Met Ile Ser Arg Thr Pro Glu Val Thr Cys Val Val Val
        130               135               140

Asp Val Ser Gln Glu Asp Pro Glu Val Gln Phe Asn Trp Tyr Val Asp
145               150               155               160

Gly Val Glu Val His Asn Ala Lys Thr Lys Pro Arg Glu Glu Gln Phe
                165               170               175

Asn Ser Thr Tyr Arg Val Val Ser Val Leu Thr Val Leu His Gln Asp
                180               185               190

Trp Leu Asn Gly Lys Glu Tyr Lys Cys Lys Val Ser Asn Lys Gly Leu
            195               200               205

Pro Ser Ser Ile Glu Lys Thr Ile Ser Lys Ala Lys Gly Gln Pro Arg
        210               215               220

Glu Pro Gln Val Tyr Thr Leu Pro Pro Ser Gln Glu Glu Met Thr Lys
225               230               235               240

Asn Gln Val Ser Leu Thr Cys Leu Val Lys Gly Phe Tyr Pro Ser Asp
                245               250               255

Ile Ala Val Glu Trp Glu Ser Asn Gly Gln Pro Glu Asn Asn Tyr Lys
            260               265               270

Thr Thr Pro Pro Val Leu Asp Ser Asp Gly Ser Phe Phe Leu Tyr Ser
        275               280               285

Arg Leu Thr Val Asp Lys Ser Arg Trp Gln Gln Gly Asn Val Phe Ser
    290               295               300

Cys Ser Val Met His Glu Ala Leu His Asn His Tyr Thr Gln Lys Ser
305               310               315               320

Leu Ser Leu Ser Leu Gly
                325

<210> SEQ ID NO 230
<211> LENGTH: 107
<212> TYPE: PRT
<213> ORGANISM: Artificial Sequence
<220> FEATURE:
<223> OTHER INFORMATION: Synthetic (Kappa_ConstatRegion)

<400> SEQUENCE: 230

Arg Thr Val Ala Ala Pro Ser Val Phe Ile Phe Pro Pro Ser Asp Glu
1               5               10               15

Gln Leu Lys Ser Gly Thr Ala Ser Val Val Cys Leu Leu Asn Asn Phe
            20               25               30

Tyr Pro Arg Glu Ala Lys Val Gln Trp Lys Val Asp Asn Ala Leu Gln
        35               40               45

Ser Gly Asn Ser Gln Glu Ser Val Thr Glu Gln Asp Ser Lys Asp Ser
    50               55               60

Thr Tyr Ser Leu Ser Ser Thr Leu Thr Leu Ser Lys Ala Asp Tyr Glu
65               70               75               80

Lys His Lys Val Tyr Ala Cys Glu Val Thr His Gln Gly Leu Ser Ser
                85               90               95

Pro Val Thr Lys Ser Phe Asn Arg Gly Glu Cys
            100               105
```